United States Patent
Singletary et al.

(10) Patent No.: US 7,317,146 B2
(45) Date of Patent: Jan. 8, 2008

(54) PRODUCTION OF CEREAL GRAIN WITH REDUCED STARCH GRANULE SIZE AND USES THEREOF

(75) Inventors: George W. Singletary, Ankeny, IA (US); Lan Zhou, Urbandale, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 87 days.

(21) Appl. No.: 11/021,464

(22) Filed: Dec. 22, 2004

(65) Prior Publication Data

US 2005/0160496 A1 Jul. 21, 2005

Related U.S. Application Data

(60) Provisional application No. 60/533,762, filed on Dec. 31, 2003.

(51) Int. Cl.
  C12N 15/82    (2006.01)
  C12N 15/52    (2006.01)
  C12N 15/29    (2006.01)
  A01H 5/00     (2006.01)
  A01H 5/10     (2006.01)

(52) U.S. Cl. ................ 800/320.1; 800/278; 800/284; 800/287; 800/290; 435/468; 435/320.1; 536/23.1; 536/23.6

(58) Field of Classification Search .................... None
See application file for complete search history.

(56) References Cited

U.S. PATENT DOCUMENTS

| | | | |
|---|---|---|---|
| 5,723,764 A | | 3/1998 | Nichols et al. |
| 5,824,798 A | * | 10/1998 | Tallberg et al. ............ 536/128 |
| 5,912,413 A | * | 6/1999 | Myers et al. ............... 800/298 |
| 6,197,588 B1 | | 3/2001 | Gray et al. |
| 6,423,886 B1 | | 7/2002 | Singletary et al. |
| 6,429,359 B1 | | 8/2002 | Lamppa |
| 6,468,799 B1 | | 10/2002 | Burrell |
| 6,653,099 B1 | * | 11/2003 | Famodu et al. ............ 435/69.1 |
| 6,812,382 B1 | * | 11/2004 | Hitz et al. ................. 800/295 |

FOREIGN PATENT DOCUMENTS

WO    WO 03/035874 A1    5/2003

OTHER PUBLICATIONS

Patron et al Plant Physiology 2002, 130: 190-198.*
Edwards et al The Plant Cell 2002, 14: 1767-1785.*
Salehuzzaman et al 1999, Plant, Cell and Environment 22:1311-1318.*
Bechtel, D.B. and Wilson, J., "Variability in a Starch Isolation Method and Automated Digital Image Analysis System Used for the Study of Starch Size Distributions in Wheat Flour," *Cereal Chem.*, 2000, pp. 401-405, vol. 77, No. 3.
Borem, A., et al., "Size Distribution of Starch Granules in Mature Barley Kernels," *Arq. Biol. Technol.* Jun. 1997, pp. 397-404, vol. 40, No. 2.
Boyer, C.D., et al., "Changes in Starch Granule Size and Amylose Percentage During Kernel Development in Several *Zea Mays* L. Genotypes," *Cereal Chem.*, 1976, pp. 327-337, vol. 53, No. 3.
Campbell, M.R., et al., "Variation of Starch Granule Size in Tropical Maize Germ Plasm," *Cereal Chem.*, 1996, pp. 536-538, vol. 73, No. 5.
Chiotelli, E., and LeMeste, M., "Effect of Small and Large Wheat Starch Granules on Thermomechanical Behavior of Starch," *Cereal Chem.*, 2002, pp. 286-293, vol. 79, No. 2.
Chojecki, A.J.S., "The Number and Sizes of Starch Granules in the Wheat Endosperm, and their Association with Grain Weight," *Annals of Botany*, 1986, pp. 819-831, vol. 58.
Dengate, H. and Meredith, P., "Variation in Size Distribution of Starch Granules from Wheat Grain," *Journal of Cereal Science*, 1984, pp. 83-90, vol. 2.
Gaines, C.S., et al., "Associations of Starch Gel Hardness, Granule Size, Waxy Allelic Expression, Thermal Pasting, Milling Quality, and Kernel Texture of 12 Soft Wheat Cultivars," *Cereal Chem.*, 2000, pp. 163-168, vol. 77, No. 2.
Gutierrez, O.A., et al., "Starch particle Volume in Single- and Double-Mutant Maize Endosperm Genotypes Involving the Soft Starch (h) Gene," *Crop Sci.*, Mar.-Apr. 2002, pp. 355-359, vol. 42.
Hageman, J. et al., "Protein Import into and Sorting Inside the Chloroplast Are Independent Processes," *The Plant Cell*, May 1990, pp. 479-494, vol. 2.
Igrejas, G., et al., "Genetic Analysis of the Size of Endosperm Starch Granules in a Mapped Segregating Wheat Population," *Journal of Cereal Science*, 2002, pp. 103-107, vol. 35.
Knutson, C.A., et al., "Variation in Enzyme Digestibility and Gelatinization Behavior of Corn Starch Granule Fractions," *Cereal Chem.*, 1982, pp. 512-515, vol. 59, No. 6.
Li, H-M., et al., "Information for Targeting to the Chloroplastic Inner Envelope Membrane is Contained in the Mature Region of the Maize Btl-encoded Protein,"*J. Biol. Chem.*, Sep. 15, 1992, pp. 18999-19004, vol. 267, No. 26.
Malinski, E., et al., "Isolation of Small Starch Granules and Determination of Their Fat Mimic Characteristics," *Cereal Chem.*, 2003, pp. 1-4, vol. 80, No. 1.
Mc Bride, K.E., et al., "Controlled Expression of Plastid Transgenes in Plants Based on a Nuclear DNA-encoded and Plastid-Targeted T7 RNA Polymerase," *Proc. Natl. Acad. Sci. USA*, Jul. 1994, pp. 7301-7305, vol. 91.

(Continued)

Primary Examiner—Russell P. Kallis
Assistant Examiner—Brent T Page
(74) Attorney, Agent, or Firm—Alston & Bird LLP

(57) ABSTRACT

The invention alters the physical characteristics of starch granules in a plant. Methods are provided for reducing starch granule size by stably introducing into the genome of the plant or plant cell a DNA construct comprising a polynucleotide encoding a polypeptide operably linked to a promoter that drives expression in a plant and operably linked to a plastid transit peptide. Compositions of the invention include transgenic plants and seeds having a reduced starch granule size. Compositions also include starch isolated from these plants and seeds. The modified starch granules find use in a wide range of food, feed, and industrial applications.

19 Claims, 7 Drawing Sheets

OTHER PUBLICATIONS

Morell, M.K., et al., "The Biochemistry and Molecular Biology of Starch Synthesis in Cereals," *Aust. J. Plant Physiol.*, 1995, pp. 647-660, vol. 22.

Peterson, D.G., and Fulcher, R.G., "Variation in Minnesota HRS Wheats: Starch Granule Size Distribution," *Food Research International*, 2001, pp. 357-363, vol. 34.

Raeker, M.O., et al., "Granule Size Distribution and Chemical Composition of Starches from 12 Soft Wheat Cultivars," *Cereal Chem.*, 1998, pp. 721-728, vol. 75, No. 5.

Shannon, J.C., et al., "Brittle-1, an Adenylate Translocator, Facilitates Transfer of Extraplastidial Synthesized ADP-Glucose into Amyloplasts of Maize Endosperms," *Plant Physiol.*, 1998, pp. 1235-1252, vol. 117.

Shewry, P.R., and Halford, N.G., "Cereal Seed Storage Proteins: Structures, Properties and Role in Grain Utilization," *Journal of Experimental Botany*, Apr. 2002, pp. 947-958, vol. 53, No. 370.

Stoddard, F.L., "Genetics of Wheat Starch B-granule Content," *Euphytica*, 2000, pp. 23-31, vol. 112.

Sullivan, T.D., et al., "Analysis of Maize Brittle-1 Alleles and a Defective Suppressor-Mutator-Induced Mutable Allele," *The Plant Cell*, Dec. 1991, pp. 1337-1348, vol. 3.

Takeda, Y., et al., "Structures of Large, Medium and Small Starch Granules of Barley Grain," *Carbohydrate Polymers*, 1999, pp. 109-114, vol. 38.

Tang, H., et al., "Physicochemical Properties and Structure of Large, medium and Small Granule Starches in Fractions of Normal Barley Endosperm," *Carbohydrate Research*, 2001, pp. 241-248, vol. 330.

Wilson, J.A., et al., "Genetic Effects of the Soft Starch (h) and Background Loci on vol. of Starch Granule sin Five Inbreds of Maize," *Plant Breeding*, 2000, pp. 173-176, vol. 119.

Wilson, J.A., et al., "Effect of Dosage of the Soft Starch (h) Locus on Starch Granule Volume in Maize," *Plant Breeding*, 2000, pp. 177-178, vol. 119.

JI, Q., et al., "Reduction of Starch Granule Size by Expression of an Engineered Tandem Starch-binding Domain in Potato Plants," *Plant Biotechnology Journal*, 2004, pp. 251-260, vol. 2.

\* cited by examiner

```
p13436      -MADHHRGA--TGGGGGYGDLQRGGGMH----------GEAQQQQKQGAMMTALKAATAA   47
A29788      ------R------GGGGYGDLQRGGGMH----------GEAQQQQKQGAMMTALKAATAA   38
Q42980      -MADQHRG---VIGGGGYGD--RGG---------------QEQQEKQPFMMTALKTVTAA   39
S57779      MAAEHHRDRGVLGGGGAFADRSGQGGYG--GDH--------HDQQKQPAMMCALKAATAT   50
Q96543      -MADHHRDRGVLGGG-ALGERGSHGGYGYTGDHGGYGGDDEQHQQKQPVMMCALKAATAA   58
                 *      **  . .:    *                  ..*:**   ** ***:.**:

p13436      TFGGSMLVLSGLILAGTVIALTVATPVLVIFSPVLVPAAIALALMAAGFVTSGGLGVAAL  107
A29788      TFGGSMLVLSGLILAGTVIALTVATPVLVIFSPVLVPAAIALALMAAGFVTSGGLGVAAL   98
Q42980      TAGGSMLVLSGLILAGTVIALTVATPVLVIFSPVLVPAAIALALMAAGFVTSGGLGVAAL   99
S57779      AAG-SLLVLSGLILAGTVIALTVATPVLVIFSPVLVPAAIALALMSAGFVTSGGLGVAAL  109
Q96543      TAGGSMLVLSGLILAGTVIALTVATPVLVIFSPVLVPAAISMALMSAGFVTSGGLGVAAV  118
            : * *:***********************************:.***:*************:

p13436      SVFSWMYKYLTGKHPPAADQLDHAKARLASKARDVKDAAQHRIDQAQGS  156
A29788      SVFSWMYKYLTGKHPPGADQLDHAKARLASKARDIKDAAQHRIDQAQGS  147
Q42980      SVFSWMYKYLTGKHPPGADQLDHAKARLASKARDIKEAAQHRIDQAQAS  148
S57779      SVFSWMYKYLTGKHPPGADQLDHAKARLASKARDIKDAAQTRIDQAQGA  158
Q96543      SVFSWMYKYLAGKHPPGADQLDHAKARLASKARDIKDAAQIRVEQAQGA  167
            **********:*****.*****************:*** *::***.:
```

FIG. 1

```
AAF13168    -MAFIGSLPFIIQTKAESSVLLHDKNLQRSRFSVFPCRSQNSFNLAVSLSLSFKPVRATG  59
S61505      MMLSLGSDATVLPFHAKNLKFTPKLSTLNGDLAFSKGLGVGRLNCGSVRLNHKQHVRAVG  60
CAC59826    ------------------------------------------------------VVC    3
AAK81729    MSGAIASSPAATLFLAGSSSSSPRRRRSRVSGVWWHLYGGTGLRLHWERRGLVRDGAVVC  60
AAK64284    MAAAAVSSLLAPSGSCYSPGCHSCWGPGPGGGRRLPSPRRRPI-TAAARPTWAVPRR-SR  58
CURCUMA     MFSHLLSSPPAPP----PPGAASCR-LLHGGARPLG---------HSPLCWANPLCTSR  45

AAF13168    K---EGVSGDGSED-TLQATIEKSKKVLALQRDLLQKIAERRKLVSSIQS-SVGDHDTNK  114
S61505      KSFGADENGDGSEDDVVNATIEKSKRFLLCKGNLFNRLLKERNLVSSIDSDSIPGLEGNG  120
CAC59826    S-----ASAAGGEDGVAKAKAKSAG--------------SSKAVAMQGSTAKADHVEDS   43
AAK81729    S-----ASAAGGEDGVAKAKTKSAG--------------SSKAVAVQGSTAKADHVEDS  100
AAK64284    LEWGRVEAQNSGARTSCRAALQWLSSTARSHVNVGYG--SPLVFPGLTKPGSSRCLCVVG  116
CURCUMA     FMAGLSEVKKGSKITLKHIDHTGSARTMRFLNALYHG--QSADLVPINHRGKS-----SG   98
                              . .    .

AAF13168    TSHEQRENSLANSDN--TSTSDVNMHQQQNGPVLPSSYVHSTADEVSETASSAINRGHAK  172
S61505      VSYESSEKSLSRDSNPQKGLPAAAVLLKPNGGTVFSNYVRSKETETWAVSSVGINQGFDE  180
CAC59826    VSSPKSVKPAVAKQN----------------GEVVSRATKSDAPVPKPKVDPSVPASKAE   87
AAK81729    VSSPKYVKPAVAKQN----------------GEVVSRATKSDAPVSKPKVDPSVPASKAE  144
AAK64284    MVGNAG-NQVGDDSD--------------DGIKVTNEKLRAVIRKSKEVLEIHRNLLEKI  161
CURCUMA     AVGRSNINDIQEDSN-------------QDVDIADDSVAQTMEQSKKVLEMQRNLLQQI  144
              :       ..:            :  .                    .

AAF13168    DDKELEQHASPRTAFVKNSTKQFKEMDSEKLQTDEIPSFLSNTTDISTINEENSEHSNES  232
S61505      IEK-------KNDAVKASSKLHFNEQIKNKLYERPDTKDISSSIRTSSLKFENFEGANEP  233
CAC59826    ADG-------NAQAVESKAALDKKED---------------VGVAEPLEAKADAGGDA   123
AAK81729    ADG-------NAQAVESKAALDKKED---------------VGVAEPLEAKADAGGDA   180
AAK64284    SASERKK---ITSIIEDSSIYNEQDPFGQRDSSFYHLDEVPDDDEFSYDLQMYLDRHPDQ  218
CURCUMA     --------------IEKRNFSEETESY-----------VKKDENLGIYAEAYMQTSNNQ  178
                .            . . :                    .   :   :

AAF13168    TSPMVDIFESD-----------SMTEDMKPPPLAGDNVMNVILVAAECAPWSKTGGLGD  280
S61505      SSKEVANEAEN-----------FESGGEKPPPLAGTNVMNIILVSAECAPWSKTGGLGD  281
CAC59826    GAVSSADDSEN-----------KESG-----PLAGPNVMNVIVVASECSPFCKTGGLGD  166
AAK81729    GAVSSADDSEN-----------KESG-----PLAGPNVMNVIVVASECSPFCKTGGLGD  223
AAK64284    SEVVATQDYEAQLSQISEMGQSVAEGTSDDPSASASVDLINIILVAAECAPWSKTGGLGD  278
CURCUMA     QEAPP---------------EEGNLNSP-PLAGPNVMNIILVAAECAPWSKTGGLGD    219
             . *.  :::*:*:*::**:*:.*******

AAF13168    VAGSLPKALARRGHRVMVVAPRYGNYVEPQDTGVRKRYKVDGQDFEVSYFQAFIDGVDFV  340
S61505      VAGSLPKALARRGHRVMIVAPHYGNYAEAHDIGVRKRYKVAGQDMEVTYFHTYIDGVDIV  341
CAC59826    VVGALPKALARRGHRVMVVIPRYGEYAEAKDLGVRKRYRVAGQDSEVSYFHAFIDGVDFV  226
AAK81729    VVGALPKALARRGHRVMVVIPRYGEYAEAKDLGVRKRYRVAGQDSEVSYFHAFIDGVDFV  283
AAK64284    VAGALPKALARRGHRVMVVVPMYKNYAEPQQLGEPRRYQVAGQDMEVIYYHAYIDGVDFV  338
CURCUMA     VVGALPKALAKRGHRVMVVSPRYGNYPEPKEIGNLKRYKVDGQDMEIKYYHTYIDSVDFV  279
            *.*:******:******.:*  *   :*  *.::  *   :**:*  ***  *:  *:::**.**:*

AAF13168    FIDSPMFRHIGNDIYGGNRMDILKRMVLFCKAAVEVPWHVPCGGVCYGDGNLAFIANDWH  400
S61505      FIDSPIFRNLESNIYGGNRLDILRRMVLFCKAAVEVPWHVPCGGICYGDGNLVFIANDWH  401
CAC59826    FLEAPPFRHRHNDIYGGERFDVLKRMILFCKAAVEVPWFAPCGGSIYGDGNLVFIANDWH  286
AAK81729    FLEAPPFRHRHNDIYGGERFDVLKRMILFCKAAVEVPWFAPCGGSIYGDGNLVFIANDWH  343
AAK64284    FIDNPIFHHVENDIYGGDRTDILKRMVLLCKAAIEVPWYVPCGGYCYGDGNLVFLANDWH  398
CURCUMA     FIDSPIFRHIGNDIYGGNRVDILKRMVLFCKAAVEVPWHVPCGGFCYGDGNLVFIANDWH  339
            *::  *  *::    .:****:*:** ::**.**:*:****.****..****  ******.*:*****
```

FIG. 2A

```
AAF13168    TALLPVYLKAYYRDNGLMQYTRSVLVIHNIAHQGRGPSGDFSYVGLPEHYIDLFKLHDPI 460
S61505      TALLPVYLKAYYRDHGLMNYTRSVLVIHNIAHQGRGPVEDFNTVDLSGNYLDLFKMYDPV 461
CAC59826    TALLPVYLKAYYRDNGLMQYTRSVLVIHNIAHQGRGPVDDFATMDLPEHYIDHFRLYDPV 346
AAK81729    TALLPVCLKAYYRDNGLMQYTRSVLVIHNIAHQGRGPVDDFATMDLPEHYIDHFRLYDPV 403
AAK64284    TALLPVYLKAYYHDNGFMIYARSVLVIHNIAHQGRGPLDDFSYLDLPVDYMDLFKLYDPF 458
CURCUMA     TSLLPVYLKACFRDRGLMTYARCLLVIHNIAHQGRGPLDDFSYVDLPHDHIDSFRLDDPV 399
            *:****  ***  ::*.*:*  *:*.:**************   **    :.*. ..::* *:: **.

AAF13168    GGDHFNIFAPGLKVADRVVTVSHGYAWELKTSEGGWGLHNIINENHWKLQGIVNGIDAKE 520
S61505      GGEHFNIFAAGLKTADRIVTVSHGYAWELKTSEGGWGLHNIINESDWKFRGIVNGVDTKD 521
CAC59826    GGEHSNVFAAGLKMADRAVTVSHGYLWEIKTMDGGWGLHEIINHNDWKLQGIVNGIDMAE 406
AAK81729    GGEHSNVFAAGLKMADRAVTVSHGYLWEIKTMDGGWGLHEIINHNDWKLQGIVNGIDMAE 463
AAK64284    GGDHLNIFAAGIKAADRLLTVSHGYAWELKTAEGGWGLHGIINESDWKFQGIVNGIDTTD 518
CURCUMA     GGEHFNIFAAGIRAADRVVTVSHGYAWELKTSEGGWGLHEIINECHWKFHGIVNGIDTHS 459
            **:*  *:**.*:: ***  :******  **:**  :****** ***.  .**:*****:*    .

AAF13168    WNPQFDIQLTSDGYTNYSLETLDTGKPQCKTALQNELRFAIPPDVPVIGFIGRLDYQKGV 580
S61505      WNPQFDAYLTSDGYTNYNLKTLQTGKRQCKAALQRELGLPVREDVPIISFIGRLDHQKGV 581
CAC59826    WNPEVDEHLQSDGYANYTFETLDTGKKQCKEALQRQLGLQVRDDVPLIGFIGRLDHQKGV 466
AAK81729    WNPEVDEHLQSDGYANYTFETLDTGKKQCKEALQRQLGLQVRDDVPLIGFIGRLDHQKGV 523
AAK64284    WNPRCDIHLKSDGYTNYSLETVQAGKQQCKAALQKELGLPVRGDVPVIAFIGRLDHQKGV 578
CURCUMA     WNPKFDAHLNSDGYTNFTLETLEMGKAQCKAALQREFGLPVRDDVPILAFIGRLDHQKGI 519
            ***. *   * ****:*:.::*::  ** *** ***.::  :  :   ***:: ******:***:

AAF13168    DLIAEAIPWMVGQDVQLVMLGTGRQDLEEMLRQFENQHRDKVRGWVGFSVKTAHRITAGA 640
S61505      DLIAEAIPWMMSHDVQLVMLGTGRADLEQMLKEFEAQHCDKIRSWVGFSVKMAHRITAGS 641
CAC59826    DIIGDAMPWIAGQDVQVVMLGTGRPDLEEMLRRFESEHNDKVRGWVGFSVQLAHRITAGA 526
AAK81729    DIIGDAMPWIAGQDVQVVMLGTGRPDLEEMLRRFESEHNDKVRGWVGFSVQLAHRITAGA 583
AAK64284    DLIAEAMPWIAGQDVQVQLIMLGTGRQDLEDTLRRLESQHYDRVRGWVGFSIRLAHRMTAGA 638
CURCUMA     DLIAEAMHWLVGQDLQIIMLGTGRPDLEDMLRRFEREHRGKVRGWVGFSVKMAHRITAGA 579
            *:*.:*:  *:   .:*:*:*******  ***: *:..* :*  .::*.*****:: ***:***:

AAF13168    DILLMPSRFEPCGLNQLYAMMYGTIPVVHAVGGLRDTVQPFDPFNESGLGWTFDSAESHK 700
S61505      DILLMPSRFEPCGLNQLYAMSYGTVPVVHGVGGLRDTVQPFNPFDESGVGWTFDRAEANK 701
CAC59826    DVLLMPSRFEPCGLNQLYAMAYGTVPVVHAVGGLRDTVAPFDPFADTGLGWTFDRAEANR 586
AAK81729    DVLLMPSRFEPCGLNQLYAMAYSTVPVVHAVGGLRDTVAPFDPFADTGLGWTFDRAEANR 643
AAK64284    DILLMPSRFEPCGLNQLYAMMYGTVPVVHAVGGLRDTVEHYNPYEESGLGWTFEKAEANR 698
CURCUMA     DALLMPSRFEPCGLNQLHAMMYGTIPVVHAVGGLRDTVQFDPFNETGLGWTFDRAEAHR 639
            *  *************:** *.*:****.********    ::*:   ::*:****: **:::

AAF13168    LIHALGNCLLTYREYKKSWEGLQRRGMTPNLSWDHAAEKYEETLVAAKYQW 751
S61505      LMAALWNCLLTYKDYKKSWEGIQERGMSQDLSWDNAAQQYEEVLVAAKYQW 752
CAC59826    MIDALGHCLNTYRNYKESWRGLQARGMAQDLSWDHAAELYEDVLVKAKYQW 637
AAK81729    MIDALGHCLNTYRNYKESWRGLQARGMAQDLSWDHAAELYEDVLVKAKYQW 694
AAK64284    LIDALGHCLNTYRNYRTSWEGLQKRGMMQDLSWDNAAKLYEEVLLAAKYQW 749
CURCUMA     MIVALGHCLNTYRNYKESWVGLQKRGMMQDLSWESAAEHYEKVLVAAKYQW 690
            ::  **  :**  **::*: **  *:*  ***  ;***:  **: **..*: *****
```

FIG. 2B

```
BAC57988    MVLCAMEAVGALTGGICASAAASSSSSSHVGLRRVVNSTSSASVVADCGRRRDLDQEKLK
T51090      ------------------MALLGSRSGLVGLRVSSRVGGESSRIVPATR-----------
CAD99148    ------------------------------------------------------------
CAD99146    ------------------------------------------------------------
CAB89288    --------------MATCTSAVFMPPDT------RRSRGVLTLLG---------------
JC7770      --------------MATYVSPCFTPSDSRLLTVLRKNVLPENHLG---------------
AAK63846    --------------MAAYVSPCLTPPDSRVLTVLRKSVLPDHHLG---------------

BAC57988    GVAEELGCHRSSLWAAAAAGETSVRGIRKSRAVRAVSRSNWESLRKVSALASQWGSESSV
T51090      -------------------------------DRFCVHLRPSTRAHRRLDRTVGNESLCTPRE
CAD99148    ------------------------------------------------------------
CAD99146    ------------------------------------------------------------
CAB89288    --------------GRLCALKMQDEKIGFLGVNQKGSSSLPQFKCSSNSHSVNQYQNKDS
JC7770      --------------RLNSIRTIDS--KKNRVVVAAQKSESSPIR---NSPRHYQSQAQDP
AAK63846    --------------TRVGCLRMSEGTTKRYRVVASHKYESSSIRNSLNSHSTSHFQSQDS

BAC57988    EWQEDEYQYTRPGNGSLTASKAGGGGSPLPSASSWQGAPPIQSFNEAKIKVIGVGGGGSN
T51090      RDLAAEPKFLHTGWESSSSSSSSSCETGIPVTAFGGNGDEYESSNEAKIKVIGVGGGGSN
CAD99148    ------------------------------------------------------------
CAD99146    ---------------------------------------------------------GSN
CAB89288    FLNLHPEISLLRG-----------EESSSGNVTESLMDSSRSNNFNEAKIKVVGVGGGGSN
JC7770      FLNLHPEISMLRGEGTSTIVNPRKETSSGPVVEDFEEPSAPSNYNEARIKVIGVGGGGSN
AAK63846    FLNLHPEISMLN---------PRKETSSVPITEDLDELSTPNTYNEARIKVIGVGGGGSN

BAC57988    AVNRMLQSEMKGVEFWIVNTDSQAMAMSPVQEENRLQIGQKLTRGLGAGGNPEIGMSAAE
T51090      AVNRMLESEMQGVEFWIVNTDAQAMALSPVPAQNRLQIGQKLTRGLGAGGNPEIGCSAAE
CAD99148    --------AGSGVEFWIVNTDVQAIRMSPVHSQNRLQIGQELTRGLGAGGNPDIGMNAAK
CAD99146    AVNXMIESSMNGVEFWIVNTDIQAIRMSPVFPENRLPIGQELTRGLGAGGNPDIGMNAAK
CAB89288    AVNRMIESSMKGVEFWIVNTDIQAMRMSPVAAEQRLPIGQELTRGLGAGGNPDIGMNAAN
JC7770      AVNRMIESEMSGVEFWIVNTDIQAMRMSPVLPDNRLQIGKELTRGLGAGGNPEIGMNAAR
AAK63846    AVNRMIESEMIGVEFWIVNTDIQAMRISPVFPDNRLQIGKELTRGLGAGGNPEIGMNAAT
                    ********** **: :***   ::** **::***********:** .**

BAC57988    ESKALVEEALRGADMVFVTAGMGGGTGSGAAPVIAGVAKALGILTVGIVTTPFSFEGRRR
T51090      ESKAMVEEALRGADMVFVTAGMGGGTGSGAAPIIAGVAKQLGILTVGIVTTPFAFEGRRR
CAD99148    ESCESIEEALHGADMVFVTAGMGGGTGTGGAPVIAGIAKSMXILTVGIVTTPFSFEGRRR
CAD99146    ESKEAIEEAVXGADMVFVTAGMGGGTGTGGAPIIAGIAKSMGILTVGIVTTPFSFEGRRR
CAB89288    ESKQAIEEAVYGADMVFVTAGMGGGTGTGAAPIIAGTAKSMGILTVGIVTTPFSFEGRRR
JC7770      ESKEVIEEALYGSDMVFVTAGMGGGTGTGAAPVIAGIAKAMGILTVGIATTPFSFEGRRR
AAK63846    ESKEAIQEALYGSDMVFVTAGMGGGTGTGGAPIIAGVAKAMGILTVGIVTTPFSFEGRRR
            **   ::**: *:**************:*.**.*** **  : ******.****:*****
```

FIG. 3A

```
BAC57988    SVQAQEGIAALRNNVDTLIIIPNDKLLTAVSQSTPVTEAFNLADDILRQGVRGISDIITV
T51090      SVQAHEGIAALKNNVDTLITIPNNKLLTAVAQSTPVTEAFNLADDILRQGVRGISDIITV
CAD99148    AVQAQEGTSALRNSVDTLIVIPNDKLLSAVSPNTPVTEAFNLADDILWQGIRGISDIITV
CAD99146    AVQAQEGIAALRENVDTLIVIPNDKLLTXVSLSTPVTEAFNLADDILRQGVRGISDIITI
CAB89288    AVQAQEGIAALRENVDTLIVIPNDKLLTAVSPSTPVTEAFNLADDILRQGVRGISDIITI
JC7770      TVQAQEGLASLRDNVDTLIVIPNDKLLTAVSQSTPVTEAFNLADDILRQGVRGISDIITI
AAK63846    ALQAQEGIAALRDNVDTLIVIPNDKLLAAVSQSTPVTEAFNLADDILRQGVRGISDIITI
            ::**:**  ::*::.***** ***:***: *: .************** **:********:

BAC57988    PGLVNVDFADVRAIMADAGSSLMGIGTATGKSRARDAALSAIQSPLLDVGIERATGIVWN
T51090      PGLVNVDFADVRAIMANAGSSLMGIGTATGKSKAREAALSAIQSPLLDVGIERATGIVWN
CAD99148    PGLVNVDFADVXAIMQNAGSSXMGIGTATGKSRARDAALNAIQSPLLDIGIERATGIVWN
CAD99146    PGLVNVDFADVRAIMANAGSSLMGIGTATGKTRARDAALNAVQSPLLDIGIERATGIVWN
CAB89288    PGLVNVDFADVRAIMANAGSSLMGIGTATGKTRARDAALNAIQSPLLDIGIERATGIVWN
JC7770      PGLVNVDFADVRAIMANAGSSLMGIGTATGKSRARDAALNAIQSPLLDIGIERATGIVWN
AAK63846    PGLVNVDFADVRAIMANAGSSLMGIGTATGKTRARDAALNAIQSPLLDIGIERATGIVWN
            ***********.***.:****.**********:.**:***.**:*****.*:***********

BAC57988    ITGGSDMTLFEVNAAAEVIYDLVDPNANLIFGAVVDESYTGEVSITLIATGFRGQDDSEL
T51090      ITGGSDMTLFEVNAAAEVIYDLVDPNANLIFGAVVDEALHDQISITLIATGFSSQDDPDA
CAD99148    ITGGNDLTLFEVNAAAAEVIYDPRA-----------------------------------
CAD99146    ITGGNXLTLFEVNAAAEVIYDLVDPSANLIFGAD--------------------------
CAB89288    ITGGSDLTLFEVNAAAEVIYDLVDPSANLIFGAVIDPSISGQVSITLIATGFKRQEESDG
JC7770      ITGGSDLTLFEVNAAAEVIYDLVDPTANLIFGAVVDPALSGQVSITLIATGFKRQEEGEG
AAK63846    ITGGSDLTLFEVNAAAEVIYDLVDPTANLIFGAVVDPSYSGQISITLIATGFKRQEEGEG
            ****. :*********                    :     .   -

BAC57988    RSVQQTGRSMDGDHGRRPSGVPPLSGSNGSTVDIPSFLKRRGRSRYPRVG
T51090      RSMQYASRVLEGQAGR--SSMASSRGGNSSTINIPNFLRKRGQR------
CAD99148    --------------------------------------------------
CAD99146    --------------------------------------------------
CAB89288    RPLQGN--QLTQGDVSLGNNRRPASFLEGGSVEIPEFLRKKGRSRYPRA-
JC7770      RTVQMV--QADAASVGATR-RPSSSFRESGSVEIPEFLKKKGSSRYPRV-
AAK63846    RPLQAT--QADAS-MGATR-RPSSSFTEGSSIEIPEFLKKKGRSRYPRL-
```

FIG. 3B

```
AAK50084      1 ................................MGKTGIQLFDDSRNGFF  17
                                                ||||    |   |   |
ZM-Bt1        1 MAATMAVTTMVTRSKESWSSLQVPAVAFPWKPRGGKTGGLEF..PRRAMF  48

AAK50084     18 SVSDLGFDSSLNSSN..YHPIGGLFASVNQTNPFASLSSSDLSNR..GNN  63
                  .  |    ..       |    . . .      |||.      .| |
ZM-Bt1       49 ASVGLNVCPGVPAGRDPREPDPKVVRAADNCDIAASLAPPFPGSRPPGRR  98

AAK50084     64 SFSTQLNDLYTKYMPGKEEEEEVVNGEKRKRKKKGGLTLKIKIANPSLRR 113
                 .:    :        |:  ||       |   ..|    .|. |
ZM-Bt1       99 GRGSEEEE.....AEGRRHEEAAAAGRSEPEEGQG......QDRQPAPAR 137

AAK50084    114 LLSGAVAGAVSRTVVAPLETIRTHLMVGS.GGNSSTEVFSDIMKHEGWTG 162
                |.|||:||||||| |||||||||||||||  .|   ||   ||..|||||
ZM-Bt1      138 LVSGAIAGAVSRTFVAPLETIRTHLMVGSIGVDSMAGVFQWIMQNEGWTG 187

AAK50084    163 LFRGNLVNVIRVAPARAVELFVFETVNKKLSPPHGQESKIPIPASLLAGA 212
                |||||  |||:||||..:|: |  ::|   | |.|   :  |||||  |.||
ZM-Bt1      188 LFRGNAVNVLRVAPSKAIEHFTYDTAKKFLTPKGDEPPKIPIPTPLVAGA 237

AAK50084    213 CAGVSQTLLTYPLELVKTRLTIQRGVYKGIFDAFLKIIREEGPTELYRGL 262
                ||  . || |||:||:|||.||::  ||   :   ||.||:|:|||.||||||
ZM-Bt1      238 LAGFASTLCTYPMELIKTRVTIEKDVYDNVAHAFVKILRDEGPSELYRGL 287

AAK50084    263 APSLIGVVPYAATNYFAYDSLRKAYRSFSKQE...KIGNIETLLIGSLAG 309
                ||||||||||||  |:||:.|::  ||  . .        :|  :  |||||| ||
ZM-Bt1      288 TPSLIGVVPYAACNFYAYETLKRLYRRATGRRPGADVGPVATLLIGSAAG 337

AAK50084    310 ALSSTATFPLEVARKHMQVGAVSGRVVYKNMLHALVTILEHEGILGWYKG 359
                |:.|.|||||||||| |||||| ||  ||.|.|||:   ||. ||   | |:|
ZM-Bt1      338 AIASSATFPLEVARKQMQVGAVGGRQVYQNVLHAIYCILKKEGAGGLYRG 387

AAK50084    360 LGPSCLKLVPAAGISFMCYEACKKILIENNQEA................ 392
                |||||:||.||||||.||||||||||||||||::       |
ZM-Bt1      388 LGPSCIKLMPAAGIAFMCYEACKKILVDKEDEEEEDEAGGGEDDKKKVE  436
```

FIG. 4

PRODUCTION OF CEREAL GRAIN WITH REDUCED STARCH GRANULE SIZE AND USES THEREOF

CROSS-REFERENCE TO RELATED APPLICATIONS

This application claims the benefit of U.S. Provisional Application Ser. No. 60/533,762, filed Dec. 31, 2003, the contents of which are hereby incorporated in their entirety by reference herein.

FIELD OF THE INVENTION

The invention relates to the production of modified starch granules in plants. Specifically, the starch granules have a reduced size, which may find utility in numerous feed and industrial applications.

BACKGROUND OF THE INVENTION

Starch is a complex polymer of glucosyl residues and is the major storage form for carbohydrates in higher plants. It is used to supply the needs of the plant for energy and biosynthesis when photosynthesis is not occurring. Starch accumulates in the chloroplasts of photosynthetic cells, as well as in amyloplasts present in storage organs such as seeds, fruit and tubers.

Starch is a mixture of two polysaccharides: amylose, which is a linear chain of glucosyl units linked by alpha-1, 4-glycosidic bonds; and amylopectin, which is made up of many linear chains of alpha-1,4-polyglucans which are joined together by alpha-1,6 glycosidic bonds. The amylose/amylopectin ratio varies between plants and can affect the physical properties of starch, such as gelatinization temperature, retrogradation and viscosity.

Many plants with altered starch granules have been identified, and particular applications utilizing starch having these alterations have been recognized. Starch with no amylose (all amylopectin) is called "waxy" starch. Waxy starch, once gelatinized, is more rapidly digested than normal starch (70-75% amylopectin, 25-30% amylose). Waxy starches are useful as thickeners or gel-forming agents because they form a clear stable gel with little retrogradation (Morell et al. (1995) *Aust. J. Plant Physiol.* 22:647-660). High amylose (70%) starch forms insoluble aggregations, is more slowly digested, and therefore is suited for use in formulating adhesives, plastics and as a source of dietary fiber (Whistler R. L. (1984) "Starch" (Eds. R. L. Whistler, J. N. BeMiller and E. F. Paschall) Academic Press: Orlando; Doane (1994) *Cereal Foods World* 39:556-563). Boyer et al. showed that the increased proportion of larger granules in developing kernels of various genotypes (normal, ae, and ae su) is related to a higher amylose percentage, whereas in late development a decrease in amylose percentage results in a decrease in granule size (Boyer et al. (1976) *Cereal Chemistry* 53:327-337). The soft starch (h) gene increases starch granule size compared with normal genotypes, and results in a loose packing of starch granules (Gutiérrez et al. (2002) *Crop Sci.* 42:355-359).

The size and branching patterns of starch molecules also affects physical properties of starch, such as the gelatinization temperature, starch swelling and viscosity. In maize kernels, the sugaryl mutation causes the absence of a debranching enzyme which hydrolyzes alpha-1,6-glycosyl linkages of starch (James et al. (1995) *Plant Cell* 7:417-429). The mutation results in a decreased concentration of amylopectin and accumulation of the highly branched glucopolysaccharide phytoglycogen, and produces several advantageous physical characteristics of starch. For example, the accumulation of phytoglycogen in su1 mutants is associated with smaller and more numerous starch granules (Wang et al. (1993) *Cereal Chem.* 70:171-179; Brown et al. (1971) *Crop Sci.* 11:297-302). In addition, starch from sugaryl mutant endosperm containing a high phytoglycogen content has a reduced temperature of gelatinization compared to that of waxy or normal starch (Wang et al. (1992) *Cereal Chem.* 69:328-334). The reduced gelatinization temperature increases starch solubility after processing (grinding, pelleting, steam flaking) at temperatures below the gelatinization temperature of normal starch. The smaller granule size and reduced temperature of gelatinization may both contribute to the high digestibility of starch from sugaryl mutant corn. See, for example, Fuwa et al. (1979) *J. Nutr. Sci. Vitaminol.* 25:103-114 and Fuwa et al. (1979) *Cereal Chem* 54:230-237 and Ninomya et al. (1989) *Starch* 41:165-167.

Granule size is important in the manufacturing of degradable plastic films, carbonless copy paper, dusting powder, baking powder, laundry-stiffening agents, and utilization of small granules as a fat substitute (Gutiérrez et al. (2002) *Crop Sci.* 42:355-359). Starch is a major source of carbohydrates for both man and livestock through crops such as wheat, maize, rice and potatoes. Starch is also used industrially in the production of paper, textiles, plastics, adhesives, and provides the raw material for some bioreactors. The type of starch affects the quality of the final product and therefore its profitability. Therefore, methods are needed to modify starch, particularly starch granule size, for use in various industrial applications. One example of an industrial application that may benefit from the use of grain with small starch granules is the corn dry-grind ethanol industry, in which starch of the grain is hydrolyzed to glucose for fermentation into ethanol. Grain with smaller-than-normal starch granules may be hydrolyzed at a lower cost by the α-amylase and glucoamylase enzymes used normally, because smaller starch granules have a larger surface area and would be "attacked" by α-amylase more efficiently (for example, in a quicker fashion, or with reduced amount of enzyme required) than with starch from a normal genetic background.

SUMMARY OF INVENTION

Methods and compositions are provided for modifying properties of starch granules in plants. Specifically, a method is provided for reducing starch granule size in a plant. The method comprises stably introducing into the genome of the plant or plant cell a DNA construct comprising a polynucleotide encoding a polypeptide of interest operably linked to a promoter that drives expression in a plant and operably linked to a plastid transit peptide. Expression of proteins that are natively plastid-associated and proteins that are not natively plastid-associated but which are targeted to a plant plastid with a plastid transit peptide result in the biosynthesis of starch granules with reduced size. The methods of the invention find use in reducing starch granule size, increasing the digestibility of starch, and in altering the physical properties of starch, including thermal stabilization, retrogradation, gelatinization temperature, water affinity, starch pasting, kernel texture, gel hardness, stickiness, and viscosity.

Compositions of the invention include an expression cassette or a DNA construct comprising a polynucleotide operably linked to a promoter that drives expression in a plant and operably linked to a plastid transit peptide, wherein the polynucleotide encodes a polypeptide of interest or fragment thereof. Compositions of the invention further include genetically modified plants having stably incorporated into their genome a heterologous polynucleotide operably linked to a plastid transit peptide, as well as transformed seed from the plant. Compositions further comprise the modified starch, which is useful as a food additive and in industrial applications, such as those previously mentioned.

BRIEF DESCRIPTION OF THE DRAWINGS

FIG. 1 shows an alignment of an oleosin protein sequence from maize (Ole16) (NCBI Accession No. P13436) (SEQ ID NO:16), a cDNA fragment of the L3 lipid body-associated major protein of maize (NCBI Accession No. A29788) (SEQ ID NO:23), a 16 kD oleosin from *Oryza sativa* (NCBI Accession No.Q42980) (SEQ ID NO:24), oleosin 2 from barley (*Hordeum vulgare*) (NCBI Accession No.S57779) (SEQ ID NO:25), and a 16 kD oleosin from *Bromus secalinus* (NCBI Accession No. Q96543) (SEQ ID NO:26).

FIGS. 2A and 2B show an alignment of starch synthase protein sequences from cassava (NCBI Accession No. AAF13168) (SEQ ID NO:27), pea (NCBI Accession No. S61505) (SEQ ID NO:28), rice (NCBI Accession Nos. CAC59826; AAK81729; and AAK64284) (SEQ ID NOS: 29, 30, and 31), and *Curcuma zedoria* (SEQ ID NO:2).

FIGS. 3A and 3B show an alignment of FtsZ2 protein sequences from liverwort (NCBI Accession No. BAC57988) (SEQ ID NO:32), moss (NCBI Accession No. T51090) (SEQ ID NO:33), bread wheat (NCBI Accession No. CAD99148) (SEQ ID NO:34), potato (NCBI Accession No. CAD99146) (SEQ ID NO:35), tobacco (NCBI Accession No. CAB89288) (SEQ ID NO:36), and *Arabidopsis thaliana* (NCBI Accession Nos. JC7770 and AAK63846) (SEQ ID NOS:37 and 38).

FIG. 4 shows an alignment of *Arabidopsis* mitochondrial carrier protein family (NCBI Accession No. AAK50084) (SEQ ID NO:21) to *Zea mays* Brittle-1 protein (ZM-Bt1) (SEQ ID NO:8).

DETAILED DESCRIPTION OF THE INVENTION

Figure 5:
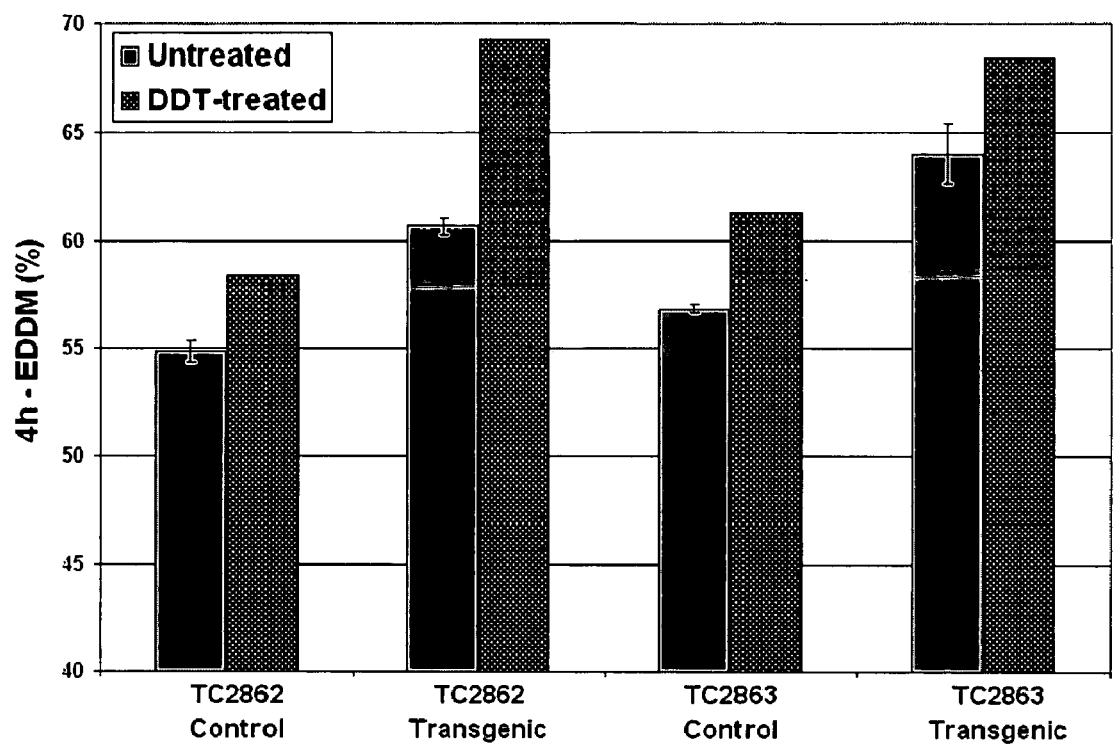
FIG. 5 shows that overexpression of Brittle-1 improves the digestibility of grain. Grain was tested for in vitro digestibility by analyzing within-row segregating ears of maize that were either wild-type or carrying the transgene. Significantly increased Enzyme Digestible Dry Matter (EDDM) was observed after 4 hours of treatment.

Compositions and methods are provided for the production of modified starch granules, which are useful in a wide range of food and industrial applications. Specifically, the starch granule size is reduced when compared to unmodified starch granules. By "starch" is intended a complex granular structure composed of polyglucan chains comprising amylopectin and amylose. By "polyglucan" is intended any polyglucan structure comprising glucose molecules connected by α1-4 glycosidic bonds or α1-4 and α1-6 glycosidic bonds. Characteristics of amylopectin include a high molecular weight ($10^7$-$10^9$ Da) and a polyglucan chain containing approximately 5% α-1,6 branches. Amylose is a smaller linear molecule (molecular weight of $10^5$-$10^6$ Da) and contains very few α-1,6 branches (less than 1%) (Ball et al. (1996) *Cell* 86:349-352). The characteristics of amylose and amylopectin are further described in Nakamura et al. (1996) *Plant Science* 121:1-18 and in Helt et al. (1997) *Plant Biochemistry and Molecular Biology*, Oxford University Press, both of which are herein incorporated by reference.

Methods of the present invention comprise stably introducing into the genome of a plant a DNA construct comprising a polynucleotide of interest operably linked to a promoter that drives expression in a plant and operably linked to a plastid transit peptide, wherein the polynucleotide encodes a polypeptide or fragment thereof. The polypeptide of interest is thereby targeted to a plastid. The method of the invention increases the level of a polypeptide, or fragment thereof, in a plastid and thereby reduces starch granule size when compared to an unmodified plant. The polypeptide employed in this method may comprise a protein that is natively associated with a plant plastid or a protein operably linked to a heterologous plastid transit peptide. By "reduced" size of the starch granule is intended at least about 10%, at least about 12%, at least about 15%, at least about 20%, at least about 25%, and at least about 45% decrease in granule size compared to unmodified plants. Methods for measuring granule size are well known in the art (see, for example, Evers (1973) *Starch* 9:303-304; Evers and Lindley (1977) *Journal of the Science of Food and Agriculture* 28:98-102; Stark and Lynn (1992) *Biochemical Society Transactions* 20:7-12; Bechtel et al. (1990) *Cereal Chemisty* 67:59-63; Stoddard (2003) *Aust. J. Agric. Res.* 54:637-648).

The plants, plant cells, seeds, and plant tissues are "modified" in that they comprise one or more polynucleotides that, when expressed, lead to alteration of the physical properties of the starch granules. As noted below, various methods are available for creating modified plants, plant cells, and plant tissues including, but not limited to, transformation, transfection and breeding. Such techniques will lead to altered expression and targeting of proteins in the modified plant, plant cell, seed, or tissue.

It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

By "plastid transit peptide" is intended an N-terminal sequence of about 30-100 amino acids that targets proteins into plastid organelles. After protein translocation, the transit peptides are removed by proteolytic cleavage. Transit peptides target precursor proteins from the cytosol into plastids, such as chloroplasts and amyloplasts. Proteins targeted to chloroplasts may also contain domains with intraorganellar information, resulting in transport of the protein across the thylakoid membrane and into the lumen (Ko and Cashmore (1989) *EMBO J.* 8:3187-3194; Meadows et al. (1989) *FEBS Lett.* 253:244-246; Hageman et al. (1990) *Plant Cell* 2:479-494). Plastids of different plant tissues are able to import foreign proteins, indicating that plastids may have similar or identical protein import mechanisms (Weisbeek et al. (1989) *J. Cell Sci. Suppl.* 11:199-223). Many studies have shown that chloroplast transit peptides can effectively target proteins to other plastid types. The amyloplast transit peptide of the waxy protein of maize can direct the import of an artificial preprotein consisting of the waxy transit peptide and the first 34 amino acids of the mature waxy protein fused in-frame to the beta-glucuronidase of *E. coli* into chloroplasts (Klosgen et al. (1989) *Mol. Gen. Genet.* 217:155-161; Klosgen and Weil (1991) *Mol. Gen. Genet.* 225:297-304). Conversely, the chloroplast ribulose-1,5-bisphosphate carboxylase precursor proteins are targeted to leucoplasts (Boyle et al. (1986) *Plant Physiol.* 81:817-822; Halpin et al. (1989) *FEBS Lett.* 258:32-34), etioplasts (Schindler and Soll (1986) *Arch. Biochem. Biophys.* 247:211-220), and amyloplasts (Strzalka et al. (1987) *Biochem. Biophys. Res. Commun.* 149:799-806). Therefore, the protein import mechanism of plants is able to recognize different types of transit peptides regardless of the protein being transported. This is to be expected, as all plastid types are derived from proplastids (Wan et al. (1996) *J. Biol. Chem.* 271:31227-31233).

Transit peptides for use in the present invention are known in the art and include, but are not limited to, those from Brittle-1 (SEQ ID NO:10); *Curcuma* soluble starch synthase (SEQ ID NO:4); chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6):789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36):27447-27457); the light harvesting chlorophyll a/b binding protein (LHBP) (Lamppa et al. (1988) *J. Biol. Chem.* 263:14996-14999), the transit peptide for the plant plastid acyl carrier protein (ACP), the transit peptide for GBSSI (granule bound starch synthase I) and the native transit peptide of a targeting protein. See also Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481. Other examples of transit peptides include the transit peptides described in U.S. Publication No. US 2002/0073443 and U.S. Publication No. US 2002/0178467. Combinations of transit peptides may also be used. Such transit peptides are known in the art. See, for example, U.S. Publication No. US 2002/0178467. Each of these references is hereby incorporated in its entirety by reference herein.

It is recognized that synthetic or variant transit peptides may be utilized. In this regard, three major blocks of amino acid homology have been found in transit peptides of two chloroplast proteins (Karlin-Neumann and Tobin (1986) *EMBO J.* 5:9-13). Functional domains of the ferredoxin transit peptide have also been identified (Pilon et al. (1995) *J. Cell Biol.* 270:3882-3893; Rensink et al. (1998) *Plant Physiol.* 118: 691-699). Conserved cleavage-site motifs in chloroplast or mitochondrial targeting proteins have been identified (Gavel et al. (1990) *FEBS Lett.* 261:455-458; Gavel et al. (1990) *Protein Eng.* 4:33-37; Emanuelsson et al. (1999) *Protein Science* 8:978-984).

The polypeptide of interest may be one that is natively plastid-associated or may be one that is not natively plastid-associated but which is targeted to a plant plastid with a plastid transit peptide. In one embodiment, the polypeptide of interest is one that is involved in plastid division, such as FtsZ. In another embodiment, the polypeptide is involved in lipid storage, such as oleosin. By "lipid storage" or "lipid storage-related" is intended a polypeptide that associates with a lipid storage body in a plant, such as an oil body. In yet another embodiment, the polypeptide is involved in lipid synthesis. In another embodiment, the polypeptide is involved in amino acid metabolism. In still another embodiment, the polypeptide is a chloroplast-associated protein. By "chloroplast-associated" protein is intended a polypeptide that is natively expressed in a chloroplast or is targeted to the chloroplast. Methods for identifying chloroplast-associated proteins are well known in the art. See, for example, Wijk (2000) *Trends Plant Sci.* 5:420-425; Leister (2003) *Trends Genet.* 19:47-56), where the identification of coding regions of chloroplast proteins by experimental proteomic analysis is described. In another embodiment, the polypeptide of interest is a starch-related polypeptide. By "starch-related" is intended a polypeptide that is involved in the transport, synthesis, or regulation of starch, including, but not limited to, a plastid-associated polypeptide or an enzyme involved in starch synthesis.

By "plastid-associated polypeptide" is intended a polypeptide that is targeted to or expressed in a plastid, including those targeted to the outer envelope membrane, the inner envelope membrane, the intermembrane space, the stroma, the thylakoid membrane, and the thylakoid lumen of a plastid. By "plastid" is intended any plastidic organelle of a plant, including, but not limited to a proplastid, an etioplast, a chloroplast, a chromoplast, and a leucoplast. All plastids share certain features, including being enclosed by an envelope composed of two concentric membranes. Proplastids are the precursors of all plastid types and are present in the immature cells of plant meristems and cells of developing endosperm (Bechtel and Wilson (2003) *Cereal Chem.* 80:175-183). Etioplasts are present in plants that are grown in the dark, and contain a yellow chlorophyll precursor instead of chlorophyll. When exposed to the light, etioplasts develop into chloroplasts. Chloroplasts are specialized for photosynthesis and contain an internal thylakoid membrane system. Other plastids have two membranes, but lack the thylakoid membrane and other components of the photosynthetic apparatus. Chromoplasts lack chlorophyll, but contain carotenoids. Leucoplasts are nonpigmented and store a variety of energy sources in nonphotysynthetic tissues. One form of a leucoplast is an amyloplast, which accumulates starch in various tissues. Another form of leucoplast is an elaioplast, which functions in lipid storage. See Lodish et al. (2000) *Molecular Cell Biology* (4th ed. W. H. Freeman & Co., New York), for more information about plastids.

The coding sequence for any polypeptide may be used. Examples include, but are not limited to, Brittle-1, FtsZ, oleosin, and starch synthase. See the sequences set forth in SEQ ID NOS:2, 6, 8, 12, 14, and 16, or a fragment or variant thereof. In some embodiments, the polypeptide is an enzyme involved in starch synthesis, including, but not limited to, a phosphoglucomutase, an ADP glucose pyrophosphorylase, a soluble or granule-bound starch synthase, or a starch branching enzyme; the polypeptide may be involved in transport into or out of the plastid, or may be a debranching enzyme, such as an isoamylase or a pullulanase.

The maize Brittle-1 (Bt-1) locus was identified in 1926 by mutations that decreased the amount of starch produced in the endosperm (Mangelsdorf (1926) Conn. Agric. Exp. Stn. Bull. 279:509-614; Wentz (1926) J. Hered. 17:327-329). Bt-1 encodes a seed-specific, amyloplast membrane protein thought to transport ADP-glucose, the substrate of starch biosynthesis, into the plastid (Sullivan and Kaneko (1995) Planta 196:477-484; Sullivan et al. (1991) Plant Cell 3:1337-1348). Bt-1-encoded protein shows the greatest sequence similarity to Arabidopsis mitochondrial carrier protein family (i.e. 53% amino acid sequence identity). The NCBI Accession Number for maize Bt-1 is P29518. An alignment of maize Bt-1 (SEQ ID NO:6) with *Arabidopsis* mitochondrial carrier protein family (NCBI Accession No. AAK50084) (SEQ ID NO:15) is provided in FIG. 4. Bt-1 has a KTGGL (SEQ ID NO:16) motif (amino acid residues 36-40 of SEQ ID NO:6) common to the ADP-glucose-binding site of starch synthases and bacterial glycogen synthases (Shannon et al. (1998) Plant Physiol. 117:1235-1252). A variant of Bt-1, Bt1-m has been identified (NCBI Accession No. M79334) that has a transposable element inserted into it (Sullivan et al., supra). Methods to assay for solute transport into plastids are known in the art (see, for example, Shannon et al., supra.; Keegstra and Froehlich (1999) Curr. Opinion Plant Biol. 2:471-6). Each of these Accession Nos. is herein incorporated by reference.

Oleosin is an amphipathic protein normally found within the membrane of plants' lipid storage bodies called oil bodies. Expression occurs in tissues that produce storage lipids such as triacylglycerols. In maize, expression is typically very strong in scutellar and aleurone cells, while typically extremely low in endosperm cells. Oleosin is divided into three structural portions: an N-terminal amphipathic stretch of undefined secondary structures residing on the organelle surface (20-60 residues); a conserved central hydrophobic domain of beta-strand structure penetrating into the matrix (about 70 residues); and a C-terminal amphipathic-helix locating on the organelle surface, interacting with the phospholipid layer (60-100 residues). The three structural portions enable the protein to interact with other molecules on the surface of an oil body (Ting et al. (1997) J. Biol. Chem. 272:3699-3706). The most conserved region is the 13-amino acid residue turn separating the two antiparallel beta-strands (Huang (1996) Plant Physiol. 110: 1055-1061). Inside this region are three universally conserved proline residues, forming the "proline knot" motif. The loss of the proline knot results in instability of the oleosin during trafficking (Abell et al. (1997) Plant Cell 9:1481-1493).

The function of oleosin has not been fully characterized, but it is known to serve a structural role in stabilizing the lipid body. The long hydrophobic strands act as an anchor and penetrate into the matrix of triacylglycerols, and the cytosol-exposed regions interact with the surface lipids to generate additional stability. Oleosins form a steric barrier between adjacent oil bodies, preventing their coalescence (Huang (1996) Plant Physiol. 110:1055-1061). Oleosin may also act as recognition signals for specific binding of lipase to the lipid bodies, to facilitate lipolysis during germination (Vance and Huang (1987) J. Biol. Chem. 262:11275-11279; Huang (1996) Plant Physiol. 110:1055-1061).

The first oleosin gene, L3, was cloned from maize using in vitro translation and an anti-L3 antibody (Vance et al. (1987) J. Biol. Chem. 262:11275-11279). Numerous isoforms of oleosin genes from such different species as *Brassica*, soybean, carrot, pine, and *Arabidopsis* have been cloned (Huang, A. H. C. (1992) Ann. Reviews Plant Phys. and Plant Mol. Biol. 43:177-200; Kirik et al. (1996) Plant Mol. Biol. 31:413-417; Van Rooijen et al. (1992) Plant Mol. Biol. 18:1177-1179; Zou et al. (1996) Plant Mol. Biol. 31:429-433). An alignment of maize Ole16 (NCBI Accession No. P13436) (SEQ ID NO:16), a cDNA fragment of the L3 lipid body-associated major protein of maize (NCBI Accession No. A29788) (SEQ ID NO:23), a 16 kD oleosin from *Oryza sativa* (NCBI Accession No. Q42980) (SEQ ID NO:24), oleosin 2 from barley (*Hordeum vulgare*) (NCBI Accession No. S57779) (SEQ ID NO:25), and a 16 kD oleosin from *Bromus secalinus* (NCBI Accession No. Q96543) (SEQ ID NO:26) is provided in FIG. 1. Oleosin protein sequences predicted from these genes are highly conserved, especially for the central hydrophobic domain. Methods to determine the secondary structure and other protein characteristics of oleosin-like proteins are well known in the art (see, for example, Vance and Huang (1987) J. Biol. Chem. 262:11275-11279; Tzen et al. (1992) J. Biol. Chem. 267:15626-15634; Ting et al. (1997) Journal of Biological Chemistry 272:3699-3706; Ting and Huang (1997) "Oils-to-oleosins ratio determines the size and shape of oil bodies in maize kernels." Physiology, Biochemistry and Molecular Biology of Plant Lipids. J. P. Williams, M. U. Khan and N. W. Lem. PO Box 17/3300 AA Dordrecht/Netherlands, Kluwer Academic Publ:295-297).

Starch synthase transfers a glucose residue from ADP-glucose or, less commonly, UDP-glucose, to the OH-group in the 4-position of the terminal glucose molecule in the polysaccharide chain. The starch synthases are divided into three classes based on their subcellular location (soluble phase, granule fraction, or both). Several plant starch synthases are known in the art. Examples of granule-bound starch synthases include, but are not limited to, cassava (NCBI Accession No. AAF13168), pea (NCBI Accession No. S61505), potato (NCBI Accession No. Q43847), maize (NCBI Accession No. CAA27574), sorghum (NCBI Accession No. AAC49804), sweet potato (NCBI Accession Nos. AAC19119 and AAD38494), wheat (NCBI Accession Nos. BAB71785 and BAA77351), sugar beet (NCBI Accession No. AF173652), and rice (NCBI Accession Nos. AAD41242, AAD41241, and A1736032). Examples of soluble starch synthases include, but are not limited to, rice (NCBI Accession Nos. CAC59826, AAK64284, and AAK81729), *Arabidopsis thaliana* (NCBI Accession No. AAF24126), potato (NCBI Accession No. P93568), wheat (NCBI Accession No. Q43654), and sorghum (NCBI Accession No. AAD45815). Each of these Accession Nos. is herein incorporated by reference. Starch synthases are also disclosed in U.S. Pat. No. 6,423,886. An alignment of starch synthase from cassava (SEQ ID NO:27), pea (SEQ ID NO:28), rice (SEQ ID NOS:29, 30, and 31), and *Curcuma* (SEQ ID NO:2) is provided in FIG. 2. Plant starch synthase consensus regions can be found in Cao et al. (1999) Plant Physiol. 120:205-215.

Variants of plant starch synthases include both loss of function, recessive, and gain of function, dominant, mutant alleles. For example, the major granule-bound starch synthase in maize is encoded by the Wx gene. Recessive mutations in Wx resulting in either the absence or a decrease in the granule-bound starch synthase activity have been identified (Nelson et al. (1968) Genetics 60:507-524, Shure et al. (1983) *Cell* 35:225-233, Wessler et al. (1985) *PNAS* 82:4177-4181, and Klosgen et al. (1986) *Mol. Gen. Genet.* 203:237-244). Other variants of plant granule bound starch synthases include: the amf-1 from potato (Visser et al. (1989) *Plant Science* 64:185-192), the Wx-D1b null allele from wheat (NCBI Accession No. AF113844), and the Wx-A1 allele from wheat (NCBI Accession No. AF113843). Each of these Accession Nos. is herein incorporated by reference. Variants of soluble starch synthases include mutants of dull1 (Gao et al. (1998) *The Plant Cell* 10:399-412).

Assays for soluble or granule-bound starch synthases are also known in the art. Such assays include measuring the affinity for ADP glucose and glucan substrates, glucan synthase assays, activation by amylopectin, and the processivity of glucan chain extension. Such assays can be found in, for example, Edwards et al. (1999) *European J. Biochem.* 266:724-736, Cao et al. (1999) *Plant Physiol.* 120:205-215, and Cao et al. (2000) *Arch. Biochem. Biophys.* 373:135-146, herein incorporated by reference.

FtsZ proteins are involved in plastid division and are divided into two families, FtsZ1 and FtsZ2 (Osteryoung and Pyke (1998) *Curr. Opin. Plant Biol.* 1:475-479; Osteryoung et al. (1998) *Plant Cell* 10:1991-2004). FtsZ has also been identified in prokaryotes, where it is involved in cell division, and forms a ring at the leading edge of the cell division site. Bacterial and eukaryotic FtsZ proteins are highly conserved in the $NH_2$-terminal region, but more variable in the COOH terminus (Kiessling et al. (2000) *J. Cell Biol.* 151: 945-950). Three FtsZ genes (FtsZ1-1, FtsZ2-1 and FtsZ2-2) have been identified in *Arabidopsis*. They all contain cleavable chloroplast targeting transit peptide sequences (McAndrew et al. (2001) *Plant Physiol.* 127:1656-1666). Antisense down-regulation or overexpression of either FtsZ1 or FtsZ2 in transgenic *Arabidopsis* inhibits chloroplast division (Osteryoung et al. (1998) *Plant Cell* 10:1991-2004; Stokes et al. (2000) *Plant Physiol.* 124:1668-1677; McAndrew et al. (2001) Plant Physiol. 127:1656-1666)

Numerous FtsZ2 proteins have been isolated, including liverwort (NCBI Accession No. BAC57988) (SEQ ID NO:32), moss (NCBI Accession No. T51090) (SEQ ID NO:33), bread wheat (NCBI Accession No. CAD99148) (SEQ ID NO:34), potato (NCBI Accession No. CAD99146) (SEQ ID NO:35), tobacco (NCBI Accession No. CAB89288) (SEQ ID NO:36), *Arabidopsis thaliana* (NCBI Accession No. JC7770 (SEQ ID NO:37) and NCBI Accession No. AAK63846 (SEQ ID NO:38)). The amino acid sequences for these FtsZ2 proteins are aligned in FIG. 3.

The first plant FtsZ cDNA was isolated from a terrestrial seedless plant *Physcomitrella patens* (Strepp et al. (1998) *Proc. Natl. Acad. Sce. U.S.A.* 95:4368-4373). Its function was established by knockout plants generated by homologous recombination. Seven out of 51 transgenics contain one huge chloroplast per cell with no effect on mitochondrial division, indicating the chloroplast division in those plants was inhibited. Assays for measuring FtsZ protein activity are known in the art (see, for example, Stokes et al. (2000) *Plant Physiol.* 124:1668-1677; Vitha et al. (2001) *J Cell Biol* 153:111-119). Methods to assay for expression, including tissue-preferred expression, of the various polypeptides are known in the art. For example, transcript or protein levels can be assayed using standard molecular biology techniques.

The method of the invention increases the level of a polypeptide in a plastid. In general, the polypeptide level is increased by at least 1%, 5%, 10%, 20%, 30%, 40%, 50%, 60%, 70%, 80%, or 90% relative to a native control plant, plant part, or cell which did not have the sequence of interest introduced. The increase in the level of the polypeptide in the plastid may occur during and/or subsequent to growth of the plant to the desired stage of development. In specific embodiments, the polypeptides of the present invention are modulated in monocots, particularly maize.

An increase in the level of the heterologous polypeptide of the invention can be achieved by providing to the plant a heterologous polypeptide. As discussed elsewhere herein, many methods are known the art for providing a polypeptide to a plant including, but not limited to, direct introduction of the polypeptide into the plant, introducing into the plant (transiently or stably) a polynucleotide construct encoding a polypeptide.

The expression level of the heterologous polypeptide may be measured directly, for example, by assaying for the level of the heterologous polypeptide in the plant, or indirectly, for example, by measuring the activity of the heterologous polypeptide in the plant or by assaying for reduced starch granule size. Methods for determining the activity of representative polypeptides of interest are disclosed elsewhere herein.

In specific embodiments, the polypeptide or the polynucleotide of the invention is introduced into the plant cell. Subsequently, a plant cell having the introduced sequence of the invention is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity of polypeptides of the present invention in the plant. Plant forming conditions are well known in the art and discussed briefly elsewhere herein.

Physical Characteristics of Starch

Embodiments of the present invention produce transgenic plants that have reduced starch granule size. This reduced starch granule size increases the effective surface area and further enhances the rate of enzymatic digestion.

Furthermore, it is believed that expression of proteins in plastids such as amyloplasts and chloroplasts may produce starch granules that display a reduced temperature of gelatinization that would increase starch solubility during processing (grinding, pelleting, steam flaking) at temperatures below the gelatinization temperature of normal starch. The reduced gelatinization temperature may elevate the degree of starch gelatinization in processed feed and hence, starch digestibility, and reduce the energy required in feed processing (grinding, pelleting, steam-flanking).

The reduced starch granule size may lead to an increased digestibility of the starch. The modified starch granules with increased digestibility may be useful as silage or forage for feed animals. By "increased digestibility" is intended the rate of starch digestion is about 5% to about 10%, about 10% to about 15%, about 15% to about 25%, about 25% to about 50% or greater, or at least 5%, at least 10%, at least 15%, at least 20%, at least 25%, at least 30%, at least 35%, at least 40%, at least 45%, or at least 50% or greater than that of starch from an unmodified plant. By use of the PHI in vitro digestion test (4 hr. Enzyme Digestible Dry Matter (EDDM)), smaller granules produced by overexpression of Brittle-1 showed up to 13% greater EDDM that the control. Methods for measuring the rate of starch digestion include measuring α-amylase hydrolysis, and are well known in the art (see, for example Knutson et al. (1982) *Cereal Chem.* 59:512-515; Pell and Schofield (1993) J. Dairy Sci. 76:1063-1073; Schofield and Pell (1995) *J. Anim. Sci.* 73:3455-3463;

Franco et al. (1998) *Starch* 50:193-198; Kereliuk and Sosulski (1996) *Food Science and Technology* 29:349-356).

In one embodiment, starch from plants with reduced granule size may be chemically modified more effectively, for use in the production of food and industrial starches. In another embodiment, starch from plants with reduced granule size produces a different "mouth feel" when used as a food ingredient. This is useful in the manufacture of various processed food products, for example, starch-based fat mimetics. Sensory analysis of reduced-fat frozen desert mixes into which small starch granules from wheat and amaranth were incorporated indicated that up to 50% of the fat may be replaced by these starches at the 2% level (Malinski et al. (2003) *Cereal Chem.* 80:1-4). Methods for formulating deserts using modified starches and for performing sensory analysis of the products are well known in the art (see Malinski et al., supra).

In yet another embodiment, the grinding property of the grain is modified (i.e. the particle size distribution of ground grain), whereby less energy is needed to produce a ground product. This would benefit the feed and dry grind ethanol markets. In yet another embodiment, the grit yield of the grain is improved, leading to an advantage in the corn dry mill industry. Other physical properties of starch granules, such as thermal stabilization, retrogradation, water affinity, starch pasting, kernel texture, gel hardness, and viscosity might be altered as a result of the methods of the current invention. Assays to measure these physical characteristics are well known in the art (see, for example, Gaines et al, (2000) *Cereal Chem.* 77:163-168 and Chiotelli and Le Meste (2002) *Cereal Chem.* 79:286-293; Eliasson and Gudmundsson (1996) "Starch: Physicochemical and functional aspects." *Carbohydrates in Food*. A. C. Eliasson. 270 Madison Ave/New York/N.Y. 10016, Marcel Dekker: 431-503; Hizukuri (1996) "Starch: Analytical aspects." *Carbohydrates in Food* A. C. Eliasson. 270 Madison Ave/New York/N.Y. 10016, Marcel Dekker: 347-429; Morrison and Karkalas (1990) "Starch". *Methods In Plant Biochemistry*. P. M. Dey and J. B. Harborne, Academic Press Limited. 2:323-352.)

Variants and Fragments

Fragments and variants of the polynucleotide of interest and proteins encoded thereby can be used in the present invention. By "fragment" is intended a portion of the polynucleotide of interest or a portion of the amino acid sequence and hence protein encoded thereby. Fragments of a polynucleotide may encode protein fragments that retain the biological activity of the native protein and, when expressed in a plant plastid, reduce starch granule size. Thus, fragments of a polynucleotide may range from at least about 20 nucleotides, about 50 nucleotides, about 100 nucleotides, and up to the full-length polynucleotide encoding the proteins used in the methods of the invention.

A fragment of a polynucleotide that encodes a biologically active portion or a non-biologically active portion of a polypeptide of the invention will encode at least 15, 25, 30, 50, 100, 150, 200, 250, 300, 350, 400, 450, 500, 550, 600 or 650 contiguous amino acids, or up to the total number of amino acids present in a full-length protein of the invention (for example, 690 amino acids for SEQ ID NO:2, 436 for SEQ ID NO:8, 467 for SEQ ID NO:14, and 156 for SEQ ID NO:16).

Thus, a fragment of a polynucleotide may encode a biologically active portion of a polypeptide. A biologically active portion of a polypeptide can be prepared by isolating a portion of one of the polynucleotides encoding a polypeptide, expressing the encoded portion of the protein (e.g., by recombinant expression in vitro), and assessing the activity of the encoded portion of the polypeptide. Nucleic acid molecules that are fragments of a polynucleotide that modulate the activity of a polypeptide comprise at least 16, 20, 50, 75, 100, 150, 200, 250, 300, 350, 400, 450, 500, 550, 600, 650, 700, 800, 900, 1000, 1100, 1200, 1300, 1400, 1500, 1600, 1700, 1800, 1900, 2000 contiguous nucleotides, or up to the number of nucleotides present in a full-length polynucleotide encoding the protein (for example, 2073 nucleotides for SEQ ID NO:1, 1311 for SEQ ID NO:7, 1404 for SEQ ID NO:13, and 471 for SEQ ID NO:15).

By "variants" is intended substantially similar sequences. As used herein, a "native" polynucleotide or polypeptide comprises a naturally occurring polynucleotide or amino acid sequence, respectively. For polynucleotides, conservative variants include those sequences that, because of the degeneracy of the genetic code, encode similar amino acid sequences. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a polypeptide. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular polynucleotide used in the methods of the invention (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotide that encode a polypeptide with a given percent sequence identity to the polypeptide of SEQ ID NOS:2, 6, 8, 12, 14, and 16 are disclosed. Percent sequence identity between any two polypeptides can be calculated using sequence alignment programs described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

By "variant" protein is intended a protein derived from the native protein by deletion (so-called truncation) or addition of one or more amino acids to the N-terminal and/or C-terminal end of the native protein; deletion and/or addition of one or more amino acids at one or more sites in the native protein; or substitution of one or more amino acids at one or more sites in the native protein. Variant proteins encompassed by the present invention are biologically active, that is they continue to possess the biological activity of the native protein and, when expressed in a plant plastid, such as an amyloplast or a chloroplast, reduce starch granule size. Such variants may result from, for example, genetic polymorphism or from human manipulation. Biologically active variants of a native polypeptide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue. Peptides that are "substantially similar" share sequences as noted above except that residue positions that are not identical may differ by conservative amino acid changes.

The proteins used in the methods of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides used in the present invention include both the naturally occurring sequences as well as mutant forms. Likewise, the proteins used in the present invention encompass naturally occurring proteins as well as variations and modified forms thereof. Such variants will continue to possess the desired ability to reduce starch granule size when expressed in a plant plastid such as an amyloplast or a chloroplast. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences used in the methods encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assaying the characteristics of the starch granule synthesized. See Experimental section for methods to analyze the physical properties of starch granules. Alternatively, the activity of the protein can be assayed using methods described herein and compared to that of the unmodified protein.

Variant polynucleotides and proteins also encompass sequences and proteins derived from a mutagenic and recombinogenic procedure such as DNA shuffling. With such a procedure, one or more different sequences can be manipulated to create a new sequence possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the starch synthase gene of SEQ ID NO:3 and other known starch synthase genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The following terms are used to describe the sequence relationships between two or more polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide, wherein the polynucleotide in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Polynucleotide Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain polynucleotides homologous to a polynucleotide encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Polynucleotide Res*. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for polynucleotides, BLASTX for proteins) can be used. See www.ncbi.hlm.nih.gov. Alignment may also be performed manually by inspection.

Unless otherwise stated, sequence identity/similarity values provided herein refer to the value obtained using GAP Version 10 using the following parameters: % identity and % similarity for a polynucleotide using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol*. 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For polynucleotides the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotide or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotides means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two polynucleotides by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that polynucleotides are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Polynucleotides that do not hybridize to each other under stringent conditions are still substantially identical if the polypeptides they encode are substantially identical. This may occur, e.g., when a copy of a polynucleotide is created using the maximum codon degeneracy permitted by the genetic code. One indication that two polynucleotides are substantially identical is when the polypeptide encoded by the first polynucleotide is immunologically cross reactive with the polypeptide encoded by the second polynucleotide.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the sequence encoding the protein involved in starch granule formation. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire Curcuma soluble starch synthase polynucleotide disclosed herein (SEQ ID NO:1), or one or more portions thereof, may be used as a probe capable of specifically hybridizing to corresponding starch synthase polynucleotide and messenger RNAs. To achieve specific hybridization under a variety of conditions, such probes include sequences that are unique among starch synthase polynucleotides and are optimally at least about 10 nucleotides in length, and most optimally at least about 20 nucleotides in length. Such probes may be used to amplify corresponding starch synthase polynucleotide from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 hours to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of polynucleotide is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for a protein of interest and which hybridize under stringent conditions to the polynucleotides encoding the protein of interest, or to fragments thereof, may be used in the methods of the present invention.

Vectors and Expression Cassettes

The use of the term "nucleic acid" or "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides for use in the methods of the invention also encompass all forms of sequences including, but not limited to, single-stranded forms, double-stranded forms, hairpins, stem-and-loop structures, and the like.

The polynucleotides used in the methods of the present invention can be provided in expression cassettes for expression in a plant of interest. The expression cassette will include 5' and 3' regulatory sequences operably linked to a polynucleotide encoding a polypeptide. The cassette may additionally contain at least one additional gene to be cotransformed into the organism. Alternatively, the additional gene(s) can be provided on another expression cassette. Such an expression cassette is provided with a plurality of restriction sites and/or recombination sites for insertion of the polynucleotide of interest to be under the transcriptional regulation of the regulatory regions. The expression cassette may additionally contain selectable marker genes.

"Operably linked" is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame.

The expression cassette will include in the 5'-3' direction of transcription, a transcriptional and translational initiation region (i.e., a promoter), a coding sequence of the protein of interest and a transcriptional and translational termination region (i.e., termination region) functional in plants.

The coding sequence of the protein of interest is operably linked to a transit peptide that is capable of directing the sequence to the plastid. The regulatory regions (i.e., promoters, transcriptional regulatory regions, and translational termination regions) and/or the polynucleotide of interest and/or the transit peptide may be native/analogous to the host cell or to each other. Alternatively, the regulatory regions and/or the polynucleotide of interest and/or the transit peptide may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous transit peptide or heterologous polynucleotide is from a species different from the species from which the transit peptide or polynucleotide was derived, or, if from the same/analogous species, one or both are substantially modified from their original form and/or genomic locus, or the promoter is not the native promoter for the operably linked transit peptide or polynucleotide. When the native promoter sequences are used, the expression levels of the proteins in the plant or plant cell will change. Thus, the phenotype of the plant or plant cell is altered.

In one embodiment, the polynucleotide of interest is targeted to the chloroplast for expression. In this manner, where the polynucleotide of interest is not directly introduced into the chloroplast, the expression cassette will additionally contain a nucleic acid encoding a transit peptide to direct the gene product of interest to the chloroplasts.

The termination region may be native with the transcriptional initiation region, may be native with the operably linked DNA sequence of interest, or may be derived from another source (i.e., foreign or heterologous) to the promoter, the sequence of interest, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Polynucleotide Res.* 17:7891-7903; and Joshi et al. (1987) *Nucleic Acid Res.* 15:9627-9639.

Where appropriate, the polynucleotide may be optimized for increased expression in the transformed plant. That is, the polynucleotide can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Polynucleotide Res.* 17:477-498, herein incorporated by reference. In one embodiment, the polynucleotide of interest to be targeted to the chloroplast and/or amyloplast may be optimized for expression in the plastid to account for differences in codon usage between the plant nucleus and this organelle. In this manner, the polynucleotide of interest may be synthesized using chloroplast-(or amyloplast)-preferred codons. See, for example, U.S. Pat. No. 5,380,831, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' non-translated leader sequences or 5' non-coding sequences. As used herein, "5' leader sequence," "translation leader sequence," or "5' non-coding sequence" refer to that DNA sequence portion of a gene between the promoter and coding sequence that is transcribed into RNA and is present in the fully processed mRNA upstream (5') of the translation start codon. A 5' non-translated leader sequence is usually characterized as that portion of the mRNA molecule that most typically extends from the 5' CAP site to the AUG protein translation initiation codon. The translation leader sequence may affect processing of the primary transcript to mRNA, mRNA stability or translation efficiency (Turner et al. (1995) *Molecular Biotechnology* 3:225). Thus, translation leader sequences play an important role in the regulation of gene expression. Translation leaders are known in the art and include: picornavirus leaders, for example, EMCV leader (Encephalomyocarditis 5' noncoding region) (Elroy-Stein et al. (1989) *PNAS USA* 86:6126-6130); potyvirus leaders, for example, TEV leader (Tobacco Etch Virus) (Allison et al. (1986); MDMV leader (Maize Dwarf Mosaic Virus); *Virology* 154:9-20), and human immunoglobulin heavy-chain binding protein (BiP), (Macejak et al. (1991) *Nature* 353: 90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, N.Y.), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

The expression cassette may additionally contain a 3' non-coding sequence. A "3' non-coding sequence" or "3' non-translated region" refer to a polynucleotide located 3' (downstream) of a coding sequence and include polyadenylation signal sequences and other sequences encoding regulatory signals capable of affecting the addition of polyadenylic acid tracts to the 3' end of the mRNA precursor. A 3' non-translated region comprises a region of the mRNA generally beginning with the translation termination codon and extending at least beyond the polyadenylation site. Non-translated sequences located in the 3' end of a gene have been found to influence gene expression levels. Ingelbrecht et al. (see, *Plant Cell*, 1:671-680, 1989) evaluated the importance of these elements and found large differences in expression in stable plants depending on the source of the 3' non-translated region. Using 3' non-translated regions associated with octopine synthase, 2S seed protein from *Arabidopsis*, small subunit of rbcS from *Arabidopsis*, extension from carrot, and chalcone synthase from *Antirrhinium*, a 60-fold difference was observed between the best-expressing construct (which contained the rbcS 3' non-translated region) and the lowest-expressing construct (which contained the chalcone synthase 3' region).

Transcription levels may also be increased by the utilization of enhancers in combination with the promoter regions of the invention. Enhancers are polynucleotides that act to increase the expression of a promoter region. Enhancers are known in the art and include the SV40 enhancer region, the 35S enhancer element, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Reporter genes or selectable marker genes may be included in the expression cassettes. Examples of suitable reporter genes known in the art can be found in, for example, Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *BioTechniques* 19:650-655; and Chiu et al. (1996) *Current Biology* 6:325-330.

Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). Other examples of suitable selectable marker genes include, but are not limited to, genes encoding resistance to chloramphenicol (Herrera Estrella et al. (1983) *EMBO J.* 2:987-992); methotrexate (Herrera Estrella et al. (1983) *Nature* 303:209-213 and Meijer et al. (1991) *Plant Mol. Biol.* 16:807-820); hygromycin (Waldron et al. (1985) *Plant Mol. Biol.* 5:103-108 and Zhijian et al. (1995) *Plant Science* 108:219-227); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al. (1990) *Plant Mol. Biol.* 15:127-136); bromoxynil (Stalker et al. (1988) *Science* 242:419-423); glyphosate (Shaw et al. (1986) *Science* 233:478-481 and U.S. patent application Ser. No. 10/004,357); phosphinothricin (DeBlock et al. (1987) *EMBO J.* 6:2513-2518). The above list of selectable marker genes is not meant to be limiting. Any selectable marker gene can be used in the present invention.

Other genes that could serve utility in the recovery of transgenic events but might not be required in the final product would include, but are not limited to, examples such as GUS (b-glucoronidase; Jefferson (1987) *Plant Mol. Biol. Rep.* 5:387), GFP (green florescence protein; Chalfie et al. (1994) *Science* 263:802), luciferase (Riggs et al. (1987) *Polynucleotide Res.* 15(19):8115 and Luehrsen et al. (1992) *Methods Enzymol.* 216:397-414), and the maize genes encoding for anthocyanin production (Ludwig et al. (1990) *Science* 247:449).

A number of promoters can be used in the practice of the invention. The promoters can be selected based on the desired outcome. The polynucleotide can be combined with constitutive, tissue-preferred, or other promoters for expression in plants. "Tissue-preferred promoters" express the genes under their control in only one or more cell types in specific organs, specific tissues, or specific cell types. Tissue-preferred promoters include promoters that are temporally regulated, such as in early or late embryogenesis, during fruit ripening in developing seeds or fruit, in fully differentiated leaf, or at the onset of senescence. In contrast, "constitutive promoters" refer to promoters that are able to express the genes under their control in all or nearly all of the plant tissues during all or nearly all developmental stages of the plant, thereby generating "constitutive expression" of the genes. Yet another type of promoter known as an "inducible promoter" is a type of regulated promoter that can be turned on in one or more cell types by an external stimulus, such as a chemical, light, hormone, stress, or a pathogen.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target the expression of the protein within a particular plant tissue. Such promoters include, but are not limited to, seed-preferred promoters. "Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); and celA (cellulose synthase) (see WO 00/11177 and U.S. Pat. No. 6,225,529; herein incorporated by reference). Gamma-zein is an endosperm-specific promoter, as are the promoters for the high molecular weight glutenin (HMWG) of wheat, prolamin, ITR1, gliadin, branching enzyme, ADPG pyrophosphorylase, starch synthase, granule-bound starch synthase, and Glob-1. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, γ-zein, waxy, shrunken 1, shrunken 2, globulin 1, etc. See also WO 00/12733, where seed-preferred promoters from end1 and end2 genes are disclosed; herein incorporated by reference.

As used herein, "vector" refers to a DNA molecule such as a plasmid, cosmid, or bacterial phage for introducing a nucleotide construct, for example, an expression cassette, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, conventional breeding methods, stable transformation methods, transient transformation methods, and virus-mediated methods. "Transient transformation" is intended to mean that a polynucleotide is introduced into the plant and does not integrate into the genome of the plant or a polypeptide is introduced into a plant. By "stable transformation" is intended that the nucleotide construct introduced into a plant integrates into the genome of the plant and is capable of being inherited by progeny thereof. By "primary transformant" and "T0 generation" is intended transgenic plants that are of the same genetic generation as the tissue that was initially transformed (i.e., not having gone through meiosis and fertilization since transformation). "Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

The nucleotide constructs of the invention may be introduced into plants by contacting plants with a virus or viral polynucleotide. Generally, such methods involve incorporating a nucleotide construct of the invention within a viral DNA or RNA molecule. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367, and 5,316,931; herein incorporated by reference.

Transformation protocols as well as protocols for introducing polynucleotides into plants may vary depending on the type of plant or plant cell, i.e., monocot or dicot, targeted for transformation. Suitable methods of introducing polynucleotides into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat.

Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved. Thus, as used herein, "transformed seed" or "transgenic seed" refers to seeds that contain the nucleotide construct stably incorporated into the plant genome.

The present invention may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca saliva*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrim*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

Other plants of interest include grain plants that provide seeds of interest, oil-seed plants, and leguminous plants. Seeds of interest include grain seeds, such as corn, wheat, barley, rice, sorghum, rye, etc. Oil seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Gene Stacking

In certain embodiments the polynucleotides used in the methods of the present invention can be stacked with any combination of polynucleotides of interest in order to create plants with a desired trait. A trait, as used herein, refers to the phenotype derived from a particular sequence or groups of sequences. A single expression cassette may contain both a polynucleotide encoding a polypeptide of interest to decrease starch granule size, and at least one additional gene, such as the gamma zein gene, UDP glucose dehydrogenase gene (U.S. Pat. No. 6,399,859), RGP genes (U.S. Pat. No. 6,194,638), or genes employed to increase the oil content and/or quality of the plant. Alternatively, the additional gene(s) can be provided on multiple expression cassettes. In specific embodiments, the additional genes co-transformed into the plant include polynucleotides that, upon expression, modify the cell wall properties and/or starch content and/or oil content and/or oil quality of the seed and further enhance the nutritive and digestive value of the plant material.

The approach could be entirely transgenic (expression of a first polynucleotide encoding a protein of interest to decrease starch granule size, and expression or suppression of a second polynucleotide that modulates expression of a protein affecting rate of feed digestibility) or by transferring the second polynucleotide into a newly obtained transgenic plant that expresses a protein in a plant plastid, such as an amyloplast or a chloroplast. In a specific embodiment, the second polynucleotide results in greatly reduced levels of the 27 kDa γ-zein protein in endosperm cells.

These stacked combinations can be created by any method including, but not limited to, cross-breeding plants by any conventional or TopCross methodology, or genetic transformation. If the sequences are stacked by genetically transforming the plants, the polynucleotides of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotides can be stacked at a desired genomic location using a site-specific recombination system. See, for example, WO99/25821, WO99/25854, WO99/25840, WO99/25855, and WO99/25853, all of which are herein incorporated by reference.

Additional polynucleotides that can be introduced in combination with a polypeptide that reduces granule size include, but are not limited to, insecticidal coding sequences, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981,722); nematicidal coding sequences; disease or herbicide resistance genes (e.g., fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); antimicrobial coding sequences, anti-fungal coding sequences, anti-viral coding sequences, abiotic stress tolerance coding sequences, nutritional quality coding sequences, visible marker coding sequences, selectable marker coding sequences, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

Additional traits of interest include those desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5.602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

In specific embodiments of the present invention, the polynucleotide of the additional gene of interest can be used to generate antisense constructions, which are complementary to at least a portion of the messenger RNA (mRNA) encoding these proteins. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, 85%, 90% or 95% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

The polynucleotides of the additional gene of interest may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a polynucleotide that corresponds to the transcript of the endogenous gene. Typically, such a polynucleotide has substantial sequence identity to the sequence of the transcript of the endogenous gene, preferably greater than about 65% sequence identity, more preferably greater than about 85% sequence identity, most preferably greater than about 95% sequence identity. See U.S. Pat. Nos. 5,283,184 and 5,034,323; herein incorporated by reference.

The following examples are offered by way of illustration and not by way of limitation.

Experimental

EXAMPLE 1

Overexpression of Brittle-1 in Homozygous T3 Seed Reduces Starch Granule Size

Transformation constructs were made with the Brittle-1 gene (SEQ ID NO:7) including its transit peptide. The construct was operably linked to either the γ-zein or 22-kD zein promoter and delivered into plants via particle bombardment. Regenerated plants were grown in a greenhouse and pollinated with a proprietary inbred (subsequently serving as a recurring backcross inbred) to produce T1 seed. T1 seed of multiple transgenic events was sown in the field and resulting T1 plants were self-pollinated to produce multiple ears of T2 seed for each transgenic event. Seed of these ears were planted in the field on an ear-to-row basis and resulting T2 plants were self-pollinated to produce ears containing T3 seed. Multiple ears of T3 seed, each with robust seed set, were harvested from each row of T2 plants for each event. Twenty kernels from each ear of T3 seed were sown in a flat and grown in the greenhouse. After 10 days of growth, resulting seedlings were sprayed with a solution (1% vol/vol) of glufosinate herbicide. Seedlings were scored seven days later for resistance to the herbicide. Ears of T3 seed were classified as wild-type if all 20 seedlings were killed, hemizygous if only a portion of the seedlings were killed, and homozygous for the transgene if none of the seedlings displayed leaf burn. In total, T3 seed of 1351 ears were evaluated. To confirm the results, another 20 kernels from ears believed to be homozygous were planted, grown to the seedling stage, sprayed with a 2% (vol/vol) solution of glufosinate herbicide, and scored for leaf burn as done previously. Subsequently, endosperm were isolated from multiple wild-type and homozygous ears of T3 seed and compared as within-row segregants. Total protein was extracted from the endosperm, separated on SDS-PAGE gels, and immunologically evaluated via Western blots for the level of Brittle-1 protein. Multiple events overexpressed the Brittle-1 protein (data not shown), in some cases by as much as 32-fold compared to within-row wild-type endosperm, as quantified by serial dilution of protein extracts measured by Western analysis and quantitated with a Bio-Rad GS7000 densitometer. Finally, starch granules were isolated according to White et al. (White et al. (1990) *Cereal Chem.* 67:70-73) from wild-type and homozygous endosperm of transgenic events overexpressing the Brittle-1 protein. Granule size was measured by digital image analysis using a Leica DMLB microscope with a Diagnostics Instruments, Inc. SPOT camera and employing Media Cybernetics Image-Pro Plus (Ver 4.0) software. Results with the same isolated starch were later confirmed using a Malvern Mastersizer 2000 Low Angle Laser Light Scattering particle size analyzer, using absorption and refractive indexes of 0.1 and 1.53, respectively. Both methods of particle size analysis gave very similar results. As shown in Table 1, transgenic events overexpressing the Brittle-1 protein (SEQ ID NO:8) produced smaller-than-normal starch granules in the endosperm when compared to starch granules isolated from wild-type plants.

TABLE 1

Low Angle Laser Light Scattering (LALLS) determination of the size of starch granules isolated from T3 wild-type and transgenic homozygous endosperm overexpressing the Brittle-1 protein.

| SAMPLE NAME | Starch Granule Modal Size (micron) |
| --- | --- |
| Bt1-T3 Starch - TC2853 - Homo | 13.9 |
| Bt1-T3 Starch - TC2853 - Wild-type | 14.5 |
| Bt1-T3 Starch - TC2862a - Homo | 10.4 |
| Bt1-T3 Starch - TC2862a - Wild-type | 14.7 |
| Bt1-T3 Starch - TC2862b - Homo | 9.8 |
| Bt1-T3 Starch - TC2862b - Homo | 9.6 |
| Bt1-T3 Starch - TC2862b - Wild-type | 14.5 |
| Bt1-T3 Starch - TC2862b - Wild-type | 14.0 |
| Bt1-T3 Starch - TC2862c - Homo | 10.4 |
| Bt1-T3 Starch - TC2862c - Wild-type | 14.4 |
| Bt1-T3 Starch - TC2862c - Homo | 10.4 |
| Bt1-T3 Starch - TC2863a - Homo | 11.7 |
| Bt1-T3 Starch - TC2863a - Wild-type | 14.1 |
| Bt1-T3 Starch - TC2863b - Homo | 10.4 |
| Bt1-T3 Starch - TC2863b - Wild-type | 15.6 |
| Bt1-T3 Starch - TC2863b - Homo | 10.6 |
| Bt1-T3 Starch - TC2863b - Wild-type | 14.4 |
| Bt1-T3 Starch - TC2864 - Homo | 13.7 |
| Bt1-T3 Starch - TC2864 - Wild-type | 14.1 |

EXAMPLE 2

Overexpression of Brittle-1 Improves In Vitro Digestibility of Grain

T3 maize seed judged to be homozygous for transgenic expression of the Brittle-1 protein (SEQ ID NO:8) and displaying concomitant reduction of starch granule size were propagated in field plots and backcrossed with a recurring elite inbred. The genetic materials were then grown for an additional two generations, with self-pollination occurring in each cycle. This produced BC3S2 seed on ears that segregated for wild-type and homozygous transgenic backgrounds. Homozygotes were identified by segregation analysis of seedling sensitivity to glufosinate herbicide, as already described. Whole grain of wild-type and transgenic homozygous plants was used in an in vitro digestion assay which determines the amount of enzyme digestible dry matter. Enzyme digestible dry matter percent (EDDM %) of the grain was measured using the method of Boisen and Fernandez (Boisen and Fernandez (1997) *Animal Feed Sci. Technol.* 68:277), with the exceptions that pepsin and cell wall degradative enzymes were not used, pancreatin concentration was 0.5% (wt/vol), and incubation occurred for four hours. In addition to controlling the experiment by utilizing backcrossed genetic materials, replicated comparisons were always made by contrasting wild-type and homozygous transgenic ears that segregated from a common genetic pedigree. A consistent pattern of significantly increased digestibility was observed after four hours of digestion, as shown in FIG. 5. The grain from the Brittle-1 transgenic seed responded positively to pretreatment with dithiothreietol (DTT), indicating that the effect on digestion occurs by a mechanism different than that seen with the γ-zein gene. Furthermore, SDS-PAGE analysis of transgenic seed indicated that normal levels of γ-zein protein were present in the grain.

EXAMPLE 3

Overexpression of Oleosin Produces Smaller Starch Granules

Ole16 (SEQ ID NO:15) was expressed in maize endosperm using the γ-zein promoter and targeted to the amyloplast by linking the coding region of oleosin to the Brittle-1 transit peptide (SEQ ID NO:9). Endosperm were dissected from mature T1 seed and tested by Western blot analysis for overexpression of oleosin protein. Nontransgenic endosperm of the same genotype used for transformation was used as a negative control to determine the native level of oleosin present in mature maize endosperm. A small amount of the protein can be detected in mature wild-type endosperm even after great care is taken to avoid contamination with non-endosperm tissues. Hence, overexpression of oleosin against a low background of native occurring protein was easy to distinguish in transgenic seed (data not shown). Following Western blot analysis of multiple individual endosperm from transgenic events, pools were formed of wild-type and "overexpression" endosperm within the ears of multiple events. Starch was isolated from the pools and granule size determined using low angle laser light scattering for particle size determination. A strong coincidence of significantly smaller-than-normal granules was found in seed that overexpresses 16 kDa oleosin, as shown in Table 2.

TABLE 2

Low Angle Laser Light Scattering (LALLS) determination of the size of starch granules isolated from T1 wild-type endosperm and T1 transgenic endosperm overexpressing the 16 kDa oleosin protein

| Events (EU IDs) | Wild-type Mean Starch Granule Size (micron) | Transgenic Mean Starch Granule Size (micron) |
| --- | --- | --- |
| 3247998, 3248002, 3248010 | 16.2 | 13.2 |
| 3248002, 3248003, 3248012, 3248400 | 14.3 | 12.2 |

EXAMPLE 4

Overexpression of Curcuma Starch Synthase Reduces Starch Granule Size

A Curcuma zedoria starch synthase gene (SEQ ID NO:1) including its transit peptide was expressed in maize endosperm using the y-zein promoter. Endosperm were dissected from mature T1 seed and tested by Western blot analysis to demonstrate overexpression of the starch synthase protein. Only weak cross-reaction occurred between the antibody and native maize starch synthase protein (data not shown). Following Western blot analysis of multiple individual endosperm from single transgenic events, pools were formed of wild-type-and overexpression-endosperm within the ears of multiple events. Starch was isolated from the pools and granule size determined using low angle laser light scattering for particle size determination. A strong coincidence of significantly smaller-than-normal granules was found in seed that overexpresses the starch synthase protein, as shown in Table 3.

TABLE 3

Low Angle Laser Light Scattering (LALLS) determination of the size of starch granules isolated from T1 wild-type endosperm and T1 transgenic endosperm overexpressing the Curcuma zedoria starch synthase protein

| Event | Wild-type Starch Granule Modal Size (micron) | Transgenic Starch granule Modal Size (micron) |
| --- | --- | --- |
| 1869174 | 13.7 | 12.2 |
| 1869168 | 12.0 | 11.2 |
| 1865454 | 13.2 | 12.3 |

EXAMPLE 5

Overexpression of Zea mays FtsZ2 Reduces Starch Granule Size

ZM-FtsZ2 (SEQ ID NO:13) was transformed into maize and expressed in the endosperm using the gamma-zein promoter. This gene should have a transit peptide as both Arabidopsis FtsZ2-1 and FtsZ2-2 are targeted to the chloroplast by cleavable transit peptides, imported and localized to the chloroplast stroma (McAndrew et. al. (2001) Plant Physiology 127:1656-1666). T-zero plants were self-pollinated in the greenhouse and for each event endosperm were dissected from two mature T1 seed and pooled into one sample. Starch was isolated according to White et al., 1990, supra, and granule size distribution measured by Low Angle Laser Light Scattering (Malvern Mastersizer 2000). Attention was focused upon an event that displayed unusually small starch granules in the smaller half of the population of granules obtained from the bulk of two endosperm. Additional mature seed were retrieved for that transgenic event and endosperm isolated. A part of each endosperm was used for determination of starch granule size distribution, Western analysis of ZM-FtsZ2 protein expression, and PCR detection of the integrated DNA construct containing ZM-FtsZ2. Upon examining these parameters for 37 individual seed, 28 indicated the presence of the transgene nucleic acid and overexpression of the protein. There was a perfect correspondence between detection of the transgene and overexpression. Nine seed were wild-type, based upon PCR and Western analyses. The modal starch granule size of wild-type seed ranged from 18.4-22.6 microns and averaged 20.2 microns among wild-type endosperm. The 28 transgenic endosperm segregated within the same ear containing the wild-type seed. For the transgenic seed, the modal starch granule size ranged from 11.8-19.2 microns and averaged 16.4 microns across this class of endosperm. Overexpression of the ZM-FtsZ2 protein was easy to distinguish in transgenic, compared to wild-type, seed and resulted in a reduction of average size of endosperm starch granules.

EXAMPLE 6

Overexpression of Lec1 in Endosperm Does Not Result in Reduced Starch Granule Size A construct was designed to express the Lec1 protein (non-plastid-associated) (SEQ ID NO:20) in the endosperm and embryo by utilizing the γ-zein and Ltp2 promoters, respectively. Endosperm were dissected from mature T1 seed and tested by Western blot analysis for overexpression of Lec1 protein. Nontransgenic endosperm of the same genotype used for plant transformation was used as a negative control to determine that Lec1 protein cannot be detected in mature endosperm of wild-type seed. Western blot analysis confirmed that Lec1 was overexpressed in the endosperm of transgenic plants, but not wild-type (data not shown). Pools were made of wild-type or transgenic endosperm, starch was isolated from the pools, and starch granule size was measured. There was no consistent effect on starch granule size (Table 4), and all of the measurements were in the range of natural variation. Therefore, expression of this non-plastid-associated protein in the endosperm of plants did not result in reduced starch granule size.

TABLE 4

Low Angle Laser Light Scattering (LALLS) determination of the size of starch granules isolated from T1 wild-type endosperm and T1 transgenic endosperm overexpressing the Zea mays Lec1 protein

| Event | Wild-type Starch Granule Modal Size (micron) | Transgenic Starch Granule Modal Size (micorn) |
| --- | --- | --- |
| 4571021 | 17.0 | 16.7 |
| 4571022 | 16.3 | 15.4 |
| 4571023 | 16.2 | 16.4 |

TABLE 4-continued

Low Angle Laser Light Scattering (LALLS) determination of the size of starch granules isolated from T1 wild-type endosperm and T1 transgenic endosperm overexpressing the Zea mays Lec1 protein

| Event | Wild-type Starch Granule Modal Size (micron) | Transgenic Starch Granule Modal Size (micorn) |
|---|---|---|
| 4571024 | 15.1 | 14.0 |
| 4571025 | 15.7 | 15.5 |

EXAMPLE 7

Overexpression of Maize Xylose Isomerase in Endosperm Does Not Result in Reduced Starch Granule Size A construct was designed to express the *Zea mays* xylose isomerase (XI) protein (non-plastid-associated) (SEQ ID NO:18) in the endosperm by utilizing the γ-zein promoter. Endosperm were dissected from mature seed across several generations and tested by Western blot analysis for overexpression of XI protein. Nontransgenic endosperm of the same genotype used for plant transformation, or segregating wild-type seed in later generations, were used as a negative control to determine the difference between native levels of XI protein expression in the endosperm and transgenic overexpression of the protein. Western blot analysis confirmed that XI was strongly overexpressed in the endosperm of transgenic plants and was easily distinguishable from wild-type plants (data not shown). Pools were made of T3 wild-type or transgenic endosperm, starch was isolated from the pools, and starch granule size was measured by low angle laser light scattering particle size determination. The XI protein was strongly overexpressed in transgenic endosperm, but starch granule size was nearly identical between wild-type and transgenic seed, as shown in Table 5.

Therefore, overexpression of this non-plastid-associated protein in the endosperm of plants did not result in reduced starch granule size.

TABLE 5

Low Angle Laser Light Scattering (LALLS) determination of the size of starch granules isolated from T3 wild-type endosperm and T3 transgenic endosperm overexpressing the Zea mays xylose isomerase protein

| Event | Wild-type Starch Granule Modal Size (micron) | Transgenic Starch granule Modal Size (micron) |
|---|---|---|
| 1000685596 | 15.9 | 16.0 |
| 1000685662 | 15.2 | 15.6 |

The articles "a" and "an" are used herein to refer to one or more than one (i.e., to at least one) of the grammatical object of the article. By way of example, "an element" means one or more element.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

That which is claimed:

1. A method for reducing starch granule size in a plant, comprising stably introducing into the genome of said plant a DNA construct comprising a polynucleotide operably linked to a promoter that drives expression in a plant and operably linked to a plastid transit peptide, wherein said polynucleotide comprises the nucleotide sequence set forth in SEQ ID NO:7 or a variant thereof, wherein said variant has at least 95% sequence identity to the nucleotide sequence of SEQ ID NO:7, and wherein expression of said DNA construct results in said starch granule having a reduced size.

2. The method of claim 1, wherein said DNA construct is introduced into the plant by transformation.

3. The method of claim 1, wherein said plant is a monocot.

4. The method of claim 3, wherein said monocot is maize.

5. The method of claim 1, wherein said plant is a dicot.

6. The method of claim 1, wherein said promoter is a tissue-preferred promoter.

7. The method of claim 6, wherein said promoter is an endosperm-specific promoter.

8. The method of claim 1, wherein said promoter is selected from the group consisting of γ-zein, 22-kD zein, opaque2, Brittle-1, waxy, and Legumin1A.

9. The method of claim 1, wherein said plant expresses at least one additional heterologous polypeptide.

10. The method of claim 9, wherein said additional heterologous polypeptide is selected from the group consisting of gamma zein and UDP glucose dehydrogenase.

11. The method of claim 1, wherein said transit peptide is an amyloplast transit peptide.

12. The method of claim 1, wherein said transit peptide is selected from the group consisting of Brittle-1, *Curcuma* soluble starch synthase, ribulose bisphosphate carboxylase (small subunit), 5-(enolpyruvyl) shikimate-3-phosphate synthase (EPSPS), tryptophan synthase, chorismate synthase, plastocyanin, the transit peptide for the plant plastid acyl carrier protein (ACP), the transit peptide for GBSSI (granule bound starch synthase I), and chlorophyll AB binding protein transit peptides.

13. A plant having a heterologous DNA construct stably introduced into its genome, said DNA construct comprising a polynucleotide operably linked to a promoter that drives expression in a plant and operably linked to a plastid transit peptide, wherein said polynucleotide wherein said polynucleotide comprises the nucleotide sequence set forth in SEQ ID NO:7 or a variant thereof, wherein said variant has at least 95% sequence identity to the nucleotide sequence of SEQ ID NO:7, and wherein expression of said DNA construct results in said starch granule having a reduced size.

14. The plant of claim 13, wherein said transit peptide is selected from the group consisting of Brittle-1, *Curcuma* soluble starch synthase, ribulose bisphosphate carboxylase (small subunit), 5-(enolpyruvyl) shikimate-3-phosphate synthase (EPSPS), tryptophan synthase, chorismate synthase, plastocyanin, the transit peptide for the plant plastid acyl carrier protein (ACP), the transit peptide for GBSSI (granule bound starch synthase I), and chlorophyll AB binding protein transit peptides.

15. The plant of claim 13, wherein said plant is a monocot.

16. The plant of claim 15, wherein said monocot is maize.

17. The plant of claim 13, wherein said plant is a dicot.

18. The plant of claim 13, wherein said plant is a plant cell.

19. A transformed seed of the plant of claim 13.

* * * * *

UNITED STATES PATENT AND TRADEMARK OFFICE
CERTIFICATE OF CORRECTION

PATENT NO. : 7,317,146 B2  Page 1 of 1
APPLICATION NO. : 11/021464
DATED : January 8, 2008
INVENTOR(S) : Singletary et al.

It is certified that error appears in the above-identified patent and that said Letters Patent is hereby corrected as shown below:

<u>Column 122,</u>

<u>Line 11</u>: "wherein said polynucleotide wherein said polynucleotide" should read --wherein said polynucleotide--

Signed and Sealed this

Third Day of June, 2008

JON W. DUDAS
*Director of the United States Patent and Trademark Office*

SEQUENCE LISTING

```
<160> NUMBER OF SEQ ID NOS: 38

<210> SEQ ID NO 1
<211> LENGTH: 2073
<212> TYPE: DNA
<213> ORGANISM: Curcuma zedoria
<220> FEATURE:
<221> NAME/KEY: CDS
<222> LOCATION: (1)...(2073)
<223> OTHER INFORMATION: Soluble Starch Synthase

<400> SEQUENCE: 1 atg ttc tcc cac ctc cta tcc tct cct cca gcg ccg ccg ccg ccc ggc      48
Met Phe Ser His Leu Leu Ser Ser Pro Pro Ala Pro Pro Pro Pro Gly
 1               5                  10                  15 gcg gcc agc tgc cgc ctc ctg cac ggc ggg gct cgc cct ctt ggc cac      96
Ala Ala Ser Cys Arg Leu Leu His Gly Gly Ala Arg Pro Leu Gly His
                20                  25                  30 tct ccg ctt tgc tgg gcg aat cct ctc tgt acg agc cga ttt atg gcg     144
Ser Pro Leu Cys Trp Ala Asn Pro Leu Cys Thr Ser Arg Phe Met Ala
            35                  40                  45
```

-continued

| | | |
|---|---|---|
| ggt ctt tca gaa gtc aag aaa ggg agc aaa atc aca ctc aaa cat atc<br>Gly Leu Ser Glu Val Lys Lys Gly Ser Lys Ile Thr Leu Lys His Ile<br>50                  55                  60 | 192 |
| gat cac act gga agt gct cgc aca atg agg ttt ctt aat gct tta tac<br>Asp His Thr Gly Ser Ala Arg Thr Met Arg Phe Leu Asn Ala Leu Tyr<br>65                  70                  75                  80 | 240 |
| cat gga caa tca gcg gat cta gtt cca atc aac cac agg gga aag tct<br>His Gly Gln Ser Ala Asp Leu Val Pro Ile Asn His Arg Gly Lys Ser<br>                 85                  90                  95 | 288 |
| tca ggc gca gtt ggg aga agc aat att aat gat ata caa gag gat agc<br>Ser Gly Ala Val Gly Arg Ser Asn Ile Asn Asp Ile Gln Glu Asp Ser<br>100                105               110 | 336 |
| aat caa gat gtt gac att gcc gat gat tct gtt gca caa aca atg gaa<br>Asn Gln Asp Val Asp Ile Ala Asp Asp Ser Val Ala Gln Thr Met Glu<br>115                120               125 | 384 |
| caa agc aag aag gtg ttg gaa atg cag agg aac ctg ctg caa cag att<br>Gln Ser Lys Lys Val Leu Glu Met Gln Arg Asn Leu Leu Gln Gln Ile<br>130                135               140 | 432 |
| att gaa aag aga aat ttc tct gaa gag aca gaa tct tat gtc aag aaa<br>Ile Glu Lys Arg Asn Phe Ser Glu Glu Thr Glu Ser Tyr Val Lys Lys<br>145                150               155                160 | 480 |
| gat gag aac ctt gga att tat gca gaa gca tat atg caa acc tca aac<br>Asp Glu Asn Leu Gly Ile Tyr Ala Glu Ala Tyr Met Gln Thr Ser Asn<br>                 165               170               175 | 528 |
| aat caa caa gaa gct cca cca gaa gaa gga aat ctg aac tct cct cct<br>Asn Gln Gln Glu Ala Pro Pro Glu Glu Gly Asn Leu Asn Ser Pro Pro<br>180                185               190 | 576 |
| ttg gct ggt cca aat gta atg aat atc ata ttg gta gct gca gaa tgt<br>Leu Ala Gly Pro Asn Val Met Asn Ile Ile Leu Val Ala Ala Glu Cys<br>195                200               205 | 624 |
| gca cca tgg tct aaa aca ggt ggg ctt gga gat gtt gtt gga gct tta<br>Ala Pro Trp Ser Lys Thr Gly Gly Leu Gly Asp Val Val Gly Ala Leu<br>210                215               220 | 672 |
| cct aaa gca ttg gcc aag aga gga cat cgt gtc atg gta gtg tct cca<br>Pro Lys Ala Leu Ala Lys Arg Gly His Arg Val Met Val Val Ser Pro<br>225                230               235                240 | 720 |
| aga tat gga aac tat cct gaa cct aag gaa ata ggg aat ctt aaa agg<br>Arg Tyr Gly Asn Tyr Pro Glu Pro Lys Glu Ile Gly Asn Leu Lys Arg<br>                 245               250               255 | 768 |
| tac aag gtt gat gga cag gac atg gag att aaa tac tat cat act tac<br>Tyr Lys Val Asp Gly Gln Asp Met Glu Ile Lys Tyr Tyr His Thr Tyr<br>260                265               270 | 816 |
| atc gat tct gtt gat ttt gtc ttc atc gat agt cct att ttc cgc cat<br>Ile Asp Ser Val Asp Phe Val Phe Ile Asp Ser Pro Ile Phe Arg His<br>275                280               285 | 864 |
| att gga aat gat ata tat ggt gga aac cga gtg gac att tgg aag aga<br>Ile Gly Asn Asp Ile Tyr Gly Gly Asn Arg Val Asp Ile Leu Lys Arg<br>290                295               300 | 912 |
| atg gta ttg ttc tgc aaa gca gca gtt gag gtt cct tgg cat gtc cca<br>Met Val Leu Phe Cys Lys Ala Ala Val Glu Val Pro Trp His Val Pro<br>305                310               315                320 | 960 |
| tgt ggt gga ttc tgt tat gga gat ggg aat ttg gtt ttc att gcc aac<br>Cys Gly Gly Phe Cys Tyr Gly Asp Gly Asn Leu Val Phe Ile Ala Asn<br>                 325               330               335 | 1008 |
| gat tgg cat acc tcc tta ctt cca gtt tat ttg aag gca tgt ttc cgt<br>Asp Trp His Thr Ser Leu Leu Pro Val Tyr Leu Lys Ala Cys Phe Arg<br>340                345               350 | 1056 |
| gat cgt gga tta atg aca tac gct cgc tgt ctc ttg gtt att cac aac<br>Asp Arg Gly Leu Met Thr Tyr Ala Arg Cys Leu Leu Val Ile His Asn<br>355                360               365 | 1104 |

```
att gca cat cag ggt cgt ggt ccg cta gat gac ttc tca tat gtg gat      1152
Ile Ala His Gln Gly Arg Gly Pro Leu Asp Asp Phe Ser Tyr Val Asp
    370                 375                 380 ttg cca cat gat cac att gac tcg ttt aga ctg gat gat cct gtt gga      1200
Leu Pro His Asp His Ile Asp Ser Phe Arg Leu Asp Asp Pro Val Gly
385                 390                 395                 400 ggt gag cat ttt aac att ttt gca gct ggt ata aga gct gct gac cgt      1248
Gly Glu His Phe Asn Ile Phe Ala Ala Gly Ile Arg Ala Ala Asp Arg
                405                 410                 415 gtg gtt aca gtt agc cat ggc tat gct tgg gag tta aaa aca tct gaa      1296
Val Val Thr Val Ser His Gly Tyr Ala Trp Glu Leu Lys Thr Ser Glu
            420                 425                 430 ggt ggt tgg gga ttg cat gag atc atc aac gag tgc cat tgg aaa ttc      1344
Gly Gly Trp Gly Leu His Glu Ile Ile Asn Glu Cys His Trp Lys Phe
        435                 440                 445 cat ggt att gta aat gga atc gat acc cat agt tgg aat cca aaa ttt      1392
His Gly Ile Val Asn Gly Ile Asp Thr His Ser Trp Asn Pro Lys Phe
    450                 455                 460 gac gct cac tta aat tct gat ggt tac acc aac ttc acc ctg gaa act      1440
Asp Ala His Leu Asn Ser Asp Gly Tyr Thr Asn Phe Thr Leu Glu Thr
465                 470                 475                 480 ctt gaa atg gga aag gcc cag tgc aag gct gct ttg caa cga gag ttt      1488
Leu Glu Met Gly Lys Ala Gln Cys Lys Ala Ala Leu Gln Arg Glu Phe
                485                 490                 495 ggt ctg cct gtt cgt gac gac gtt cct att ctt gcc ttc att ggg aga      1536
Gly Leu Pro Val Arg Asp Asp Val Pro Ile Leu Ala Phe Ile Gly Arg
            500                 505                 510 tta gac cat caa aaa ggt ata gat ctc ata gcg gag gcc atg cac tgg      1584
Leu Asp His Gln Lys Gly Ile Asp Leu Ile Ala Glu Ala Met His Trp
        515                 520                 525 ctc gtc ggt caa gat cta cag ata atc atg ctg ggc act ggg agg cca      1632
Leu Val Gly Gln Asp Leu Gln Ile Ile Met Leu Gly Thr Gly Arg Pro
    530                 535                 540 gac ctc gag gat atg ctt cga aga ttt gaa cgt gag cat cgc ggt aag      1680
Asp Leu Glu Asp Met Leu Arg Arg Phe Glu Arg Glu His Arg Gly Lys
545                 550                 555                 560 gtc agg gga tgg gtt ggg ttc tca gtg aaa atg gct cat cgg atc aca      1728
Val Arg Gly Trp Val Gly Phe Ser Val Lys Met Ala His Arg Ile Thr
                565                 570                 575 gca ggt gct gat gcc cta ctg atg ccc tcc agg ttc gaa cct tgt gga      1776
Ala Gly Ala Asp Ala Leu Leu Met Pro Ser Arg Phe Glu Pro Cys Gly
            580                 585                 590 ttg aac caa ctt cac gct atg atg tac gga aca att cct gtt gtg cat      1824
Leu Asn Gln Leu His Ala Met Met Tyr Gly Thr Ile Pro Val Val His
        595                 600                 605 gca gta ggt ggt ctt cga gat act gtg caa cag ttt gat ccg ttc aat      1872
Ala Val Gly Gly Leu Arg Asp Thr Val Gln Gln Phe Asp Pro Phe Asn
    610                 615                 620 gag aca ggt ttg gga tgg acc ttt gac agg gca gag gca cat agg atg      1920
Glu Thr Gly Leu Gly Trp Thr Phe Asp Arg Ala Glu Ala His Arg Met
625                 630                 635                 640 ata gtg gca ctc ggc cat tgt cta aac aca tat cgg aat tac aag gag      1968
Ile Val Ala Leu Gly His Cys Leu Asn Thr Tyr Arg Asn Tyr Lys Glu
                645                 650                 655 agc tgg gtg gga ttg cag aag cga ggg atg atg cag gac ctc agt tgg      2016
Ser Trp Val Gly Leu Gln Lys Arg Gly Met Met Gln Asp Leu Ser Trp
            660                 665                 670 gag agt gct gcc gag cac tat gaa aaa gtc ctt gtt gct gcc aag tac      2064
Glu Ser Ala Ala Glu His Tyr Glu Lys Val Leu Val Ala Ala Lys Tyr
```

```
            675                 680                 685
caa tgg tga                                                              2073
Gln Trp  *
    690

<210> SEQ ID NO 2
<211> LENGTH: 690
<212> TYPE: PRT
<213> ORGANISM: Curcuma zedoria

<400> SEQUENCE: 2

Met Phe Ser His Leu Leu Ser Ser Pro Ala Pro Pro Pro Gly
 1               5                  10                  15

Ala Ala Ser Cys Arg Leu Leu His Gly Gly Ala Arg Pro Leu Gly His
                20                  25                  30

Ser Pro Leu Cys Trp Ala Asn Pro Leu Cys Thr Ser Arg Phe Met Ala
            35                  40                  45

Gly Leu Ser Glu Val Lys Lys Gly Ser Lys Ile Thr Leu Lys His Ile
        50                  55                  60

Asp His Thr Gly Ser Ala Arg Thr Met Arg Phe Leu Asn Ala Leu Tyr
65                  70                  75                  80

His Gly Gln Ser Ala Asp Leu Val Pro Ile Asn His Arg Gly Lys Ser
                85                  90                  95

Ser Gly Ala Val Gly Arg Ser Asn Ile Asn Asp Ile Gln Glu Asp Ser
            100                 105                 110

Asn Gln Asp Val Asp Ile Ala Asp Asp Ser Val Ala Gln Thr Met Glu
        115                 120                 125

Gln Ser Lys Lys Val Leu Glu Met Gln Arg Asn Leu Leu Gln Gln Ile
    130                 135                 140

Ile Glu Lys Arg Asn Phe Ser Glu Glu Thr Glu Ser Tyr Val Lys Lys
145                 150                 155                 160

Asp Glu Asn Leu Gly Ile Tyr Ala Glu Ala Tyr Met Gln Thr Ser Asn
                165                 170                 175

Asn Gln Gln Glu Ala Pro Pro Glu Glu Gly Asn Leu Asn Ser Pro Pro
            180                 185                 190

Leu Ala Gly Pro Asn Val Met Asn Ile Ile Leu Val Ala Ala Glu Cys
        195                 200                 205

Ala Pro Trp Ser Lys Thr Gly Gly Leu Gly Asp Val Val Gly Ala Leu
    210                 215                 220

Pro Lys Ala Leu Ala Lys Arg Gly His Arg Val Met Val Val Ser Pro
225                 230                 235                 240

Arg Tyr Gly Asn Tyr Pro Glu Pro Lys Glu Ile Gly Asn Leu Lys Arg
                245                 250                 255

Tyr Lys Val Asp Gly Gln Asp Met Glu Ile Lys Tyr Tyr His Thr Tyr
            260                 265                 270

Ile Asp Ser Val Asp Phe Val Phe Ile Asp Ser Pro Ile Phe Arg His
        275                 280                 285

Ile Gly Asn Asp Ile Tyr Gly Gly Asn Arg Val Asp Ile Leu Lys Arg
    290                 295                 300

Met Val Leu Phe Cys Lys Ala Ala Val Glu Val Pro Trp His Val Pro
305                 310                 315                 320

Cys Gly Gly Phe Cys Tyr Gly Asp Gly Asn Leu Val Phe Ile Ala Asn
                325                 330                 335

Asp Trp His Thr Ser Leu Leu Pro Val Tyr Leu Lys Ala Cys Phe Arg
            340                 345                 350
```

```
Asp Arg Gly Leu Met Thr Tyr Ala Arg Cys Leu Leu Val Ile His Asn
        355                 360                 365
Ile Ala His Gln Gly Arg Gly Pro Leu Asp Asp Phe Ser Tyr Val Asp
370                 375                 380
Leu Pro His Asp His Ile Asp Ser Phe Arg Leu Asp Asp Pro Val Gly
385                 390                 395                 400
Gly Glu His Phe Asn Ile Phe Ala Ala Gly Ile Arg Ala Ala Asp Arg
                405                 410                 415
Val Val Thr Val Ser His Gly Tyr Ala Trp Glu Leu Lys Thr Ser Glu
        420                 425                 430
Gly Gly Trp Gly Leu His Glu Ile Asn Glu Cys His Trp Lys Phe
            435                 440                 445
His Gly Ile Val Asn Gly Ile Asp Thr His Ser Trp Asn Pro Lys Phe
450                 455                 460
Asp Ala His Leu Asn Ser Asp Gly Tyr Thr Asn Phe Thr Leu Glu Thr
465                 470                 475                 480
Leu Glu Met Gly Lys Ala Gln Cys Lys Ala Ala Leu Gln Arg Glu Phe
                485                 490                 495
Gly Leu Pro Val Arg Asp Asp Val Pro Ile Leu Ala Phe Ile Gly Arg
        500                 505                 510
Leu Asp His Gln Lys Gly Ile Asp Leu Ile Ala Glu Ala Met His Trp
            515                 520                 525
Leu Val Gly Gln Asp Leu Gln Ile Ile Met Leu Gly Thr Gly Arg Pro
530                 535                 540
Asp Leu Glu Asp Met Leu Arg Arg Phe Glu Arg Glu His Arg Gly Lys
545                 550                 555                 560
Val Arg Gly Trp Val Gly Phe Ser Val Lys Met Ala His Arg Ile Thr
                565                 570                 575
Ala Gly Ala Asp Ala Leu Leu Met Pro Ser Arg Phe Glu Pro Cys Gly
        580                 585                 590
Leu Asn Gln Leu His Ala Met Met Tyr Gly Thr Ile Pro Val Val His
            595                 600                 605
Ala Val Gly Gly Leu Arg Asp Thr Val Gln Gln Phe Asp Pro Phe Asn
610                 615                 620
Glu Thr Gly Leu Gly Trp Thr Phe Asp Arg Ala Glu Ala His Arg Met
625                 630                 635                 640
Ile Val Ala Leu Gly His Cys Leu Asn Thr Tyr Arg Asn Tyr Lys Glu
                645                 650                 655
Ser Trp Val Gly Leu Gln Lys Arg Gly Met Met Gln Asp Leu Ser Trp
        660                 665                 670
Glu Ser Ala Ala Glu His Tyr Glu Lys Val Leu Val Ala Lys Tyr
            675                 680                 685
Gln Trp
690

<210> SEQ ID NO 3
<211> LENGTH: 246
<212> TYPE: DNA
<213> ORGANISM: Curcuma zedoria
<220> FEATURE:
<221> NAME/KEY: CDS
<222> LOCATION: (1)...(246)
<223> OTHER INFORMATION: Transit peptide for soluble starch synthase

<400> SEQUENCE: 3
```

```
atg ttc tcc cac ctc cta tcc tct cct cca gcg ccg ccg ccg ccc ggc        48
Met Phe Ser His Leu Leu Ser Ser Pro Pro Ala Pro Pro Pro Pro Gly
 1               5                  10                  15 gcg gcc agc tgc cgc ctc ctg cac ggc ggg gct cgc cct ctt ggc cac        96
Ala Ala Ser Cys Arg Leu Leu His Gly Gly Ala Arg Pro Leu Gly His
                20                  25                  30 tct ccg ctt tgc tgg gcg aat cct ctc tgt acg agc cga ttt atg gcg      144
Ser Pro Leu Cys Trp Ala Asn Pro Leu Cys Thr Ser Arg Phe Met Ala
             35                  40                  45 ggt ctt tca gaa gtc aag aaa ggg agc aaa atc aca ctc aaa cat atc      192
Gly Leu Ser Glu Val Lys Lys Gly Ser Lys Ile Thr Leu Lys His Ile
 50                  55                  60 gat cac act gga agt gct cgc aca atg agg ttt ctt aat gct tta tac      240
Asp His Thr Gly Ser Ala Arg Thr Met Arg Phe Leu Asn Ala Leu Tyr
 65                  70                  75                  80 cat gga                                                               246
His Gly
```

<210> SEQ ID NO 4
<211> LENGTH: 82
<212> TYPE: PRT
<213> ORGANISM: Curcuma zedoria

<400> SEQUENCE: 4

```
Met Phe Ser His Leu Leu Ser Ser Pro Pro Ala Pro Pro Pro Pro Gly
 1               5                  10                  15

Ala Ala Ser Cys Arg Leu Leu His Gly Gly Ala Arg Pro Leu Gly His
                20                  25                  30

Ser Pro Leu Cys Trp Ala Asn Pro Leu Cys Thr Ser Arg Phe Met Ala
             35                  40                  45

Gly Leu Ser Glu Val Lys Lys Gly Ser Lys Ile Thr Leu Lys His Ile
 50                  55                  60

Asp His Thr Gly Ser Ala Arg Thr Met Arg Phe Leu Asn Ala Leu Tyr
 65                  70                  75                  80

His Gly
```

<210> SEQ ID NO 5
<211> LENGTH: 1824
<212> TYPE: DNA
<213> ORGANISM: Curcuma zedoria
<220> FEATURE:
<221> NAME/KEY: CDS
<222> LOCATION: (1)...(1824)
<223> OTHER INFORMATION: Soluble starch synthase without transit peptide

<400> SEQUENCE: 5

```
tca gcg gat cta gtt cca atc aac cac agg gga aag tct tca ggc gca        48
Ser Ala Asp Leu Val Pro Ile Asn His Arg Gly Lys Ser Ser Gly Ala
 1               5                  10                  15 gtt ggg aga agc aat att aat gat ata caa gag gat agc aat caa gat        96
Val Gly Arg Ser Asn Ile Asn Asp Ile Gln Glu Asp Ser Asn Gln Asp
                20                  25                  30 gtt gac att gcc gat gat tct gtt gca caa aca atg gaa caa agc aag      144
Val Asp Ile Ala Asp Asp Ser Val Ala Gln Thr Met Glu Gln Ser Lys
             35                  40                  45 aag gtg ttg gaa atg cag agg aac ctg ctg caa cag att att gaa aag      192
Lys Val Leu Glu Met Gln Arg Asn Leu Leu Gln Gln Ile Ile Glu Lys
 50                  55                  60 aga aat ttc tct gaa gag aca gaa tct tat gtc aag aaa gat gag aac      240
Arg Asn Phe Ser Glu Glu Thr Glu Ser Tyr Val Lys Lys Asp Glu Asn
 65                  70                  75                  80
```

-continued

```
ctt gga att tat gca gaa gca tat atg caa acc tca aac aat caa caa      288
Leu Gly Ile Tyr Ala Glu Ala Tyr Met Gln Thr Ser Asn Asn Gln Gln
                85                  90                  95 gaa gct cca cca gaa gaa gga aat ctg aac tct cct cct ttg gct ggt      336
Glu Ala Pro Pro Glu Glu Gly Asn Leu Asn Ser Pro Pro Leu Ala Gly
            100                 105                 110 cca aat gta atg aat atc ata ttg gta gct gca gaa tgt gca cca tgg      384
Pro Asn Val Met Asn Ile Ile Leu Val Ala Ala Glu Cys Ala Pro Trp
        115                 120                 125 tct aaa aca ggt ggg ctt gga gat gtt gtt gga gct tta cct aaa gca      432
Ser Lys Thr Gly Gly Leu Gly Asp Val Val Gly Ala Leu Pro Lys Ala
    130                 135                 140 ttg gcc aag aga gga cat cgt gtc atg gta gtg tct cca aga tat gga      480
Leu Ala Lys Arg Gly His Arg Val Met Val Val Ser Pro Arg Tyr Gly
145                 150                 155                 160 aac tat cct gaa cct aag gaa ata ggg aat ctt aaa agg tac aag gtt      528
Asn Tyr Pro Glu Pro Lys Glu Ile Gly Asn Leu Lys Arg Tyr Lys Val
                165                 170                 175 gat gga cag gac atg gag att aaa tac tat cat act tac atc gat tct      576
Asp Gly Gln Asp Met Glu Ile Lys Tyr Tyr His Thr Tyr Ile Asp Ser
            180                 185                 190 gtt gat ttt gtc ttc atc gat agt cct att ttc cgc cat att gga aat      624
Val Asp Phe Val Phe Ile Asp Ser Pro Ile Phe Arg His Ile Gly Asn
        195                 200                 205 gat ata tat ggt gga aac cga gtg gac att ttg aag aga atg gta ttg      672
Asp Ile Tyr Gly Gly Asn Arg Val Asp Ile Leu Lys Arg Met Val Leu
    210                 215                 220 ttc tgc aaa gca gca gtt gag gtt cct tgg cat gtc cca tgt ggt gga      720
Phe Cys Lys Ala Ala Val Glu Val Pro Trp His Val Pro Cys Gly Gly
225                 230                 235                 240 ttc tgt tat gga gat ggg aat ttg gtt ttc att gcc aac gat tgg cat      768
Phe Cys Tyr Gly Asp Gly Asn Leu Val Phe Ile Ala Asn Asp Trp His
                245                 250                 255 acc tcc tta ctt cca gtt tat ttg aag gca tgt ttc cgt gat cgt gga      816
Thr Ser Leu Leu Pro Val Tyr Leu Lys Ala Cys Phe Arg Asp Arg Gly
            260                 265                 270 tta atg aca tac gct cgc tgt ctc ttg gtt att cac aac att gca cat      864
Leu Met Thr Tyr Ala Arg Cys Leu Leu Val Ile His Asn Ile Ala His
        275                 280                 285 cag ggt cgt ggt ccg cta gat gac ttc tca tat gtg gat ttg cca cat      912
Gln Gly Arg Gly Pro Leu Asp Asp Phe Ser Tyr Val Asp Leu Pro His
    290                 295                 300 gat cac att gac tcg ttt aga ctg gat gat cct gtt gga ggt gag cat      960
Asp His Ile Asp Ser Phe Arg Leu Asp Asp Pro Val Gly Gly Glu His
305                 310                 315                 320 ttt aac att ttt gca gct ggt ata aga gct gct gac cgt gtg gtt aca     1008
Phe Asn Ile Phe Ala Ala Gly Ile Arg Ala Ala Asp Arg Val Val Thr
                325                 330                 335 gtt agc cat ggc tat gct tgg gag tta aaa aca tct gaa ggt ggt tgg     1056
Val Ser His Gly Tyr Ala Trp Glu Leu Lys Thr Ser Glu Gly Gly Trp
            340                 345                 350 gga ttg cat gag atc atc aac gag tgc cat tgg aaa ttc cat ggt att     1104
Gly Leu His Glu Ile Ile Asn Glu Cys His Trp Lys Phe His Gly Ile
        355                 360                 365 gta aat gga atc gat acc cat agt tgg aat cca aaa ttt gac gct cac     1152
Val Asn Gly Ile Asp Thr His Ser Trp Asn Pro Lys Phe Asp Ala His
    370                 375                 380 tta aat tct gat ggt tac acc aac ttc acc ctg gaa act ctt gaa atg     1200
Leu Asn Ser Asp Gly Tyr Thr Asn Phe Thr Leu Glu Thr Leu Glu Met
```

```
                385                 390                 395                 400
gga aag gcc cag tgc aag gct gct ttg caa cga gag ttt ggt ctg cct     1248
Gly Lys Ala Gln Cys Lys Ala Ala Leu Gln Arg Glu Phe Gly Leu Pro
                405                 410                 415 gtt cgt gac gac gtt cct att ctt gcc ttc att ggg aga tta gac cat     1296
Val Arg Asp Asp Val Pro Ile Leu Ala Phe Ile Gly Arg Leu Asp His
            420                 425                 430 caa aaa ggt ata gat ctc ata gcg gag gcc atg cac tgg ctc gtc ggt     1344
Gln Lys Gly Ile Asp Leu Ile Ala Glu Ala Met His Trp Leu Val Gly
        435                 440                 445 caa gat cta cag ata atc atg ctg ggc act ggg agg cca gac ctc gag     1392
Gln Asp Leu Gln Ile Ile Met Leu Gly Thr Gly Arg Pro Asp Leu Glu
    450                 455                 460 gat atg ctt cga aga ttt gaa cgt gag cat cgc ggt aag gtc agg gga     1440
Asp Met Leu Arg Arg Phe Glu Arg Glu His Arg Gly Lys Val Arg Gly
465                 470                 475                 480 tgg gtt ggg ttc tca gtg aaa atg gct cat cgg atc aca gca ggt gct     1488
Trp Val Gly Phe Ser Val Lys Met Ala His Arg Ile Thr Ala Gly Ala
                485                 490                 495 gat gcc cta ctg atg ccc tcc agg ttc gaa cct tgt gga ttg aac caa     1536
Asp Ala Leu Leu Met Pro Ser Arg Phe Glu Pro Cys Gly Leu Asn Gln
            500                 505                 510 ctt cac gct atg atg tac gga aca att cct gtt gtg cat gca gta ggt     1584
Leu His Ala Met Met Tyr Gly Thr Ile Pro Val Val His Ala Val Gly
        515                 520                 525 ggt ctt cga gat act gtg caa cag ttt gat ccg ttc aat gag aca ggt     1632
Gly Leu Arg Asp Thr Val Gln Gln Phe Asp Pro Phe Asn Glu Thr Gly
    530                 535                 540 ttg gga tgg acc ttt gac agg gca gag gca cat agg atg ata gtg gca     1680
Leu Gly Trp Thr Phe Asp Arg Ala Glu Ala His Arg Met Ile Val Ala
545                 550                 555                 560 ctc ggc cat tgt cta aac aca tat cgg aat tac aag gag agc tgg gtg     1728
Leu Gly His Cys Leu Asn Thr Tyr Arg Asn Tyr Lys Glu Ser Trp Val
                565                 570                 575 gga ttg cag aag cga ggg atg atg cag gac ctc agt tgg gag agt gct     1776
Gly Leu Gln Lys Arg Gly Met Met Gln Asp Leu Ser Trp Glu Ser Ala
            580                 585                 590 gcc gag cac tat gaa aaa gtc ctt gtt gct gcc aag tac caa tgg tga     1824
Ala Glu His Tyr Glu Lys Val Leu Val Ala Ala Lys Tyr Gln Trp  *
        595                 600                 605

<210> SEQ ID NO 6
<211> LENGTH: 607
<212> TYPE: PRT
<213> ORGANISM: Curcuma zedoria

<400> SEQUENCE: 6

Ser Ala Asp Leu Val Pro Ile Asn His Arg Gly Lys Ser Ser Gly Ala
 1               5                  10                  15

Val Gly Arg Ser Asn Ile Asn Asp Ile Gln Glu Asp Ser Asn Gln Asp
                20                  25                  30

Val Asp Ile Ala Asp Asp Ser Val Ala Gln Thr Met Glu Gln Ser Lys
            35                  40                  45

Lys Val Leu Glu Met Gln Arg Asn Leu Leu Gln Ile Ile Glu Lys
     50                  55                  60

Arg Asn Phe Ser Glu Glu Thr Glu Ser Tyr Val Lys Lys Asp Glu Asn
65                  70                  75                  80

Leu Gly Ile Tyr Ala Glu Ala Tyr Met Gln Thr Ser Asn Asn Gln Gln
                85                  90                  95
```

-continued

```
Glu Ala Pro Pro Glu Gly Asn Leu Asn Ser Pro Pro Leu Ala Gly
             100                 105                 110
Pro Asn Val Met Asn Ile Ile Leu Val Ala Ala Glu Cys Ala Pro Trp
         115                 120                 125
Ser Lys Thr Gly Gly Leu Gly Asp Val Val Gly Ala Leu Pro Lys Ala
130                 135                 140
Leu Ala Lys Arg Gly His Arg Val Met Val Val Ser Pro Arg Tyr Gly
145                 150                 155                 160
Asn Tyr Pro Glu Pro Lys Glu Ile Gly Asn Leu Lys Arg Tyr Lys Val
                 165                 170                 175
Asp Gly Gln Asp Met Glu Ile Lys Tyr Tyr His Thr Tyr Ile Asp Ser
             180                 185                 190
Val Asp Phe Val Phe Ile Asp Ser Pro Ile Phe Arg His Ile Gly Asn
         195                 200                 205
Asp Ile Tyr Gly Gly Asn Arg Val Asp Ile Leu Lys Arg Met Val Leu
    210                 215                 220
Phe Cys Lys Ala Ala Val Glu Val Pro Trp His Val Pro Cys Gly Gly
225                 230                 235                 240
Phe Cys Tyr Gly Asp Gly Asn Leu Val Phe Ile Ala Asn Asp Trp His
                 245                 250                 255
Thr Ser Leu Leu Pro Val Tyr Leu Lys Ala Cys Phe Arg Asp Arg Gly
             260                 265                 270
Leu Met Thr Tyr Ala Arg Cys Leu Leu Val Ile His Asn Ile Ala His
         275                 280                 285
Gln Gly Arg Gly Pro Leu Asp Asp Phe Ser Tyr Val Asp Leu Pro His
    290                 295                 300
Asp His Ile Asp Ser Phe Arg Leu Asp Asp Pro Val Gly Gly Glu His
305                 310                 315                 320
Phe Asn Ile Phe Ala Ala Gly Ile Arg Ala Ala Asp Arg Val Val Thr
                 325                 330                 335
Val Ser His Gly Tyr Ala Trp Glu Leu Lys Thr Ser Glu Gly Gly Trp
             340                 345                 350
Gly Leu His Glu Ile Ile Asn Glu Cys His Trp Lys Phe His Gly Ile
         355                 360                 365
Val Asn Gly Ile Asp Thr His Ser Trp Asn Pro Lys Phe Asp Ala His
    370                 375                 380
Leu Asn Ser Asp Gly Tyr Thr Asn Phe Thr Leu Glu Thr Leu Glu Met
385                 390                 395                 400
Gly Lys Ala Gln Cys Lys Ala Ala Leu Gln Arg Glu Phe Gly Leu Pro
                 405                 410                 415
Val Arg Asp Asp Val Pro Ile Leu Ala Phe Ile Gly Arg Leu Asp His
             420                 425                 430
Gln Lys Gly Ile Asp Leu Ile Ala Glu Ala Met His Trp Leu Val Gly
         435                 440                 445
Gln Asp Leu Gln Ile Ile Met Leu Gly Thr Gly Arg Pro Asp Leu Glu
    450                 455                 460
Asp Met Leu Arg Arg Phe Glu Arg Glu His Arg Gly Lys Val Arg Gly
465                 470                 475                 480
Trp Val Gly Phe Ser Val Lys Met Ala His Arg Ile Thr Ala Gly Ala
                 485                 490                 495
Asp Ala Leu Leu Met Pro Ser Arg Phe Glu Pro Cys Gly Leu Asn Gln
             500                 505                 510
```

```
Leu His Ala Met Met Tyr Gly Thr Ile Pro Val Val His Ala Val Gly
        515                 520                 525

Gly Leu Arg Asp Thr Val Gln Gln Phe Asp Pro Phe Asn Glu Thr Gly
        530                 535                 540

Leu Gly Trp Thr Phe Asp Arg Ala Glu Ala His Arg Met Ile Val Ala
545                 550                 555                 560

Leu Gly His Cys Leu Asn Thr Tyr Arg Asn Tyr Lys Glu Ser Trp Val
                565                 570                 575

Gly Leu Gln Lys Arg Gly Met Met Gln Asp Leu Ser Trp Glu Ser Ala
            580                 585                 590

Ala Glu His Tyr Glu Lys Val Leu Val Ala Ala Lys Tyr Gln Trp
        595                 600                 605

<210> SEQ ID NO 7
<211> LENGTH: 1311
<212> TYPE: DNA
<213> ORGANISM: Zea mays
<220> FEATURE:
<221> NAME/KEY: CDS
<222> LOCATION: (1)...(1311)
<223> OTHER INFORMATION: Brittle-1

<400> SEQUENCE: 7
```

| | | | | | | | | | | | | | | | | |
|---|---|---|---|---|---|---|---|---|---|---|---|---|---|---|---|---|
| atg | gcg | gcg | aca | atg | gca | gtg | acg | acg | atg | gtg | acg | agg | agc | aag | gag | 48 |
| Met | Ala | Ala | Thr | Met | Ala | Val | Thr | Thr | Met | Val | Thr | Arg | Ser | Lys | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| agc | tgg | tcg | tca | ttg | cag | gtc | ccg | gcg | gtg | gca | ttc | cct | tgg | aag | cca | 96 |
| Ser | Trp | Ser | Ser | Leu | Gln | Val | Pro | Ala | Val | Ala | Phe | Pro | Trp | Lys | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| cga | ggt | ggc | aag | acc | ggc | ggc | ctc | gag | ttc | cct | cgc | cgg | gcg | atg | ttc | 144 |
| Arg | Gly | Gly | Lys | Thr | Gly | Gly | Leu | Glu | Phe | Pro | Arg | Arg | Ala | Met | Phe | |
| | | 35 | | | | | 40 | | | | | 45 | | | | |

| | | | | | | | | | | | | | | | | |
|---|---|---|---|---|---|---|---|---|---|---|---|---|---|---|---|---|
| gcc | agc | gtc | ggc | ctc | aac | gtg | tgc | ccg | ggc | gtc | cca | gcg | ggg | cgc | gac | 192 |
| Ala | Ser | Val | Gly | Leu | Asn | Val | Cys | Pro | Gly | Val | Pro | Ala | Gly | Arg | Asp | |
| | 50 | | | | | 55 | | | | | 60 | | | | | |

| | | | | | | | | | | | | | | | | |
|---|---|---|---|---|---|---|---|---|---|---|---|---|---|---|---|---|
| ccg | cgg | gag | ccc | gat | ccc | aag | gtc | gtc | cgg | gcg | gcc | gac | aac | tgc | gac | 240 |
| Pro | Arg | Glu | Pro | Asp | Pro | Lys | Val | Val | Arg | Ala | Ala | Asp | Asn | Cys | Asp | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| atc | gcc | gcc | agc | ttg | gcg | ccg | ccg | ttc | ccg | ggc | agc | agg | ccg | cct | ggg | 288 |
| Ile | Ala | Ala | Ser | Leu | Ala | Pro | Pro | Phe | Pro | Gly | Ser | Arg | Pro | Pro | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| agg | cga | gga | aga | ggc | agc | gaa | gag | gag | gaa | gca | gaa | ggg | cgg | cgg | cac | 336 |
| Arg | Arg | Gly | Arg | Gly | Ser | Glu | Glu | Glu | Glu | Ala | Glu | Gly | Arg | Arg | His | |
| | | | | 100 | | | | | 105 | | | | | 110 | | |

| | | | | | | | | | | | | | | | | |
|---|---|---|---|---|---|---|---|---|---|---|---|---|---|---|---|---|
| gaa | gaa | gca | gca | gca | gct | ggg | cga | tct | gag | cct | gag | gaa | ggt | cag | ggt | 384 |
| Glu | Glu | Ala | Ala | Ala | Ala | Gly | Arg | Ser | Glu | Pro | Glu | Glu | Gly | Gln | Gly | |
| | | | 115 | | | | | 120 | | | | | 125 | | | |

| | | | | | | | | | | | | | | | | |
|---|---|---|---|---|---|---|---|---|---|---|---|---|---|---|---|---|
| caa | gat | cgc | caa | ccc | gca | cct | gcg | cgc | ctg | gtt | agc | ggc | gcc | atc | gcc | 432 |
| Gln | Asp | Arg | Gln | Pro | Ala | Pro | Ala | Arg | Leu | Val | Ser | Gly | Ala | Ile | Ala | |
| | 130 | | | | | 135 | | | | | 140 | | | | | |

| | | | | | | | | | | | | | | | | |
|---|---|---|---|---|---|---|---|---|---|---|---|---|---|---|---|---|
| ggc | gcc | gtg | tcc | agg | acg | ttt | gtg | gcg | ccg | ctg | gag | acg | atc | cgg | acg | 480 |
| Gly | Ala | Val | Ser | Arg | Thr | Phe | Val | Ala | Pro | Leu | Glu | Thr | Ile | Arg | Thr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cac | ttg | atg | gtc | ggc | agc | atc | ggc | gtc | gac | tca | atg | gcc | ggg | gtg | ttc | 528 |
| His | Leu | Met | Val | Gly | Ser | Ile | Gly | Val | Asp | Ser | Met | Ala | Gly | Val | Phe | |
| | | | | 165 | | | | | 170 | | | | | 175 | | |

| | | | | | | | | | | | | | | | | |
|---|---|---|---|---|---|---|---|---|---|---|---|---|---|---|---|---|
| cag | tgg | atc | atg | cag | aac | gaa | ggg | tgg | acc | ggc | ctg | ttc | cgc | ggc | aac | 576 |
| Gln | Trp | Ile | Met | Gln | Asn | Glu | Gly | Trp | Thr | Gly | Leu | Phe | Arg | Gly | Asn | |
| | | | | 180 | | | | | 185 | | | | | 190 | | |

| | | | | | | | | | | | | | | | | |
|---|---|---|---|---|---|---|---|---|---|---|---|---|---|---|---|---|
| gcc | gtc | aac | gtc | ctg | cgc | gtc | gct | ccg | agc | aag | gct | atc | gag | cat | ttc | 624 |

-continued

| | | | | | | | | | | | | | | | | |
|---|---|---|---|---|---|---|---|---|---|---|---|---|---|---|---|---|
| Ala | Val | Asn | Val | Leu | Arg | Val | Ala | Pro | Ser | Lys | Ala | Ile | Glu | His | Phe | |
| | | 195 | | | | 200 | | | | 205 | | | | | | |

| acc | tat | gac | acg | gcc | aag | aag | ttc | cta | acc | ccc | aag | ggc | gac | gag | ccg | 672 |
|---|---|---|---|---|---|---|---|---|---|---|---|---|---|---|---|---|
| Thr | Tyr | Asp | Thr | Ala | Lys | Lys | Phe | Leu | Thr | Pro | Lys | Gly | Asp | Glu | Pro | |
| 210 | | | | | 215 | | | | | 220 | | | | | | |

| ccc | aag | atc | ccg | atc | ccc | act | ccg | ctg | gtt | gcc | gga | gct | cta | gcc | gga | 720 |
|---|---|---|---|---|---|---|---|---|---|---|---|---|---|---|---|---|
| Pro | Lys | Ile | Pro | Ile | Pro | Thr | Pro | Leu | Val | Ala | Gly | Ala | Leu | Ala | Gly | |
| 225 | | | | 230 | | | | | 235 | | | | | 240 | | |

| ttc | gcc | tca | acc | ttg | tgc | acc | tac | cca | atg | gag | ctg | atc | aag | acc | agg | 768 |
|---|---|---|---|---|---|---|---|---|---|---|---|---|---|---|---|---|
| Phe | Ala | Ser | Thr | Leu | Cys | Thr | Tyr | Pro | Met | Glu | Leu | Ile | Lys | Thr | Arg | |
| | | | | 245 | | | | | 250 | | | | | 255 | | |

| gtc | acc | atc | gag | aag | gac | gta | tac | gac | aac | gtc | gcg | cac | gcg | ttc | gtg | 816 |
|---|---|---|---|---|---|---|---|---|---|---|---|---|---|---|---|---|
| Val | Thr | Ile | Glu | Lys | Asp | Val | Tyr | Asp | Asn | Val | Ala | His | Ala | Phe | Val | |
| | | | 260 | | | | | 265 | | | | | 270 | | | |

| aag | atc | cta | cgc | gac | gag | ggc | ccg | tcg | gag | ctg | tac | cgt | ggg | ctg | aca | 864 |
|---|---|---|---|---|---|---|---|---|---|---|---|---|---|---|---|---|
| Lys | Ile | Leu | Arg | Asp | Glu | Gly | Pro | Ser | Glu | Leu | Tyr | Arg | Gly | Leu | Thr | |
| | | 275 | | | | | 280 | | | | | 285 | | | | |

| ccc | agc | ctg | atc | ggc | gtg | gtg | ccg | tac | gcg | gcc | tgt | aac | ttc | tac | gcc | 912 |
|---|---|---|---|---|---|---|---|---|---|---|---|---|---|---|---|---|
| Pro | Ser | Leu | Ile | Gly | Val | Val | Pro | Tyr | Ala | Ala | Cys | Asn | Phe | Tyr | Ala | |
| | 290 | | | | | 295 | | | | | 300 | | | | | |

| tac | gag | acg | ctg | aag | cgg | ctc | tac | cgt | cgc | gcg | acc | ggg | cgg | cgt | ccc | 960 |
|---|---|---|---|---|---|---|---|---|---|---|---|---|---|---|---|---|
| Tyr | Glu | Thr | Leu | Lys | Arg | Leu | Tyr | Arg | Arg | Ala | Thr | Gly | Arg | Arg | Pro | |
| 305 | | | | 310 | | | | | 315 | | | | | 320 | | |

| ggc | gcg | gac | gtg | ggc | ccc | gtg | gcg | acg | ctg | ctc | atc | ggg | tcc | gcg | gcg | 1008 |
|---|---|---|---|---|---|---|---|---|---|---|---|---|---|---|---|---|
| Gly | Ala | Asp | Val | Gly | Pro | Val | Ala | Thr | Leu | Leu | Ile | Gly | Ser | Ala | Ala | |
| | | | | 325 | | | | | 330 | | | | | 335 | | |

| ggc | gcc | atc | gcc | agc | tcg | gcc | acg | ttc | ccg | cta | gag | gtg | gcc | cgc | aag | 1056 |
|---|---|---|---|---|---|---|---|---|---|---|---|---|---|---|---|---|
| Gly | Ala | Ile | Ala | Ser | Ser | Ala | Thr | Phe | Pro | Leu | Glu | Val | Ala | Arg | Lys | |
| | | | 340 | | | | | 345 | | | | | 350 | | | |

| cag | atg | cag | gtg | ggc | gct | gtg | ggc | ggg | agg | cag | gtg | tac | cag | aac | gtc | 1104 |
|---|---|---|---|---|---|---|---|---|---|---|---|---|---|---|---|---|
| Gln | Met | Gln | Val | Gly | Ala | Val | Gly | Gly | Arg | Gln | Val | Tyr | Gln | Asn | Val | |
| | | 355 | | | | | 360 | | | | | 365 | | | | |

| ctc | cac | gct | atc | tac | tgc | atc | ctc | aag | aag | gag | ggc | gcc | ggc | ggc | ctg | 1152 |
|---|---|---|---|---|---|---|---|---|---|---|---|---|---|---|---|---|
| Leu | His | Ala | Ile | Tyr | Cys | Ile | Leu | Lys | Lys | Glu | Gly | Ala | Gly | Gly | Leu | |
| | 370 | | | | | 375 | | | | | 380 | | | | | |

| tac | cga | ggt | ctc | ggc | cct | agc | tgc | atc | aag | ctc | atg | ccc | gcc | gcc | ggc | 1200 |
|---|---|---|---|---|---|---|---|---|---|---|---|---|---|---|---|---|
| Tyr | Arg | Gly | Leu | Gly | Pro | Ser | Cys | Ile | Lys | Leu | Met | Pro | Ala | Ala | Gly | |
| 385 | | | | | 390 | | | | | 395 | | | | | 400 | |

| atc | gcc | ttc | atg | tgc | tac | gag | gcg | tgc | aag | aag | atc | ctc | gtc | gac | aag | 1248 |
|---|---|---|---|---|---|---|---|---|---|---|---|---|---|---|---|---|
| Ile | Ala | Phe | Met | Cys | Tyr | Glu | Ala | Cys | Lys | Lys | Ile | Leu | Val | Asp | Lys | |
| | | | | 405 | | | | | 410 | | | | | 415 | | |

| gag | gat | gag | gag | gag | gag | gac | gaa | gcc | ggc | ggc | gga | gag | gat | gac | aag | 1296 |
|---|---|---|---|---|---|---|---|---|---|---|---|---|---|---|---|---|
| Glu | Asp | Glu | Glu | Glu | Glu | Asp | Glu | Ala | Gly | Gly | Gly | Glu | Asp | Asp | Lys | |
| | | | | 420 | | | | | 425 | | | | | 430 | | |

| aaa | aag | gtt | gaa | tga | | | | | | | | | | | | 1311 |
|---|---|---|---|---|---|---|---|---|---|---|---|---|---|---|---|---|
| Lys | Lys | Val | Glu | * | | | | | | | | | | | | |
| | | 435 | | | | | | | | | | | | | | |

<210> SEQ ID NO 8
<211> LENGTH: 436
<212> TYPE: PRT
<213> ORGANISM: Zea mays

<400> SEQUENCE: 8

| Met | Ala | Ala | Thr | Met | Ala | Val | Thr | Thr | Met | Val | Thr | Arg | Ser | Lys | Glu |
|---|---|---|---|---|---|---|---|---|---|---|---|---|---|---|---|
| 1 | | | | 5 | | | | | 10 | | | | | 15 | |

| Ser | Trp | Ser | Ser | Leu | Gln | Val | Pro | Ala | Val | Ala | Phe | Pro | Trp | Lys | Pro |
|---|---|---|---|---|---|---|---|---|---|---|---|---|---|---|---|
| | | | 20 | | | | | 25 | | | | | 30 | | |

| Arg | Gly | Gly | Lys | Thr | Gly | Gly | Leu | Glu | Phe | Pro | Arg | Arg | Ala | Met | Phe |
|---|---|---|---|---|---|---|---|---|---|---|---|---|---|---|---|
| | | 35 | | | | | 40 | | | | | 45 | | | |

```
Ala Ser Val Gly Leu Asn Val Cys Pro Gly Val Pro Ala Gly Arg Asp
 50                  55                  60
Pro Arg Glu Pro Asp Pro Lys Val Val Arg Ala Ala Asp Asn Cys Asp
 65                  70                  75                  80
Ile Ala Ala Ser Leu Ala Pro Pro Phe Pro Gly Ser Arg Pro Pro Gly
                 85                  90                  95
Arg Arg Gly Arg Gly Ser Glu Glu Glu Ala Glu Gly Arg Arg His
            100                 105                 110
Glu Glu Ala Ala Ala Gly Arg Ser Glu Pro Glu Glu Gly Gln Gly
        115                 120                 125
Gln Asp Arg Gln Pro Ala Pro Ala Arg Leu Val Ser Gly Ala Ile Ala
    130                 135                 140
Gly Ala Val Ser Arg Thr Phe Val Ala Pro Leu Glu Thr Ile Arg Thr
145                 150                 155                 160
His Leu Met Val Gly Ser Ile Gly Val Asp Ser Met Ala Gly Val Phe
                165                 170                 175
Gln Trp Ile Met Gln Asn Glu Gly Trp Thr Gly Leu Phe Arg Gly Asn
            180                 185                 190
Ala Val Asn Val Leu Arg Val Ala Pro Ser Lys Ala Ile Glu His Phe
        195                 200                 205
Thr Tyr Asp Thr Ala Lys Lys Phe Leu Thr Pro Lys Gly Asp Glu Pro
    210                 215                 220
Pro Lys Ile Pro Ile Pro Thr Pro Leu Val Ala Gly Ala Leu Ala Gly
225                 230                 235                 240
Phe Ala Ser Thr Leu Cys Thr Tyr Pro Met Glu Leu Ile Lys Thr Arg
                245                 250                 255
Val Thr Ile Glu Lys Asp Val Tyr Asp Asn Val Ala His Ala Phe Val
            260                 265                 270
Lys Ile Leu Arg Asp Glu Gly Pro Ser Glu Leu Tyr Arg Gly Leu Thr
        275                 280                 285
Pro Ser Leu Ile Gly Val Val Pro Tyr Ala Ala Cys Asn Phe Tyr Ala
    290                 295                 300
Tyr Glu Thr Leu Lys Arg Leu Tyr Arg Arg Ala Thr Gly Arg Arg Pro
305                 310                 315                 320
Gly Ala Asp Val Gly Pro Val Ala Thr Leu Leu Ile Gly Ser Ala Ala
                325                 330                 335
Gly Ala Ile Ala Ser Ser Ala Thr Phe Pro Leu Glu Val Ala Arg Lys
            340                 345                 350
Gln Met Gln Val Gly Ala Val Gly Gly Arg Gln Val Tyr Gln Asn Val
        355                 360                 365
Leu His Ala Ile Tyr Cys Ile Leu Lys Lys Glu Gly Ala Gly Gly Leu
    370                 375                 380
Tyr Arg Gly Leu Gly Pro Ser Cys Ile Lys Leu Met Pro Ala Ala Gly
385                 390                 395                 400
Ile Ala Phe Met Cys Tyr Glu Ala Cys Lys Lys Ile Leu Val Asp Lys
                405                 410                 415
Glu Asp Glu Glu Glu Glu Asp Glu Ala Gly Gly Gly Glu Asp Asp Lys
            420                 425                 430
Lys Lys Val Glu
        435

<210> SEQ ID NO 9
<211> LENGTH: 225
```

-continued

```
<212> TYPE: DNA
<213> ORGANISM: Zea mays
<220> FEATURE:
<221> NAME/KEY: CDS
<222> LOCATION: (1)...(225)
<223> OTHER INFORMATION: Transit peptide of Brittle-1

<400> SEQUENCE: 9 atg gcg gcg aca atg gca gtg acg acg atg gtg acg agg agc aag gag        48
Met Ala Ala Thr Met Ala Val Thr Thr Met Val Thr Arg Ser Lys Glu
 1               5                  10                  15 agc tgg tcg tca ttg cag gtc ccg gcg gtg gca ttc cct tgg aag cca        96
Ser Trp Ser Ser Leu Gln Val Pro Ala Val Ala Phe Pro Trp Lys Pro
             20                  25                  30 cga ggt ggc aag acc ggc ggc ctc gag ttc cct cgc ggg gcg atg ttc       144
Arg Gly Gly Lys Thr Gly Gly Leu Glu Phe Pro Arg Arg Ala Met Phe
         35                  40                  45 gcc agc gtc ggc ctc aac gtg tgc ccg ggc gtc cca gcg ggg cgc gac       192
Ala Ser Val Gly Leu Asn Val Cys Pro Gly Val Pro Ala Gly Arg Asp
     50                  55                  60 ccg cgg gag ccc gat ccc aag gtc gtc cgg gcg                           225
Pro Arg Glu Pro Asp Pro Lys Val Val Arg Ala
 65                  70                  75

<210> SEQ ID NO 10
<211> LENGTH: 75
<212> TYPE: PRT
<213> ORGANISM: Zea mays

<400> SEQUENCE: 10

Met Ala Ala Thr Met Ala Val Thr Thr Met Val Thr Arg Ser Lys Glu
 1               5                  10                  15

Ser Trp Ser Ser Leu Gln Val Pro Ala Val Ala Phe Pro Trp Lys Pro
             20                  25                  30

Arg Gly Gly Lys Thr Gly Gly Leu Glu Phe Pro Arg Arg Ala Met Phe
         35                  40                  45

Ala Ser Val Gly Leu Asn Val Cys Pro Gly Val Pro Ala Gly Arg Asp
     50                  55                  60

Pro Arg Glu Pro Asp Pro Lys Val Val Arg Ala
 65                  70                  75

<210> SEQ ID NO 11
<211> LENGTH: 1086
<212> TYPE: DNA
<213> ORGANISM: Zea mays
<220> FEATURE:
<221> NAME/KEY: CDS
<222> LOCATION: (1)...(1086)
<223> OTHER INFORMATION: Brittle-1 without transit peptide

<400> SEQUENCE: 11 gcc gac aac tgc gac atc gcc gcc agc ttg gcg ccg ccg ttc ccg ggc        48
Ala Asp Asn Cys Asp Ile Ala Ala Ser Leu Ala Pro Pro Phe Pro Gly
 1               5                  10                  15 agc agg ccg cct ggg agg cga gga aga ggc agc gaa gag gag gaa gca        96
Ser Arg Pro Pro Gly Arg Arg Gly Arg Gly Ser Glu Glu Glu Glu Ala
             20                  25                  30 gaa ggg cgg cgg cac gaa gaa gca gca gca gct ggg cga tct gag cct       144
Glu Gly Arg Arg His Glu Glu Ala Ala Ala Ala Gly Arg Ser Glu Pro
         35                  40                  45 gag gaa ggt cag ggt caa gat cgc caa ccc gca cct gcg cgc ctg gtt       192
Glu Glu Gly Gln Gly Gln Asp Arg Gln Pro Ala Pro Ala Arg Leu Val
     50                  55                  60
```

```
agc ggc gcc atc gcc ggc gcc gtg tcc agg acg ttt gtg gcg ccg ctg      240
Ser Gly Ala Ile Ala Gly Ala Val Ser Arg Thr Phe Val Ala Pro Leu
 65                  70                  75                  80 gag acg atc cgg acg cac ttg atg gtc ggc agc atc ggc gtc gac tca      288
Glu Thr Ile Arg Thr His Leu Met Val Gly Ser Ile Gly Val Asp Ser
                 85                  90                  95 atg gcc ggg gtg ttc cag tgg atc atg cag aac gaa ggg tgg acc ggc      336
Met Ala Gly Val Phe Gln Trp Ile Met Gln Asn Glu Gly Trp Thr Gly
            100                 105                 110 ctg ttc cgc ggc aac gcc gtc aac gtc ctg cgc gtc gct ccg agc aag      384
Leu Phe Arg Gly Asn Ala Val Asn Val Leu Arg Val Ala Pro Ser Lys
        115                 120                 125 gct atc gag cat ttc acc tat gac acg gcc aag aag ttc cta acc ccc      432
Ala Ile Glu His Phe Thr Tyr Asp Thr Ala Lys Lys Phe Leu Thr Pro
    130                 135                 140 aag ggc gac gag ccg ccc aag atc ccg atc ccc act ccg ctg gtt gcc      480
Lys Gly Asp Glu Pro Pro Lys Ile Pro Ile Pro Thr Pro Leu Val Ala
145                 150                 155                 160 gga gct cta gcc gga ttc gcc tca acc ttg tgc acc tac cca atg gag      528
Gly Ala Leu Ala Gly Phe Ala Ser Thr Leu Cys Thr Tyr Pro Met Glu
                165                 170                 175 ctg atc aag acc agg gtc acc atc gag aag gac gta tac gac aac gtc      576
Leu Ile Lys Thr Arg Val Thr Ile Glu Lys Asp Val Tyr Asp Asn Val
            180                 185                 190 gcg cac gcg ttc gtg aag atc cta cgc gac gag ggc ccg tcg gag ctg      624
Ala His Ala Phe Val Lys Ile Leu Arg Asp Glu Gly Pro Ser Glu Leu
        195                 200                 205 tac cgt ggg ctg aca ccc agc ctg atc ggc gtg gtg ccg tac gcg gcc      672
Tyr Arg Gly Leu Thr Pro Ser Leu Ile Gly Val Val Pro Tyr Ala Ala
    210                 215                 220 tgt aac ttc tac gcc tac gag acg ctg aag cgg ctc tac cgt cgc gcg      720
Cys Asn Phe Tyr Ala Tyr Glu Thr Leu Lys Arg Leu Tyr Arg Arg Ala
225                 230                 235                 240 acc ggg cgg cgt ccc ggc gcg gac gtg ggc ccc gtg gcg acg ctg ctc      768
Thr Gly Arg Arg Pro Gly Ala Asp Val Gly Pro Val Ala Thr Leu Leu
                245                 250                 255 atc ggg tcc gcg gcg ggc gcc atc gcc agc tcg gcc acg ttc ccg cta      816
Ile Gly Ser Ala Ala Gly Ala Ile Ala Ser Ser Ala Thr Phe Pro Leu
            260                 265                 270 gag gtg gcc cgc aag cag atg cag gtg ggc gct gtg ggc ggg agg cag      864
Glu Val Ala Arg Lys Gln Met Gln Val Gly Ala Val Gly Gly Arg Gln
        275                 280                 285 gtg tac cag aac gtc ctc cac gct atc tac tgc atc ctc aag aag gag      912
Val Tyr Gln Asn Val Leu His Ala Ile Tyr Cys Ile Leu Lys Lys Glu
    290                 295                 300 ggc gcc ggc ggc ctg tac cga ggt ctc ggc cct agc tgc atc aag ctc      960
Gly Ala Gly Gly Leu Tyr Arg Gly Leu Gly Pro Ser Cys Ile Lys Leu
305                 310                 315                 320 atg ccc gcc gcc ggc atc gcc ttc atg tgc tac gag gcg tgc aag aag     1008
Met Pro Ala Ala Gly Ile Ala Phe Met Cys Tyr Glu Ala Cys Lys Lys
                325                 330                 335 atc ctc gtc gac aag gag gat gag gag gag gag gac gaa gcc ggc ggc     1056
Ile Leu Val Asp Lys Glu Asp Glu Glu Glu Glu Asp Glu Ala Gly Gly
            340                 345                 350 gga gag gat gac aag aaa aag gtt gaa tga                             1086
Gly Glu Asp Asp Lys Lys Lys Val Glu *
        355                 360

<210> SEQ ID NO 12
```

<211> LENGTH: 361
<212> TYPE: PRT
<213> ORGANISM: Zea mays

<400> SEQUENCE: 12

Ala Asp Asn Cys Asp Ile Ala Ala Ser Leu Ala Pro Phe Pro Gly
1               5                   10                  15

Ser Arg Pro Pro Gly Arg Arg Gly Arg Gly Ser Glu Glu Glu Ala
            20                  25                  30

Glu Gly Arg Arg His Glu Glu Ala Ala Ala Gly Arg Ser Glu Pro
        35                  40                  45

Glu Glu Gly Gln Gly Gln Asp Arg Gln Pro Ala Pro Ala Arg Leu Val
    50                  55                  60

Ser Gly Ala Ile Ala Gly Ala Val Ser Arg Thr Phe Val Ala Pro Leu
65                  70                  75                  80

Glu Thr Ile Arg Thr His Leu Met Val Gly Ser Ile Gly Val Asp Ser
                85                  90                  95

Met Ala Gly Val Phe Gln Trp Ile Met Gln Asn Glu Gly Trp Thr Gly
                100                 105                 110

Leu Phe Arg Gly Asn Ala Val Asn Val Leu Arg Val Ala Pro Ser Lys
            115                 120                 125

Ala Ile Glu His Phe Thr Tyr Asp Thr Ala Lys Lys Phe Leu Thr Pro
        130                 135                 140

Lys Gly Asp Glu Pro Pro Lys Ile Pro Ile Pro Thr Pro Leu Val Ala
145                 150                 155                 160

Gly Ala Leu Ala Gly Phe Ala Ser Thr Leu Cys Thr Tyr Pro Met Glu
                165                 170                 175

Leu Ile Lys Thr Arg Val Thr Ile Glu Lys Asp Val Tyr Asp Asn Val
                180                 185                 190

Ala His Ala Phe Val Lys Ile Leu Arg Asp Glu Gly Pro Ser Glu Leu
            195                 200                 205

Tyr Arg Gly Leu Thr Pro Ser Leu Ile Gly Val Val Pro Tyr Ala Ala
        210                 215                 220

Cys Asn Phe Tyr Ala Tyr Glu Thr Leu Lys Arg Leu Tyr Arg Arg Ala
225                 230                 235                 240

Thr Gly Arg Arg Pro Gly Ala Asp Val Gly Pro Val Ala Thr Leu Leu
                245                 250                 255

Ile Gly Ser Ala Ala Gly Ala Ile Ala Ser Ser Ala Thr Phe Pro Leu
                260                 265                 270

Glu Val Ala Arg Lys Gln Met Gln Val Gly Ala Val Gly Gly Arg Gln
            275                 280                 285

Val Tyr Gln Asn Val Leu His Ala Ile Tyr Cys Ile Leu Lys Lys Glu
        290                 295                 300

Gly Ala Gly Gly Leu Tyr Arg Gly Leu Gly Pro Ser Cys Ile Lys Leu
305                 310                 315                 320

Met Pro Ala Ala Gly Ile Ala Phe Met Cys Tyr Glu Ala Cys Lys Lys
                325                 330                 335

Ile Leu Val Asp Lys Glu Asp Glu Glu Asp Glu Ala Gly Gly
                340                 345                 350

Gly Glu Asp Asp Lys Lys Lys Val Glu
            355                 360

<210> SEQ ID NO 13
<211> LENGTH: 1404
<212> TYPE: DNA

```
<213> ORGANISM: Zea mays
<220> FEATURE:
<221> NAME/KEY: CDS
<222> LOCATION: (1)...(1404)
<223> OTHER INFORMATION: FTsZ2

<400> SEQUENCE: 13 atg gct aca cag ttg cca tgc ttc aca cag ctc agt cca ccg tct tgt      48
Met Ala Thr Gln Leu Pro Cys Phe Thr Gln Leu Ser Pro Pro Ser Cys
 1               5                   10                  15 agt tgg ata aaa gat gtc ggg aac tgc aag gct acg cct gat agg gta      96
Ser Trp Ile Lys Asp Val Gly Asn Cys Lys Ala Thr Pro Asp Arg Val
             20                  25                  30 gcc aga agt gcc cga gct ttg ggc cac tgt cac ttc cgg tgc tgt gca     144
Ala Arg Ser Ala Arg Ala Leu Gly His Cys His Phe Arg Cys Cys Ala
         35                  40                  45 ggc ccc cgt agt gca aac tct ttc aag aag aaa gac tct ttc gag aag     192
Gly Pro Arg Ser Ala Asn Ser Phe Lys Lys Lys Asp Ser Phe Glu Lys
     50                  55                  60 aaa gac tct ttc ctc gaa ctt cat ccg gag gta tct ctg ctc cgt ggc     240
Lys Asp Ser Phe Leu Glu Leu His Pro Glu Val Ser Leu Leu Arg Gly
 65                  70                  75                  80 gag aag agt gcc gag gtt gtg cca atg aaa ggt tcc tct gat ggg ggt     288
Glu Lys Ser Ala Glu Val Val Pro Met Lys Gly Ser Ser Asp Gly Gly
                 85                  90                  95 ctg tta gag gga ctg ggg gtg ccg ccg gac cga aat gat tac agt gag     336
Leu Leu Glu Gly Leu Gly Val Pro Pro Asp Arg Asn Asp Tyr Ser Glu
            100                 105                 110 gct aag atc aag gta gtt gga gtt gga ggc ggg ggt tcg aat gca gtc     384
Ala Lys Ile Lys Val Val Gly Val Gly Gly Gly Gly Ser Asn Ala Val
        115                 120                 125 aat cgg atg att gag agc tcc atg aac ggc gtt gag ttt tgg atc gtg     432
Asn Arg Met Ile Glu Ser Ser Met Asn Gly Val Glu Phe Trp Ile Val
    130                 135                 140 aac act gat gtg cag gcc ata aga atg tct cct gtg ctc ccc cac aat     480
Asn Thr Asp Val Gln Ala Ile Arg Met Ser Pro Val Leu Pro His Asn
145                 150                 155                 160 aga ctg cag att gga cag gag ttg act cga ggc ctg ggc gct ggg gga     528
Arg Leu Gln Ile Gly Gln Glu Leu Thr Arg Gly Leu Gly Ala Gly Gly
                165                 170                 175 aac cct gat att ggg atg aat gca gca aag gag agc agc gag tcc att     576
Asn Pro Asp Ile Gly Met Asn Ala Ala Lys Glu Ser Ser Glu Ser Ile
            180                 185                 190 cag gaa gct ctt ttt ggt gct gac atg gtt ttt gtg acg gct gga atg     624
Gln Glu Ala Leu Phe Gly Ala Asp Met Val Phe Val Thr Ala Gly Met
        195                 200                 205 ggt gga gga act gga act gga ggt gct cct gtg att gct gga ata gcc     672
Gly Gly Gly Thr Gly Thr Gly Gly Ala Pro Val Ile Ala Gly Ile Ala
    210                 215                 220 aag tcc atg ggt ata cta acc gtt ggc ata gtc aca acg cct ttc tcg     720
Lys Ser Met Gly Ile Leu Thr Val Gly Ile Val Thr Thr Pro Phe Ser
225                 230                 235                 240 ttc gag ggg aga aga cgg gca gtt caa gct cag gag gga ata gca gca     768
Phe Glu Gly Arg Arg Arg Ala Val Gln Ala Gln Glu Gly Ile Ala Ala
                245                 250                 255 ttg aga aat agt gtg gac acc cta atc gtc atc cca aat gat aag ttg     816
Leu Arg Asn Ser Val Asp Thr Leu Ile Val Ile Pro Asn Asp Lys Leu
            260                 265                 270 ctg tct gct gtt tct cca aat aca cct gta act gaa gca ttt aat ctg     864
Leu Ser Ala Val Ser Pro Asn Thr Pro Val Thr Glu Ala Phe Asn Leu
        275                 280                 285
```

-continued

```
gct gat gat att ctt cgt caa ggc att cgt ggc ata tct gat ata att    912
Ala Asp Asp Ile Leu Arg Gln Gly Ile Arg Gly Ile Ser Asp Ile Ile
    290                 295                 300 acg gtt cct ggg ttg gtt aat gtt gat ttt gct gac gta cgt gct atc    960
Thr Val Pro Gly Leu Val Asn Val Asp Phe Ala Asp Val Arg Ala Ile
305                 310                 315                 320 atg caa aat gca ggg tca tcc ttg atg ggt ata ggg act gct aca gga   1008
Met Gln Asn Ala Gly Ser Ser Leu Met Gly Ile Gly Thr Ala Thr Gly
                325                 330                 335 aag tca aga gca agg gat gct gct ctt aac gcc atc cag tcg ccg ctg   1056
Lys Ser Arg Ala Arg Asp Ala Ala Leu Asn Ala Ile Gln Ser Pro Leu
            340                 345                 350 ctt gat att gga att gaa aga gcc aca ggc att gtg tgg aat atc act   1104
Leu Asp Ile Gly Ile Glu Arg Ala Thr Gly Ile Val Trp Asn Ile Thr
        355                 360                 365 ggg gga act gac ctg act ttg ttt gag gtg aat gct gcg gcc gaa att   1152
Gly Gly Thr Asp Leu Thr Leu Phe Glu Val Asn Ala Ala Ala Glu Ile
    370                 375                 380 atc tac gac ctt gtc gat cca aac gct aat ctg ata ttt ggc gcc gtc   1200
Ile Tyr Asp Leu Val Asp Pro Asn Ala Asn Leu Ile Phe Gly Ala Val
385                 390                 395                 400 ata gac ccg tca ctg agt ggg cag gtg agc ata acc ttg ata gct act   1248
Ile Asp Pro Ser Leu Ser Gly Gln Val Ser Ile Thr Leu Ile Ala Thr
                405                 410                 415 ggc ttc aaa cgg cag gat gaa cca gaa ggc cgc gtg tcg aag ggt ggg   1296
Gly Phe Lys Arg Gln Asp Glu Pro Glu Gly Arg Val Ser Lys Gly Gly
            420                 425                 430 caa caa ggt gag aat ggc cga cgc cca tcc cca gca gag ggc agc agc   1344
Gln Gln Gly Glu Asn Gly Arg Arg Pro Ser Pro Ala Glu Gly Ser Ser
        435                 440                 445 acg gtg gag atc cca gag ttc ctg cga cga aga gga cct tct cgc ttc   1392
Thr Val Glu Ile Pro Glu Phe Leu Arg Arg Arg Gly Pro Ser Arg Phe
    450                 455                 460 cca cga gtt tga                                                    1404
Pro Arg Val *
465

<210> SEQ ID NO 14
<211> LENGTH: 467
<212> TYPE: PRT
<213> ORGANISM: Zea mays

<400> SEQUENCE: 14

Met Ala Thr Gln Leu Pro Cys Phe Thr Gln Leu Ser Pro Pro Ser Cys
1               5                   10                  15

Ser Trp Ile Lys Asp Val Gly Asn Cys Lys Ala Thr Pro Asp Arg Val
            20                  25                  30

Ala Arg Ser Ala Arg Ala Leu Gly His Cys His Phe Arg Cys Cys Ala
        35                  40                  45

Gly Pro Arg Ser Ala Asn Ser Phe Lys Lys Asp Ser Phe Glu Lys
    50                  55                  60

Lys Asp Ser Phe Leu Glu Leu His Pro Glu Val Ser Leu Leu Arg Gly
65                  70                  75                  80

Glu Lys Ser Ala Glu Val Val Pro Met Lys Gly Ser Ser Asp Gly Gly
                85                  90                  95

Leu Leu Glu Gly Leu Gly Val Pro Pro Asp Arg Asn Asp Tyr Ser Glu
            100                 105                 110

Ala Lys Ile Lys Val Val Gly Val Gly Gly Gly Gly Ser Asn Ala Val
```

```
                115                 120                 125
Asn Arg Met Ile Glu Ser Ser Met Asn Gly Val Glu Phe Trp Ile Val
        130                 135                 140
Asn Thr Asp Val Gln Ala Ile Arg Met Ser Pro Val Leu Pro His Asn
145                 150                 155                 160
Arg Leu Gln Ile Gly Gln Glu Leu Thr Arg Gly Leu Gly Ala Gly Gly
                165                 170                 175
Asn Pro Asp Ile Gly Met Asn Ala Ala Lys Glu Ser Ser Glu Ser Ile
                180                 185                 190
Gln Glu Ala Leu Phe Gly Ala Asp Met Val Phe Val Thr Ala Gly Met
                195                 200                 205
Gly Gly Gly Thr Gly Thr Gly Ala Pro Val Ile Ala Gly Ile Ala
        210                 215                 220
Lys Ser Met Gly Ile Leu Thr Val Gly Ile Val Thr Thr Pro Phe Ser
225                 230                 235                 240
Phe Glu Gly Arg Arg Arg Ala Val Gln Ala Gln Glu Gly Ile Ala Ala
                245                 250                 255
Leu Arg Asn Ser Val Asp Thr Leu Ile Val Ile Pro Asn Asp Lys Leu
        260                 265                 270
Leu Ser Ala Val Ser Pro Asn Thr Pro Val Thr Glu Ala Phe Asn Leu
    275                 280                 285
Ala Asp Asp Ile Leu Arg Gln Gly Ile Arg Gly Ile Ser Asp Ile Ile
        290                 295                 300
Thr Val Pro Gly Leu Val Asn Val Asp Phe Ala Asp Val Arg Ala Ile
305                 310                 315                 320
Met Gln Asn Ala Gly Ser Ser Leu Met Gly Ile Gly Thr Ala Thr Gly
                325                 330                 335
Lys Ser Arg Ala Arg Asp Ala Ala Leu Asn Ala Ile Gln Ser Pro Leu
                340                 345                 350
Leu Asp Ile Gly Ile Glu Arg Ala Thr Gly Ile Val Trp Asn Ile Thr
            355                 360                 365
Gly Gly Thr Asp Leu Thr Leu Phe Glu Val Asn Ala Ala Ala Glu Ile
    370                 375                 380
Ile Tyr Asp Leu Val Asp Pro Asn Ala Asn Leu Ile Phe Gly Ala Val
385                 390                 395                 400
Ile Asp Pro Ser Leu Ser Gly Gln Val Ser Ile Thr Leu Ile Ala Thr
                405                 410                 415
Gly Phe Lys Arg Gln Asp Glu Pro Glu Gly Arg Val Ser Lys Gly Gly
                420                 425                 430
Gln Gln Gly Glu Asn Gly Arg Arg Pro Ser Pro Ala Glu Gly Ser Ser
            435                 440                 445
Thr Val Glu Ile Pro Glu Phe Leu Arg Arg Gly Pro Ser Arg Phe
    450                 455                 460
Pro Arg Val
465

<210> SEQ ID NO 15
<211> LENGTH: 471
<212> TYPE: DNA
<213> ORGANISM: Zea mays
<220> FEATURE:
<221> NAME/KEY: CDS
<222> LOCATION: (1)...(471)
<223> OTHER INFORMATION: Oleosin 16

<400> SEQUENCE: 15
```

```
atg gct gat cac cac cgg ggt gcg acg gga ggt ggc ggg ggc tac ggc      48
Met Ala Asp His His Arg Gly Ala Thr Gly Gly Gly Gly Gly Tyr Gly
 1               5                  10                  15 gac ctc cag cgc ggg ggc ggc atg cac ggc gag gcg cag cag cag cag      96
Asp Leu Gln Arg Gly Gly Gly Met His Gly Glu Ala Gln Gln Gln Gln
             20                  25                  30 aag cag ggc gcc atg atg acg gcg ctc aag gcc gcg acg gcc gcg acc     144
Lys Gln Gly Ala Met Met Thr Ala Leu Lys Ala Ala Thr Ala Ala Thr
         35                  40                  45 ttc ggc ggg tcg atg ctg gtg ctg tcc ggg ctg atc ctg gcc ggc acc     192
Phe Gly Gly Ser Met Leu Val Leu Ser Gly Leu Ile Leu Ala Gly Thr
     50                  55                  60 gtg atc gcg ctc acg gtg gcc acc ccc gtg ctg gtg atc ttc agc ccg     240
Val Ile Ala Leu Thr Val Ala Thr Pro Val Leu Val Ile Phe Ser Pro
 65                  70                  75                  80 gtg ctg gtg ccg gcc gcc atc gcg ctg gcg ctc atg gcg gcc ggg ttc     288
Val Leu Val Pro Ala Ala Ile Ala Leu Ala Leu Met Ala Ala Gly Phe
                 85                  90                  95 gtc acc tcc ggc ggc ctc ggc gtc gct gcg ctg tcc gtg ttc tcc tgg     336
Val Thr Ser Gly Gly Leu Gly Val Ala Ala Leu Ser Val Phe Ser Trp
                100                 105                 110 atg tac aag tac ctg acg ggc aag cac ccg ccg ggc gcc gac cag ctg     384
Met Tyr Lys Tyr Leu Thr Gly Lys His Pro Pro Gly Ala Asp Gln Leu
            115                 120                 125 gac cac gcc aag gcg agg ctg gcg tcc aag gcc cgc gac atc aag gat     432
Asp His Ala Lys Ala Arg Leu Ala Ser Lys Ala Arg Asp Ile Lys Asp
        130                 135                 140 gca gca cag cac cgc atc gac cag gcg cag ggg tct tga                 471
Ala Ala Gln His Arg Ile Asp Gln Ala Gln Gly Ser  *
145                 150                 155

<210> SEQ ID NO 16
<211> LENGTH: 156
<212> TYPE: PRT
<213> ORGANISM: Zea mays

<400> SEQUENCE: 16

Met Ala Asp His His Arg Gly Ala Thr Gly Gly Gly Gly Gly Tyr Gly
 1               5                  10                  15

Asp Leu Gln Arg Gly Gly Gly Met His Gly Glu Ala Gln Gln Gln Gln
             20                  25                  30

Lys Gln Gly Ala Met Met Thr Ala Leu Lys Ala Ala Thr Ala Ala Thr
         35                  40                  45

Phe Gly Gly Ser Met Leu Val Leu Ser Gly Leu Ile Leu Ala Gly Thr
     50                  55                  60

Val Ile Ala Leu Thr Val Ala Thr Pro Val Leu Val Ile Phe Ser Pro
 65                  70                  75                  80

Val Leu Val Pro Ala Ala Ile Ala Leu Ala Leu Met Ala Ala Gly Phe
                 85                  90                  95

Val Thr Ser Gly Gly Leu Gly Val Ala Ala Leu Ser Val Phe Ser Trp
                100                 105                 110

Met Tyr Lys Tyr Leu Thr Gly Lys His Pro Pro Gly Ala Asp Gln Leu
            115                 120                 125

Asp His Ala Lys Ala Arg Leu Ala Ser Lys Ala Arg Asp Ile Lys Asp
        130                 135                 140

Ala Ala Gln His Arg Ile Asp Gln Ala Gln Gly Ser
145                 150                 155
```

-continued

```
<210> SEQ ID NO 17
<211> LENGTH: 1449
<212> TYPE: DNA
<213> ORGANISM: Zea mays
<220> FEATURE:
<221> NAME/KEY: CDS
<222> LOCATION: (1)...(1449)
<223> OTHER INFORMATION: Xylose Isomerase

<400> SEQUENCE: 17 atg aag ggc tgc tca gag cgt ttg ctg ctc ctg ctg ctg gca tcg          48
Met Lys Gly Cys Ser Glu Arg Leu Leu Leu Leu Leu Leu Ala Ser
 1               5                  10                  15 tcg ttg tta ctg tcc gtc gtg gtt gcc gcg cag cag act tgc cct gcc      96
Ser Leu Leu Leu Ser Val Val Val Ala Ala Gln Gln Thr Cys Pro Ala
             20                  25                  30 gac ctc gac agc aaa tgc gac ggt ggc gcg cct gat gac tgg gag ggg    144
Asp Leu Asp Ser Lys Cys Asp Gly Gly Ala Pro Asp Asp Trp Glu Gly
         35                  40                  45 gaa ttc ttc ccc ggc gtc ccg aaa atc aag tat gag ggt cca aca agc    192
Glu Phe Phe Pro Gly Val Pro Lys Ile Lys Tyr Glu Gly Pro Thr Ser
     50                  55                  60 aag aac cct ctt gct tat aag tgg tat aac aag gag gaa gtc att ctc    240
Lys Asn Pro Leu Ala Tyr Lys Trp Tyr Asn Lys Glu Glu Val Ile Leu
 65                  70                  75                  80 gga aag aag atg aag gac tgg atg cgc ttc agt gtt gcg ttc tgg cac    288
Gly Lys Lys Met Lys Asp Trp Met Arg Phe Ser Val Ala Phe Trp His
                 85                  90                  95 acg ttc cgt ggt act ggt gct gat cct ttt ggt gcg cct aca aag gtt    336
Thr Phe Arg Gly Thr Gly Ala Asp Pro Phe Gly Ala Pro Thr Lys Val
            100                 105                 110 tgg cct tgg gag gac ggc aca aat tcg ttg gcc atg gct aag aga aga    384
Trp Pro Trp Glu Asp Gly Thr Asn Ser Leu Ala Met Ala Lys Arg Arg
        115                 120                 125 atg aga gct cac ttt gag ttc atg gag aag ctg ggg gtt gac aaa tgg    432
Met Arg Ala His Phe Glu Phe Met Glu Lys Leu Gly Val Asp Lys Trp
    130                 135                 140 tgc ttc cat gat agg gat att gcc cct gat ggg aaa act ctc gaa gaa    480
Cys Phe His Asp Arg Asp Ile Ala Pro Asp Gly Lys Thr Leu Glu Glu
145                 150                 155                 160 aca aat gct aac ttg gat gag ata gtt gag ctg gca aag cag ctc cag    528
Thr Asn Ala Asn Leu Asp Glu Ile Val Glu Leu Ala Lys Gln Leu Gln
                165                 170                 175 ggt gag acc aat ata aag cca ttg tgg ggt act gca cag ctc ttt atg    576
Gly Glu Thr Asn Ile Lys Pro Leu Trp Gly Thr Ala Gln Leu Phe Met
            180                 185                 190 cat cct cgt tac atg cac gga gct gct act agc cca gag gtt aaa gta    624
His Pro Arg Tyr Met His Gly Ala Ala Thr Ser Pro Glu Val Lys Val
        195                 200                 205 tat gca tat gcg gct gca caa gtt aag aaa gct ttg gag gtc act cac    672
Tyr Ala Tyr Ala Ala Ala Gln Val Lys Lys Ala Leu Glu Val Thr His
    210                 215                 220 tac cta ggt ggt gaa aac tat gtg ttt tgg ggt gga aga gag ggt tac    720
Tyr Leu Gly Gly Glu Asn Tyr Val Phe Trp Gly Gly Arg Glu Gly Tyr
225                 230                 235                 240 caa act ctt ctg aac act gat ctt aag aga gaa ctt gac cat ttg gct    768
Gln Thr Leu Leu Asn Thr Asp Leu Lys Arg Glu Leu Asp His Leu Ala
                245                 250                 255 aac ttt ctt caa gct gct gtt gac tac aag aag aag att gga ttc aac    816
Asn Phe Leu Gln Ala Ala Val Asp Tyr Lys Lys Lys Ile Gly Phe Asn
            260                 265                 270
```

-continued

```
gga aca ctg ttg ata gag cct aaa cca cag gaa cct aca aaa cac cag      864
Gly Thr Leu Leu Ile Glu Pro Lys Pro Gln Glu Pro Thr Lys His Gln
            275                 280                 285 tat gac tgg gat gtt gca act acg ttt gct ttt cta cag aag tat ggt      912
Tyr Asp Trp Asp Val Ala Thr Thr Phe Ala Phe Leu Gln Lys Tyr Gly
290                 295                 300 ctt acc gga gag ttc aag att aat gtt gag tgc aac cat gct act cta      960
Leu Thr Gly Glu Phe Lys Ile Asn Val Glu Cys Asn His Ala Thr Leu
305                 310                 315                 320 tct gga cat agc tgc cat cat gaa ctg gag act gca cgc att aat ggg     1008
Ser Gly His Ser Cys His His Glu Leu Glu Thr Ala Arg Ile Asn Gly
                325                 330                 335 ctg ctt ggg aac att gat gca aac act ggt gat cct caa gtt ggc tgg     1056
Leu Leu Gly Asn Ile Asp Ala Asn Thr Gly Asp Pro Gln Val Gly Trp
            340                 345                 350 gac acg gat cag ttc atg aca gac att gca gag gct act ttg gtt atg     1104
Asp Thr Asp Gln Phe Met Thr Asp Ile Ala Glu Ala Thr Leu Val Met
        355                 360                 365 tca act gtg gtt aag aat ggt gga ctt gca cct ggt ggc ttc aac ttt     1152
Ser Thr Val Val Lys Asn Gly Gly Leu Ala Pro Gly Gly Phe Asn Phe
370                 375                 380 gac gcc aaa ttg cgg agg gaa agc act gat gtt gag gac ttg ttt ctt     1200
Asp Ala Lys Leu Arg Arg Glu Ser Thr Asp Val Glu Asp Leu Phe Leu
385                 390                 395                 400 gct cat atc tcc gga atg gac acc ctg gcc cgt ggc ctc cgc aac gcc     1248
Ala His Ile Ser Gly Met Asp Thr Leu Ala Arg Gly Leu Arg Asn Ala
                405                 410                 415 gcc aag ctg atc gag gat ggt tcc cta gat gct ctc gtc cgc aag cgg     1296
Ala Lys Leu Ile Glu Asp Gly Ser Leu Asp Ala Leu Val Arg Lys Arg
            420                 425                 430 tac cag agc ttt gat agt gag att ggt gcc ttg atc gag gct ggg aaa     1344
Tyr Gln Ser Phe Asp Ser Glu Ile Gly Ala Leu Ile Glu Ala Gly Lys
        435                 440                 445 gga gac ttt gag gcg cta gag aag aag gtc ctt gag tgg ggt gag ccc     1392
Gly Asp Phe Glu Ala Leu Glu Lys Lys Val Leu Glu Trp Gly Glu Pro
450                 455                 460 act gtt ccg tcc ggc aaa cag gaa ctg gcg gag att ctg ttc cac tct     1440
Thr Val Pro Ser Gly Lys Gln Glu Leu Ala Glu Ile Leu Phe His Ser
465                 470                 475                 480 gct cta tag                                                         1449
Ala Leu *
```

<210> SEQ ID NO 18
<211> LENGTH: 482
<212> TYPE: PRT
<213> ORGANISM: Zea mays

<400> SEQUENCE: 18

```
Met Lys Gly Cys Ser Glu Arg Leu Leu Leu Leu Leu Leu Ala Ser
1               5                   10                  15

Ser Leu Leu Leu Ser Val Val Ala Ala Gln Gln Thr Cys Pro Ala
            20                  25                  30

Asp Leu Asp Ser Lys Cys Asp Gly Ala Pro Asp Asp Trp Glu Gly
        35                  40                  45

Glu Phe Phe Pro Gly Val Pro Lys Ile Lys Tyr Glu Gly Pro Thr Ser
    50                  55                  60

Lys Asn Pro Leu Ala Tyr Lys Trp Tyr Asn Lys Glu Glu Val Ile Leu
65                  70                  75                  80
```

-continued

```
Gly Lys Lys Met Lys Asp Trp Met Arg Phe Ser Val Ala Phe Trp His
             85                  90                  95

Thr Phe Arg Gly Thr Gly Ala Asp Pro Phe Gly Ala Pro Thr Lys Val
            100                 105                 110

Trp Pro Trp Glu Asp Gly Thr Asn Ser Leu Ala Met Ala Lys Arg Arg
            115                 120                 125

Met Arg Ala His Phe Glu Phe Met Glu Lys Leu Gly Val Asp Lys Trp
130                 135                 140

Cys Phe His Asp Arg Asp Ile Ala Pro Asp Gly Lys Thr Leu Glu Glu
145                 150                 155                 160

Thr Asn Ala Asn Leu Asp Glu Ile Val Glu Leu Ala Lys Gln Leu Gln
                165                 170                 175

Gly Glu Thr Asn Ile Lys Pro Leu Trp Gly Thr Ala Gln Leu Phe Met
            180                 185                 190

His Pro Arg Tyr Met His Gly Ala Ala Thr Ser Pro Glu Val Lys Val
            195                 200                 205

Tyr Ala Tyr Ala Ala Gln Val Lys Lys Ala Leu Glu Val Thr His
210                 215                 220

Tyr Leu Gly Gly Glu Asn Tyr Val Phe Trp Gly Gly Arg Glu Gly Tyr
225                 230                 235                 240

Gln Thr Leu Leu Asn Thr Asp Leu Lys Arg Glu Leu Asp His Leu Ala
                245                 250                 255

Asn Phe Leu Gln Ala Ala Val Asp Tyr Lys Lys Ile Gly Phe Asn
            260                 265                 270

Gly Thr Leu Leu Ile Glu Pro Lys Pro Gln Glu Pro Thr Lys His Gln
            275                 280                 285

Tyr Asp Trp Asp Val Ala Thr Thr Phe Ala Phe Leu Gln Lys Tyr Gly
290                 295                 300

Leu Thr Gly Glu Phe Lys Ile Asn Val Glu Cys Asn His Ala Thr Leu
305                 310                 315                 320

Ser Gly His Ser Cys His His Glu Leu Glu Thr Ala Arg Ile Asn Gly
                325                 330                 335

Leu Leu Gly Asn Ile Asp Ala Asn Thr Gly Asp Pro Gln Val Gly Trp
            340                 345                 350

Asp Thr Asp Gln Phe Met Thr Asp Ile Ala Glu Ala Thr Leu Val Met
            355                 360                 365

Ser Thr Val Val Lys Asn Gly Gly Leu Ala Pro Gly Gly Phe Asn Phe
370                 375                 380

Asp Ala Lys Leu Arg Arg Glu Ser Thr Asp Val Glu Asp Leu Phe Leu
385                 390                 395                 400

Ala His Ile Ser Gly Met Asp Thr Leu Ala Arg Gly Leu Arg Asn Ala
                405                 410                 415

Ala Lys Leu Ile Glu Asp Gly Ser Leu Asp Ala Leu Val Arg Lys Arg
            420                 425                 430

Tyr Gln Ser Phe Asp Ser Glu Ile Gly Ala Leu Ile Glu Ala Gly Lys
            435                 440                 445

Gly Asp Phe Glu Ala Leu Glu Lys Lys Val Leu Glu Trp Gly Glu Pro
450                 455                 460

Thr Val Pro Ser Gly Lys Gln Glu Leu Ala Glu Ile Leu Phe His Ser
465                 470                 475                 480

Ala Leu
```

<210> SEQ ID NO 19

```
<211> LENGTH: 837
<212> TYPE: DNA
<213> ORGANISM: Zea mays
<220> FEATURE:
<221> NAME/KEY: CDS
<222> LOCATION: (1)...(837)
<223> OTHER INFORMATION: Lec1

<400> SEQUENCE: 19 atg gac tcc agc agc ttc ctc cct gcc gcc ggc gcg gag aat ggc tcg        48
Met Asp Ser Ser Ser Phe Leu Pro Ala Ala Gly Ala Glu Asn Gly Ser
 1               5                  10                  15 gcg gcg ggc ggc gcc aac aat ggc ggc gct gct cag cag cat gcg gcg        96
Ala Ala Gly Gly Ala Asn Asn Gly Gly Ala Ala Gln Gln His Ala Ala
             20                  25                  30 ccg gcg atc cgc gag cag gac cgg ctg atg ccg atc gcg aac gtg atc       144
Pro Ala Ile Arg Glu Gln Asp Arg Leu Met Pro Ile Ala Asn Val Ile
         35                  40                  45 cgc atc atg cgg cgc gtg ctg ccg gcg cac gcc aag atc tcg gac gac       192
Arg Ile Met Arg Arg Val Leu Pro Ala His Ala Lys Ile Ser Asp Asp
     50                  55                  60 gcc aag gag acg atc cag gag tgc gtg tcg gag tac atc agc ttc atc       240
Ala Lys Glu Thr Ile Gln Glu Cys Val Ser Glu Tyr Ile Ser Phe Ile
 65                  70                  75                  80 acg ggg gag gcc aac gag cgg tgc cag cgg gag cag cgc aag acc atc       288
Thr Gly Glu Ala Asn Glu Arg Cys Gln Arg Glu Gln Arg Lys Thr Ile
                 85                  90                  95 acc gcc gag gac gtg ctg tgg gcc atg agc cgc ctc ggc ttc gac gac       336
Thr Ala Glu Asp Val Leu Trp Ala Met Ser Arg Leu Gly Phe Asp Asp
            100                 105                 110 tac gtc gag ccg ctc ggc gcc tac ctc cac cgc tac cgc gag ttc gag       384
Tyr Val Glu Pro Leu Gly Ala Tyr Leu His Arg Tyr Arg Glu Phe Glu
        115                 120                 125 ggc gac gcg cgc ggc gtc ggg ctc gtc ccg ggg gcc gcc cca tcg cgc       432
Gly Asp Ala Arg Gly Val Gly Leu Val Pro Gly Ala Ala Pro Ser Arg
    130                 135                 140 ggc ggc gac cac cac ccg cac tcc atg tcg cca gcg gcg atg ctc aag       480
Gly Gly Asp His His Pro His Ser Met Ser Pro Ala Ala Met Leu Lys
145                 150                 155                 160 tcc cgc ggg cca gtc tcc gga gcc gcc atg cta ccg cac cac cac cac       528
Ser Arg Gly Pro Val Ser Gly Ala Ala Met Leu Pro His His His His
                165                 170                 175 cac cac gac atg cag atg cac gcc gcc atg tac ggg gga acg gcc gtg       576
His His Asp Met Gln Met His Ala Ala Met Tyr Gly Gly Thr Ala Val
            180                 185                 190 ccc ccg ccg gcc ggg cct cct cac cac ggc ggg ttc ctc atg cca cac       624
Pro Pro Pro Ala Gly Pro Pro His His Gly Gly Phe Leu Met Pro His
        195                 200                 205 cca cag ggt agt agc cac tac ctg cct tac gcg tac gag ccc acg tac       672
Pro Gln Gly Ser Ser His Tyr Leu Pro Tyr Ala Tyr Glu Pro Thr Tyr
    210                 215                 220 ggc ggt gag cac gcc atg gct gca tac tat gga ggc gcc gcg tac gcg       720
Gly Gly Glu His Ala Met Ala Ala Tyr Tyr Gly Gly Ala Ala Tyr Ala
225                 230                 235                 240 ccc ggc aac ggc ggg agc ggc gac ggc agt ggc agt ggc ggc ggt ggc       768
Pro Gly Asn Gly Gly Ser Gly Asp Gly Ser Gly Ser Gly Gly Gly Gly
                245                 250                 255 ggg agc gcg tcg cac aca ccg cag ggc agc ggc ggc ttg gag cac ccg       816
Gly Ser Ala Ser His Thr Pro Gln Gly Ser Gly Gly Leu Glu His Pro
            260                 265                 270 cac ccg ttc gcg tac aag tag                                           837
```

His Pro Phe Ala Tyr Lys  *
        275

<210> SEQ ID NO 20
<211> LENGTH: 278
<212> TYPE: PRT
<213> ORGANISM: Zea mays

<400> SEQUENCE: 20

Met Asp Ser Ser Ser Phe Leu Pro Ala Ala Gly Ala Glu Asn Gly Ser
1               5                   10                  15

Ala Ala Gly Gly Ala Asn Asn Gly Gly Ala Ala Gln Gln His Ala Ala
            20                  25                  30

Pro Ala Ile Arg Glu Gln Asp Arg Leu Met Pro Ile Ala Asn Val Ile
        35                  40                  45

Arg Ile Met Arg Arg Val Leu Pro Ala His Ala Lys Ile Ser Asp Asp
50                  55                  60

Ala Lys Glu Thr Ile Gln Glu Cys Val Ser Glu Tyr Ile Ser Phe Ile
65                  70                  75                  80

Thr Gly Glu Ala Asn Glu Arg Cys Gln Arg Glu Gln Arg Lys Thr Ile
                85                  90                  95

Thr Ala Glu Asp Val Leu Trp Ala Met Ser Arg Leu Gly Phe Asp Asp
            100                 105                 110

Tyr Val Glu Pro Leu Gly Ala Tyr Leu His Arg Tyr Arg Glu Phe Glu
        115                 120                 125

Gly Asp Ala Arg Gly Val Gly Leu Val Pro Gly Ala Ala Pro Ser Arg
130                 135                 140

Gly Gly Asp His His Pro His Ser Met Ser Pro Ala Ala Met Leu Lys
145                 150                 155                 160

Ser Arg Gly Pro Val Ser Gly Ala Ala Met Leu Pro His His His
                165                 170                 175

His His Asp Met Gln Met His Ala Ala Met Tyr Gly Gly Thr Ala Val
            180                 185                 190

Pro Pro Pro Ala Gly Pro Pro His His Gly Gly Phe Leu Met Pro His
        195                 200                 205

Pro Gln Gly Ser Ser His Tyr Leu Pro Tyr Ala Tyr Glu Pro Thr Tyr
    210                 215                 220

Gly Gly Glu His Ala Met Ala Ala Tyr Tyr Gly Gly Ala Ala Tyr Ala
225                 230                 235                 240

Pro Gly Asn Gly Gly Ser Gly Asp Gly Ser Gly Ser Gly Gly Gly Gly
                245                 250                 255

Gly Ser Ala Ser His Thr Pro Gln Gly Ser Gly Gly Leu Glu His Pro
            260                 265                 270

His Pro Phe Ala Tyr Lys
        275

<210> SEQ ID NO 21
<211> LENGTH: 392
<212> TYPE: PRT
<213> ORGANISM: Arabidopsis thaliana

<400> SEQUENCE: 21

Met Gly Lys Thr Gly Ile Gln Leu Phe Asp Asp Ser Arg Asn Gly Phe
1               5                   10                  15

Phe Ser Val Ser Asp Leu Gly Phe Asp Ser Ser Leu Asn Ser Ser Asn
            20                  25                  30

-continued

```
Tyr His Pro Ile Gly Gly Leu Phe Ala Ser Val Asn Gln Thr Asn Pro
        35                  40                  45

Phe Ala Ser Leu Ser Ser Ser Asp Leu Ser Asn Arg Gly Asn Asn Ser
 50                  55                  60

Phe Ser Thr Gln Leu Asn Asp Leu Tyr Thr Lys Tyr Met Pro Gly Lys
 65                  70                  75                  80

Glu Glu Glu Glu Glu Val Val Asn Gly Glu Lys Arg Lys Arg Lys Lys
                 85                  90                  95

Lys Gly Gly Leu Thr Leu Lys Ile Lys Ile Ala Asn Pro Ser Leu Arg
             100                 105                 110

Arg Leu Leu Ser Gly Ala Val Ala Gly Ala Val Ser Arg Thr Val Val
             115                 120                 125

Ala Pro Leu Glu Thr Ile Arg Thr His Leu Met Val Gly Ser Gly Gly
 130                 135                 140

Asn Ser Ser Thr Glu Val Phe Ser Asp Ile Met Lys His Glu Gly Trp
 145                 150                 155                 160

Thr Gly Leu Phe Arg Gly Asn Leu Val Asn Val Ile Arg Val Ala Pro
                 165                 170                 175

Ala Arg Ala Val Glu Leu Phe Val Phe Glu Thr Val Asn Lys Lys Leu
             180                 185                 190

Ser Pro Pro His Gly Gln Glu Ser Lys Ile Pro Ile Pro Ala Ser Leu
             195                 200                 205

Leu Ala Gly Ala Cys Ala Gly Val Ser Gln Thr Leu Leu Thr Tyr Pro
 210                 215                 220

Leu Glu Leu Val Lys Thr Arg Leu Thr Ile Gln Arg Gly Val Tyr Lys
225                 230                 235                 240

Gly Ile Phe Asp Ala Phe Leu Lys Ile Ile Arg Glu Glu Gly Pro Thr
                 245                 250                 255

Glu Leu Tyr Arg Gly Leu Ala Pro Ser Leu Ile Gly Val Val Pro Tyr
             260                 265                 270

Ala Ala Thr Asn Tyr Phe Ala Tyr Asp Ser Leu Arg Lys Ala Tyr Arg
             275                 280                 285

Ser Phe Ser Lys Gln Glu Lys Ile Gly Asn Ile Glu Thr Leu Leu Ile
290                 295                 300

Gly Ser Leu Ala Gly Ala Leu Ser Ser Thr Ala Thr Phe Pro Leu Glu
305                 310                 315                 320

Val Ala Arg Lys His Met Gln Val Gly Ala Val Ser Gly Arg Val Val
                 325                 330                 335

Tyr Lys Asn Met Leu His Ala Leu Val Thr Ile Leu Glu His Glu Gly
             340                 345                 350

Ile Leu Gly Trp Tyr Lys Gly Leu Gly Pro Ser Cys Leu Lys Leu Val
             355                 360                 365

Pro Ala Ala Gly Ile Ser Phe Met Cys Tyr Glu Ala Cys Lys Lys Ile
 370                 375                 380

Leu Ile Glu Asn Asn Gln Glu Ala
385                 390
```

<210> SEQ ID NO 22
<211> LENGTH: 5
<212> TYPE: PRT
<213> ORGANISM: Artificial Sequence
<220> FEATURE:
<223> OTHER INFORMATION: Motif common to the ADP-glucose-binding site of
      starch synthases and bacterial glycogen synthases

<400> SEQUENCE: 22

-continued

```
Lys Thr Gly Gly Leu
  1               5

<210> SEQ ID NO 23
<211> LENGTH: 147
<212> TYPE: PRT
<213> ORGANISM: Zea mays

<400> SEQUENCE: 23

Arg Gly Gly Gly Tyr Gly Asp Leu Gln Arg Gly Gly Met His
  1               5                  10                  15

Gly Glu Ala Gln Gln Gln Lys Gln Gly Ala Met Met Thr Ala Leu
                 20                  25                  30

Lys Ala Ala Thr Ala Ala Thr Phe Gly Gly Ser Met Leu Val Leu Ser
         35                  40                  45

Gly Leu Ile Leu Ala Gly Thr Val Ile Ala Leu Thr Val Ala Thr Pro
     50                  55                  60

Val Leu Val Ile Phe Ser Pro Val Leu Val Pro Ala Ala Ile Ala Leu
 65                  70                  75                  80

Ala Leu Met Ala Ala Gly Phe Val Thr Ser Gly Gly Leu Gly Val Ala
                 85                  90                  95

Ala Leu Ser Val Phe Ser Trp Met Tyr Lys Tyr Leu Thr Gly Lys His
                100                 105                 110

Pro Pro Gly Ala Asp Gln Leu Asp His Ala Lys Ala Arg Leu Ala Ser
            115                 120                 125

Lys Ala Arg Asp Ile Lys Asp Ala Ala Gln His Arg Ile Asp Gln Ala
        130                 135                 140

Gln Gly Ser
145

<210> SEQ ID NO 24
<211> LENGTH: 148
<212> TYPE: PRT
<213> ORGANISM: Oryza sativa

<400> SEQUENCE: 24

Met Ala Asp Gln His Arg Gly Val Ile Gly Gly Gly Tyr Gly Asp
  1               5                  10                  15

Arg Gly Gly Gln Glu Gln Gln Glu Lys Gln Pro Phe Met Met Thr Ala
                 20                  25                  30

Leu Lys Thr Val Thr Ala Ala Thr Ala Gly Gly Ser Met Leu Val Leu
         35                  40                  45

Ser Gly Leu Ile Leu Ala Gly Thr Val Ile Ala Leu Thr Val Ala Thr
     50                  55                  60

Pro Val Leu Val Ile Phe Ser Pro Val Leu Val Pro Ala Ala Ile Ala
 65                  70                  75                  80

Leu Ala Leu Met Ala Ala Gly Phe Val Thr Ser Gly Gly Leu Gly Val
                 85                  90                  95

Ala Ala Leu Ser Val Phe Ser Trp Met Tyr Lys Tyr Leu Thr Gly Lys
                100                 105                 110

His Pro Pro Gly Ala Asp Gln Leu Asp His Ala Lys Ala Arg Leu Ala
            115                 120                 125

Ser Lys Ala Arg Asp Ile Lys Glu Ala Ala Gln His Arg Ile Asp Gln
        130                 135                 140

Ala Gln Ala Ser
145
```

<210> SEQ ID NO 25
<211> LENGTH: 158
<212> TYPE: PRT
<213> ORGANISM: Hordeum vulgare

<400> SEQUENCE: 25

```
Met Ala Ala Glu His His Arg Asp Arg Gly Val Leu Gly Gly Gly
 1               5                  10                  15

Ala Phe Ala Asp Arg Ser Gly Gln Gly Gly Tyr Gly Gly Asp His His
                20                  25                  30

Asp Gln Gln Lys Gln Pro Ala Met Met Cys Ala Leu Lys Ala Ala Thr
            35                  40                  45

Ala Thr Ala Ala Gly Ser Leu Leu Val Leu Ser Gly Leu Ile Leu Ala
        50                  55                  60

Gly Thr Val Ile Ala Leu Thr Val Ala Thr Pro Val Leu Val Ile Phe
65                  70                  75                  80

Ser Pro Val Leu Val Pro Ala Ala Ile Ala Leu Ala Leu Met Ser Ala
                85                  90                  95

Gly Phe Val Thr Ser Gly Gly Leu Gly Val Ala Ala Leu Ser Val Phe
            100                 105                 110

Ser Trp Met Tyr Lys Tyr Leu Thr Gly Lys His Pro Pro Gly Ala Asp
        115                 120                 125

Gln Leu Asp His Ala Lys Ala Arg Leu Ala Ser Lys Ala Arg Asp Ile
    130                 135                 140

Lys Asp Ala Ala Gln Thr Arg Ile Asp Gln Ala Gln Gly Ala
145                 150                 155
```

<210> SEQ ID NO 26
<211> LENGTH: 167
<212> TYPE: PRT
<213> ORGANISM: Bromus secalinus

<400> SEQUENCE: 26

```
Met Ala Asp His His Arg Asp Arg Gly Val Leu Gly Gly Gly Ala Leu
 1               5                  10                  15

Gly Glu Arg Gly Ser His Gly Gly Tyr Gly Tyr Thr Gly Asp His Gly
                20                  25                  30

Gly Tyr Gly Gly Asp Asp Glu Gln His Gln Lys Gln Pro Val Met
            35                  40                  45

Met Cys Ala Leu Lys Ala Ala Thr Ala Ala Thr Ala Gly Gly Ser Met
        50                  55                  60

Leu Val Leu Ser Gly Leu Ile Leu Ala Gly Thr Val Ile Ala Leu Thr
65                  70                  75                  80

Val Ala Thr Pro Val Leu Val Ile Phe Ser Pro Val Leu Val Pro Ala
                85                  90                  95

Ala Ile Ser Met Ala Leu Met Ser Ala Gly Phe Val Thr Ser Gly Gly
            100                 105                 110

Leu Gly Val Ala Ala Val Ser Val Phe Ser Trp Met Tyr Lys Tyr Leu
        115                 120                 125

Ala Gly Lys His Pro Pro Gly Ala Asp Gln Leu Asp His Ala Lys Ala
    130                 135                 140

Arg Leu Ala Ser Lys Ala Arg Asp Ile Lys Asp Ala Ala Gln Ile Arg
145                 150                 155                 160

Val Glu Gln Ala Gln Gly Ala
                165
```

<210> SEQ ID NO 27
<211> LENGTH: 751
<212> TYPE: PRT
<213> ORGANISM: Manihot esculenta

<400> SEQUENCE: 27

```
Met Ala Phe Ile Gly Ser Leu Pro Phe Ile Ile Gln Thr Lys Ala Glu
 1               5                  10                  15

Ser Ser Val Leu Leu His Asp Lys Asn Leu Gln Arg Ser Arg Phe Ser
             20                  25                  30

Val Phe Pro Cys Arg Ser Gln Asn Ser Phe Asn Leu Ala Val Ser Leu
         35                  40                  45

Ser Leu Ser Phe Lys Pro Val Arg Ala Thr Gly Lys Glu Gly Val Ser
 50                  55                  60

Gly Asp Gly Ser Glu Asp Thr Leu Gln Ala Thr Ile Glu Lys Ser Lys
 65                  70                  75                  80

Lys Val Leu Ala Leu Gln Arg Asp Leu Leu Gln Lys Ile Ala Glu Arg
                 85                  90                  95

Arg Lys Leu Val Ser Ser Ile Gln Ser Val Gly Asp His Asp Thr
            100                 105                 110

Asn Lys Thr Ser His Glu Gln Arg Glu Asn Ser Leu Ala Asn Ser Asp
        115                 120                 125

Asn Thr Ser Thr Ser Asp Val Asn Met His Gln Gln Asn Gly Pro
130                 135                 140

Val Leu Pro Ser Ser Tyr Val His Ser Thr Ala Asp Glu Val Ser Glu
145                 150                 155                 160

Thr Ala Ser Ser Ala Ile Asn Arg Gly His Ala Lys Asp Asp Lys Glu
                165                 170                 175

Leu Glu Gln His Ala Ser Pro Arg Thr Ala Phe Val Lys Asn Ser Thr
            180                 185                 190

Lys Gln Phe Lys Glu Met Asp Ser Glu Lys Leu Gln Thr Asp Glu Ile
        195                 200                 205

Pro Ser Phe Leu Ser Asn Thr Thr Asp Ile Ser Thr Ile Asn Glu Glu
210                 215                 220

Asn Ser Glu His Ser Asn Glu Ser Thr Ser Pro Met Val Asp Ile Phe
225                 230                 235                 240

Glu Ser Asp Ser Met Thr Glu Asp Met Lys Pro Pro Leu Ala Gly
                245                 250                 255

Asp Asn Val Met Asn Val Ile Leu Val Ala Ala Glu Cys Ala Pro Trp
            260                 265                 270

Ser Lys Thr Gly Gly Leu Gly Asp Val Ala Gly Ser Leu Pro Lys Ala
        275                 280                 285

Leu Ala Arg Arg Gly His Arg Val Met Val Val Ala Pro Arg Tyr Gly
290                 295                 300

Asn Tyr Val Glu Pro Gln Asp Thr Gly Val Arg Lys Arg Tyr Lys Val
305                 310                 315                 320

Asp Gly Gln Asp Phe Glu Val Ser Tyr Phe Gln Ala Phe Ile Asp Gly
                325                 330                 335

Val Asp Phe Val Phe Ile Asp Ser Pro Met Phe Arg His Ile Gly Asn
            340                 345                 350

Asp Ile Tyr Gly Gly Asn Arg Met Asp Ile Leu Lys Arg Met Val Leu
        355                 360                 365

Phe Cys Lys Ala Ala Val Glu Val Pro Trp His Val Pro Cys Gly Gly
```

```
                    370             375             380
Val Cys Tyr Gly Asp Gly Asn Leu Ala Phe Ile Ala Asn Asp Trp His
385                     390                 395                 400

Thr Ala Leu Leu Pro Val Tyr Leu Lys Ala Tyr Tyr Arg Asp Asn Gly
                405                 410                 415

Leu Met Gln Tyr Thr Arg Ser Val Leu Val Ile His Asn Ile Ala His
                420                 425                 430

Gln Gly Arg Gly Pro Ser Gly Asp Phe Ser Tyr Val Gly Leu Pro Glu
                435                 440                 445

His Tyr Ile Asp Leu Phe Lys Leu His Asp Pro Ile Gly Gly Asp His
            450                 455                 460

Phe Asn Ile Phe Ala Pro Gly Leu Lys Val Ala Asp Arg Val Val Thr
465                 470                 475                 480

Val Ser His Gly Tyr Ala Trp Glu Leu Lys Thr Ser Glu Gly Gly Trp
                485                 490                 495

Gly Leu His Asn Ile Ile Asn Glu Asn His Trp Lys Leu Gln Gly Ile
            500                 505                 510

Val Asn Gly Ile Asp Ala Lys Glu Trp Asn Pro Gln Phe Asp Ile Gln
            515                 520                 525

Leu Thr Ser Asp Gly Tyr Thr Asn Tyr Ser Leu Glu Thr Leu Asp Thr
            530                 535                 540

Gly Lys Pro Gln Cys Lys Thr Ala Leu Gln Asn Glu Leu Arg Phe Ala
545                 550                 555                 560

Ile Pro Pro Asp Val Pro Val Ile Gly Phe Ile Gly Arg Leu Asp Tyr
                565                 570                 575

Gln Lys Gly Val Asp Leu Ile Ala Glu Ala Ile Pro Trp Met Val Gly
                580                 585                 590

Gln Asp Val Gln Leu Val Met Leu Gly Thr Gly Arg Gln Asp Leu Glu
            595                 600                 605

Glu Met Leu Arg Gln Phe Glu Asn Gln His Arg Asp Lys Val Arg Gly
            610                 615                 620

Trp Val Gly Phe Ser Val Lys Thr Ala His Arg Ile Thr Ala Gly Ala
625                 630                 635                 640

Asp Ile Leu Leu Met Pro Ser Arg Phe Glu Pro Cys Gly Leu Asn Gln
                645                 650                 655

Leu Tyr Ala Met Met Tyr Gly Thr Ile Pro Val Val His Ala Val Gly
                660                 665                 670

Gly Leu Arg Asp Thr Val Gln Pro Phe Asp Pro Phe Asn Glu Ser Gly
                675                 680                 685

Leu Gly Trp Thr Phe Asp Ser Ala Glu Ser His Lys Leu Ile His Ala
            690                 695                 700

Leu Gly Asn Cys Leu Leu Thr Tyr Arg Glu Tyr Lys Lys Ser Trp Glu
705                 710                 715                 720

Gly Leu Gln Arg Arg Gly Met Thr Pro Asn Leu Ser Trp Asp His Ala
                725                 730                 735

Ala Glu Lys Tyr Glu Glu Thr Leu Val Ala Ala Lys Tyr Gln Trp
                740                 745                 750

<210> SEQ ID NO 28
<211> LENGTH: 752
<212> TYPE: PRT
<213> ORGANISM: Pisum sativum

<400> SEQUENCE: 28
```

```
Met Met Leu Ser Leu Gly Ser Asp Ala Thr Val Leu Pro Phe His Ala
  1               5                  10                  15

Lys Asn Leu Lys Phe Thr Pro Lys Leu Ser Thr Leu Asn Gly Asp Leu
                 20                  25                  30

Ala Phe Ser Lys Gly Leu Gly Val Gly Arg Leu Asn Cys Gly Ser Val
             35                  40                  45

Arg Leu Asn His Lys Gln His Val Arg Ala Val Gly Lys Ser Phe Gly
         50                  55                  60

Ala Asp Glu Asn Gly Asp Gly Ser Glu Asp Asp Val Val Asn Ala Thr
 65                  70                  75                  80

Ile Glu Lys Ser Lys Arg Phe Leu Leu Cys Lys Gly Asn Leu Phe Asn
                 85                  90                  95

Arg Leu Leu Lys Glu Arg Asn Leu Val Ser Ser Ile Asp Ser Asp Ser
             100                 105                 110

Ile Pro Gly Leu Glu Gly Asn Gly Val Ser Tyr Glu Ser Ser Glu Lys
             115                 120                 125

Ser Leu Ser Arg Asp Ser Asn Pro Gln Lys Gly Leu Pro Ala Ala Ala
     130                 135                 140

Val Leu Leu Lys Pro Asn Gly Gly Thr Val Phe Ser Asn Tyr Val Arg
145                 150                 155                 160

Ser Lys Glu Thr Glu Thr Trp Ala Val Ser Ser Val Gly Ile Asn Gln
                 165                 170                 175

Gly Phe Asp Glu Ile Glu Lys Lys Asn Asp Ala Val Lys Ala Ser Ser
             180                 185                 190

Lys Leu His Phe Asn Glu Gln Ile Lys Asn Lys Leu Tyr Glu Arg Pro
         195                 200                 205

Asp Thr Lys Asp Ile Ser Ser Ser Ile Arg Thr Ser Ser Leu Lys Phe
     210                 215                 220

Glu Asn Phe Glu Gly Ala Asn Glu Pro Ser Ser Lys Glu Val Ala Asn
225                 230                 235                 240

Glu Ala Glu Asn Phe Glu Ser Gly Gly Glu Lys Pro Pro Pro Leu Ala
                 245                 250                 255

Gly Thr Asn Val Met Asn Ile Ile Leu Val Ser Ala Glu Cys Ala Pro
             260                 265                 270

Trp Ser Lys Thr Gly Gly Leu Gly Asp Val Ala Gly Ser Leu Pro Lys
         275                 280                 285

Ala Leu Ala Arg Arg Gly His Arg Val Met Ile Val Ala Pro His Tyr
     290                 295                 300

Gly Asn Tyr Ala Glu Ala His Asp Ile Gly Val Arg Lys Arg Tyr Lys
305                 310                 315                 320

Val Ala Gly Gln Asp Met Glu Val Thr Tyr Phe His Thr Tyr Ile Asp
                 325                 330                 335

Gly Val Asp Ile Val Phe Ile Asp Ser Pro Ile Phe Arg Asn Leu Glu
             340                 345                 350

Ser Asn Ile Tyr Gly Gly Asn Arg Leu Asp Ile Leu Arg Arg Met Val
         355                 360                 365

Leu Phe Cys Lys Ala Ala Val Glu Val Pro Trp His Val Pro Cys Gly
     370                 375                 380

Gly Ile Cys Tyr Gly Asp Gly Asn Leu Val Phe Ile Ala Asn Asp Trp
385                 390                 395                 400

His Thr Ala Leu Leu Pro Val Tyr Leu Lys Ala Tyr Tyr Arg Asp His
                 405                 410                 415

Gly Leu Met Asn Tyr Thr Arg Ser Val Leu Val Ile His Asn Ile Ala
```

```
                420             425             430
His Gln Gly Arg Gly Pro Val Glu Asp Phe Asn Thr Val Asp Leu Ser
            435                 440                 445
Gly Asn Tyr Leu Asp Leu Phe Lys Met Tyr Asp Pro Val Gly Gly Glu
        450                 455                 460
His Phe Asn Ile Phe Ala Ala Gly Leu Lys Thr Ala Asp Arg Ile Val
465                 470                 475                 480
Thr Val Ser His Gly Tyr Ala Trp Glu Leu Lys Thr Ser Glu Gly Gly
                485                 490                 495
Trp Gly Leu His Asn Ile Ile Asn Glu Ser Asp Trp Lys Phe Arg Gly
                500                 505                 510
Ile Val Asn Gly Val Asp Thr Lys Asp Trp Asn Pro Gln Phe Asp Ala
                515                 520                 525
Tyr Leu Thr Ser Asp Gly Tyr Thr Asn Tyr Asn Leu Lys Thr Leu Gln
            530                 535                 540
Thr Gly Lys Arg Gln Cys Lys Ala Ala Leu Gln Arg Glu Leu Gly Leu
545                 550                 555                 560
Pro Val Arg Glu Asp Val Pro Ile Ile Ser Phe Ile Gly Arg Leu Asp
                565                 570                 575
His Gln Lys Gly Val Asp Leu Ile Ala Glu Ala Ile Pro Trp Met Met
            580                 585                 590
Ser His Asp Val Gln Leu Val Met Leu Gly Thr Gly Arg Ala Asp Leu
        595                 600                 605
Glu Gln Met Leu Lys Glu Phe Glu Ala Gln His Cys Asp Lys Ile Arg
    610                 615                 620
Ser Trp Val Gly Phe Ser Val Lys Met Ala His Arg Ile Thr Ala Gly
625                 630                 635                 640
Ser Asp Ile Leu Leu Met Pro Ser Arg Phe Glu Pro Cys Gly Leu Asn
            645                 650                 655
Gln Leu Tyr Ala Met Ser Tyr Gly Thr Val Pro Val Val His Gly Val
            660                 665                 670
Gly Gly Leu Arg Asp Thr Val Gln Pro Phe Asn Pro Phe Asp Glu Ser
        675                 680                 685
Gly Val Gly Trp Thr Phe Asp Arg Ala Glu Ala Asn Lys Leu Met Ala
        690                 695                 700
Ala Leu Trp Asn Cys Leu Leu Thr Tyr Lys Asp Tyr Lys Lys Ser Trp
705                 710                 715                 720
Glu Gly Ile Gln Glu Arg Gly Met Ser Gln Asp Leu Ser Trp Asp Asn
                725                 730                 735
Ala Ala Gln Gln Tyr Glu Glu Val Leu Val Ala Lys Tyr Gln Trp
            740                 745                 750

<210> SEQ ID NO 29
<211> LENGTH: 637
<212> TYPE: PRT
<213> ORGANISM: Oryza sativa

<400> SEQUENCE: 29

Val Val Cys Ser Ala Ser Ala Ala Gly Gly Glu Asp Gly Val Ala Lys
1               5                   10                  15
Ala Lys Ala Lys Ser Ala Gly Ser Ser Lys Ala Val Ala Met Gln Gly
            20                  25                  30
Ser Thr Ala Lys Ala Asp His Val Glu Asp Ser Val Ser Ser Pro Lys
        35                  40                  45
```

```
Ser Val Lys Pro Ala Val Ala Lys Gln Asn Gly Glu Val Val Ser Arg
 50                  55                  60
Ala Thr Lys Ser Asp Ala Pro Val Pro Lys Pro Lys Val Asp Pro Ser
 65                  70                  75                  80
Val Pro Ala Ser Lys Ala Glu Ala Asp Gly Asn Ala Gln Ala Val Glu
                 85                  90                  95
Ser Lys Ala Ala Leu Asp Lys Lys Glu Asp Val Gly Val Ala Glu Pro
                100                 105                 110
Leu Glu Ala Lys Ala Asp Ala Gly Gly Asp Ala Gly Ala Val Ser Ser
                115                 120                 125
Ala Asp Asp Ser Glu Asn Lys Glu Ser Gly Pro Leu Ala Gly Pro Asn
130                 135                 140
Val Met Asn Val Ile Val Val Ala Ser Glu Cys Ser Pro Phe Cys Lys
145                 150                 155                 160
Thr Gly Gly Leu Gly Asp Val Val Gly Ala Leu Pro Lys Ala Leu Ala
                165                 170                 175
Arg Arg Gly His Arg Val Met Val Val Ile Pro Arg Tyr Gly Glu Tyr
                180                 185                 190
Ala Glu Ala Lys Asp Leu Gly Val Arg Lys Arg Tyr Arg Val Ala Gly
                195                 200                 205
Gln Asp Ser Glu Val Ser Tyr Phe His Ala Phe Ile Asp Gly Val Asp
210                 215                 220
Phe Val Phe Leu Glu Ala Pro Pro Phe Arg His Arg His Asn Asp Ile
225                 230                 235                 240
Tyr Gly Gly Glu Arg Phe Asp Val Leu Lys Arg Met Ile Leu Phe Cys
                245                 250                 255
Lys Ala Ala Val Glu Val Pro Trp Phe Ala Pro Cys Gly Gly Ser Ile
                260                 265                 270
Tyr Gly Asp Gly Asn Leu Val Phe Ile Ala Asn Asp Trp His Thr Ala
                275                 280                 285
Leu Leu Pro Val Tyr Leu Lys Ala Tyr Tyr Arg Asp Asn Gly Leu Met
                290                 295                 300
Gln Tyr Thr Arg Ser Val Leu Val Ile His Asn Ile Ala His Gln Gly
305                 310                 315                 320
Arg Gly Pro Val Asp Asp Phe Ala Thr Met Asp Leu Pro Glu His Tyr
                325                 330                 335
Ile Asp His Phe Arg Leu Tyr Asp Pro Val Gly Gly Glu His Ser Asn
                340                 345                 350
Val Phe Ala Ala Gly Leu Lys Met Ala Asp Arg Ala Val Thr Val Ser
                355                 360                 365
His Gly Tyr Leu Trp Glu Ile Lys Thr Met Asp Gly Gly Trp Gly Leu
                370                 375                 380
His Glu Ile Ile Asn His Asn Asp Trp Lys Leu Gln Gly Ile Val Asn
385                 390                 395                 400
Gly Ile Asp Met Ala Glu Trp Asn Pro Glu Val Asp Glu His Leu Gln
                405                 410                 415
Ser Asp Gly Tyr Ala Asn Tyr Thr Phe Glu Thr Leu Asp Thr Gly Lys
                420                 425                 430
Lys Gln Cys Lys Glu Ala Leu Gln Arg Gln Leu Gly Leu Gln Val Arg
                435                 440                 445
Asp Asp Val Pro Leu Ile Gly Phe Ile Gly Arg Leu Asp His Gln Lys
                450                 455                 460
Gly Val Asp Ile Ile Gly Asp Ala Met Pro Trp Ile Ala Gly Gln Asp
```

```
              465                 470                 475                 480
        Val Gln Val Val Met Leu Gly Thr Gly Arg Pro Asp Leu Glu Glu Met
                        485                 490                 495

Leu Arg Arg Phe Glu Ser Glu His Asn Asp Lys Val Arg Gly Trp Val
                    500                 505                 510

Gly Phe Ser Val Gln Leu Ala His Arg Ile Thr Ala Gly Ala Asp Val
                    515                 520                 525

Leu Leu Met Pro Ser Arg Phe Glu Pro Cys Gly Leu Asn Gln Leu Tyr
                530                 535                 540

Ala Met Ala Tyr Gly Thr Val Pro Val His Ala Val Gly Gly Leu
        545                 550                 555                 560

Arg Asp Thr Val Ala Pro Phe Asp Pro Phe Ala Asp Thr Gly Leu Gly
                        565                 570                 575

Trp Thr Phe Asp Arg Ala Glu Ala Asn Arg Met Ile Asp Ala Leu Gly
                        580                 585                 590

His Cys Leu Asn Thr Tyr Arg Asn Tyr Lys Glu Ser Trp Arg Gly Leu
                    595                 600                 605

Gln Ala Arg Gly Met Ala Gln Asp Leu Ser Trp Asp His Ala Ala Glu
                610                 615                 620

Leu Tyr Glu Asp Val Leu Val Lys Ala Lys Tyr Gln Trp
        625                 630                 635

<210> SEQ ID NO 30
<211> LENGTH: 694
<212> TYPE: PRT
<213> ORGANISM: Oryza sativa

<400> SEQUENCE: 30

Met Ser Gly Ala Ile Ala Ser Ser Pro Ala Ala Thr Leu Phe Leu Ala
         1               5                   10                  15

Gly Ser Ser Ser Ser Pro Arg Arg Arg Ser Arg Val Ser Gly
                    20                  25                  30

Val Trp Trp His Leu Tyr Gly Gly Thr Gly Leu Arg Leu His Trp Glu
                    35                  40                  45

Arg Arg Gly Leu Val Arg Asp Gly Ala Val Val Cys Ser Ala Ser Ala
        50                  55                  60

Ala Gly Gly Glu Asp Gly Val Ala Lys Ala Lys Thr Lys Ser Ala Gly
        65                  70                  75                  80

Ser Ser Lys Ala Val Ala Val Gln Gly Ser Thr Ala Lys Ala Asp His
                        85                  90                  95

Val Glu Asp Ser Val Ser Ser Pro Lys Tyr Val Lys Pro Ala Val Ala
                    100                 105                 110

Lys Gln Asn Gly Glu Val Val Ser Arg Ala Thr Lys Ser Asp Ala Pro
                    115                 120                 125

Val Ser Lys Pro Lys Val Asp Pro Ser Val Pro Ala Ser Lys Ala Glu
                130                 135                 140

Ala Asp Gly Asn Ala Gln Ala Val Glu Ser Lys Ala Leu Asp Lys
        145                 150                 155                 160

Lys Glu Asp Val Gly Val Ala Glu Pro Leu Glu Ala Lys Ala Asp Ala
                        165                 170                 175

Gly Gly Asp Ala Gly Ala Val Ser Ser Ala Asp Ser Glu Asn Lys
                    180                 185                 190

Glu Ser Gly Pro Leu Ala Gly Pro Asn Val Met Asn Val Ile Val Val
                    195                 200                 205
```

```
Ala Ser Glu Cys Ser Pro Phe Cys Lys Thr Gly Gly Leu Gly Asp Val
    210                 215                 220
Val Gly Ala Leu Pro Lys Ala Leu Ala Arg Arg Gly His Arg Val Met
225                 230                 235                 240
Val Val Ile Pro Arg Tyr Gly Glu Tyr Ala Glu Ala Lys Asp Leu Gly
                245                 250                 255
Val Arg Lys Arg Tyr Arg Val Ala Gly Gln Asp Ser Glu Val Ser Tyr
            260                 265                 270
Phe His Ala Phe Ile Asp Gly Val Asp Phe Val Phe Leu Glu Ala Pro
        275                 280                 285
Pro Phe Arg His Arg His Asn Asp Ile Tyr Gly Gly Glu Arg Phe Asp
    290                 295                 300
Val Leu Lys Arg Met Ile Leu Phe Cys Lys Ala Ala Val Glu Val Pro
305                 310                 315                 320
Trp Phe Ala Pro Cys Gly Gly Ser Ile Tyr Gly Asp Gly Asn Leu Val
                325                 330                 335
Phe Ile Ala Asn Asp Trp His Thr Ala Leu Leu Pro Val Cys Leu Lys
            340                 345                 350
Ala Tyr Tyr Arg Asp Asn Gly Leu Met Gln Tyr Thr Arg Ser Val Leu
        355                 360                 365
Val Ile His Asn Ile Ala His Gln Gly Arg Gly Pro Val Asp Asp Phe
    370                 375                 380
Ala Thr Met Asp Leu Pro Glu His Tyr Ile Asp His Phe Arg Leu Tyr
385                 390                 395                 400
Asp Pro Val Gly Gly Glu His Ser Asn Val Phe Ala Ala Gly Leu Lys
                405                 410                 415
Met Ala Asp Arg Ala Val Thr Val Ser His Gly Tyr Leu Trp Glu Ile
            420                 425                 430
Lys Thr Met Asp Gly Gly Trp Gly Leu His Glu Ile Ile Asn His Asn
        435                 440                 445
Asp Trp Lys Leu Gln Gly Ile Val Asn Gly Ile Asp Met Ala Glu Trp
    450                 455                 460
Asn Pro Glu Val Asp Glu His Leu Gln Ser Asp Gly Tyr Ala Asn Tyr
465                 470                 475                 480
Thr Phe Glu Thr Leu Asp Thr Gly Lys Lys Gln Cys Lys Glu Ala Leu
                485                 490                 495
Gln Arg Gln Leu Gly Leu Gln Val Arg Asp Asp Val Pro Leu Ile Gly
            500                 505                 510
Phe Ile Gly Arg Leu Asp His Gln Lys Gly Val Asp Ile Ile Gly Asp
        515                 520                 525
Ala Met Pro Trp Ile Ala Gly Gln Asp Val Gln Val Val Met Leu Gly
    530                 535                 540
Thr Gly Arg Pro Asp Leu Glu Glu Met Leu Arg Arg Phe Glu Ser Glu
545                 550                 555                 560
His Asn Asp Lys Val Arg Gly Trp Val Gly Phe Ser Val Gln Leu Ala
                565                 570                 575
His Arg Ile Thr Ala Gly Ala Asp Val Leu Leu Met Pro Ser Arg Phe
            580                 585                 590
Glu Pro Cys Gly Leu Asn Gln Leu Tyr Ala Met Ala Tyr Ser Thr Val
        595                 600                 605
Pro Val Val His Ala Val Gly Gly Leu Arg Asp Thr Val Ala Pro Phe
    610                 615                 620
Asp Pro Phe Ala Asp Thr Gly Leu Gly Trp Thr Phe Asp Arg Ala Glu
```

```
                        625                 630                 635                 640
Ala Asn Arg Met Ile Asp Ala Leu Gly His Cys Leu Asn Thr Tyr Arg
                    645                 650                 655
Asn Tyr Lys Glu Ser Trp Arg Gly Leu Gln Ala Arg Gly Met Ala Gln
                660                 665                 670
Asp Leu Ser Trp Asp His Ala Ala Glu Leu Tyr Glu Asp Val Leu Val
            675                 680                 685
Lys Ala Lys Tyr Gln Trp
        690

<210> SEQ ID NO 31
<211> LENGTH: 749
<212> TYPE: PRT
<213> ORGANISM: Oryza sativa

<400> SEQUENCE: 31

Met Ala Ala Ala Val Ser Ser Leu Leu Ala Pro Ser Gly Ser Cys
 1               5                  10                  15
Tyr Ser Pro Gly Cys His Ser Cys Trp Gly Pro Gly Pro Gly Gly Gly
                20                  25                  30
Arg Arg Leu Pro Ser Pro Arg Arg Pro Ile Thr Ala Ala Ala Arg
            35                  40                  45
Pro Thr Trp Ala Val Pro Arg Arg Ser Arg Leu Glu Trp Gly Arg Val
    50                  55                  60
Glu Ala Gln Asn Ser Gly Ala Arg Thr Ser Cys Arg Ala Ala Leu Gln
65                  70                  75                  80
Trp Leu Ser Ser Thr Ala Arg Ser His Val Asn Val Gly Tyr Gly Ser
                85                  90                  95
Pro Leu Val Phe Pro Gly Leu Thr Lys Pro Gly Ser Ser Arg Cys Leu
            100                 105                 110
Cys Val Val Gly Met Val Gly Asn Ala Gly Asn Gln Val Gly Asp Asp
        115                 120                 125
Ser Asp Asp Gly Ile Lys Val Thr Asn Glu Lys Leu Arg Ala Val Ile
    130                 135                 140
Arg Lys Ser Lys Glu Val Leu Glu Ile His Arg Asn Leu Leu Glu Lys
145                 150                 155                 160
Ile Ser Ala Ser Glu Arg Lys Lys Ile Thr Ser Ile Glu Asp Ser
                165                 170                 175
Ser Ile Tyr Asn Glu Gln Asp Pro Phe Gly Gln Arg Asp Ser Ser Phe
            180                 185                 190
Tyr His Leu Asp Glu Val Pro Asp Asp Glu Phe Ser Tyr Asp Leu
        195                 200                 205
Gln Met Tyr Leu Asp Arg His Pro Asp Gln Ser Glu Val Val Ala Thr
    210                 215                 220
Gln Asp Tyr Glu Ala Gln Leu Ser Gln Ile Ser Glu Met Gly Gln Ser
225                 230                 235                 240
Val Ala Glu Gly Thr Ser Asp Asp Pro Ser Ala Ser Ala Ser Val Asp
                245                 250                 255
Leu Ile Asn Ile Ile Leu Val Ala Ala Glu Cys Ala Pro Trp Ser Lys
            260                 265                 270
Thr Gly Gly Leu Gly Asp Val Ala Gly Ala Leu Pro Lys Ala Leu Ala
        275                 280                 285
Arg Arg Gly His Arg Val Met Val Val Pro Met Tyr Lys Asn Tyr
    290                 295                 300
```

-continued

```
Ala Glu Pro Gln Gln Leu Gly Glu Pro Arg Arg Tyr Gln Val Ala Gly
305                 310                 315                 320

Gln Asp Met Glu Val Ile Tyr Tyr His Ala Tyr Ile Asp Gly Val Asp
                325                 330                 335

Phe Val Phe Ile Asp Asn Pro Ile Phe His His Val Glu Asn Asp Ile
            340                 345                 350

Tyr Gly Gly Asp Arg Thr Asp Ile Leu Lys Arg Met Val Leu Leu Cys
        355                 360                 365

Lys Ala Ala Ile Glu Val Pro Trp Tyr Val Pro Cys Gly Gly Tyr Cys
370                 375                 380

Tyr Gly Asp Gly Asn Leu Val Phe Leu Ala Asn Asp Trp His Thr Ala
385                 390                 395                 400

Leu Leu Pro Val Tyr Leu Lys Ala Tyr Tyr His Asp Asn Gly Phe Met
                405                 410                 415

Ile Tyr Ala Arg Ser Val Leu Val Ile His Asn Ile Ala His Gln Gly
            420                 425                 430

Arg Gly Pro Leu Asp Asp Phe Ser Tyr Leu Asp Leu Pro Val Asp Tyr
        435                 440                 445

Met Asp Leu Phe Lys Leu Tyr Asp Pro Phe Gly Gly Asp His Leu Asn
    450                 455                 460

Ile Phe Ala Ala Gly Ile Lys Ala Ala Asp Arg Leu Leu Thr Val Ser
465                 470                 475                 480

His Gly Tyr Ala Trp Glu Leu Lys Thr Ala Glu Gly Gly Trp Gly Leu
                485                 490                 495

His Gly Ile Ile Asn Glu Ser Asp Trp Lys Phe Gln Gly Ile Val Asn
            500                 505                 510

Gly Ile Asp Thr Thr Asp Trp Asn Pro Arg Cys Asp Ile His Leu Lys
        515                 520                 525

Ser Asp Gly Tyr Thr Asn Tyr Ser Leu Glu Thr Val Gln Ala Gly Lys
    530                 535                 540

Gln Gln Cys Lys Ala Ala Leu Gln Lys Glu Leu Gly Leu Pro Val Arg
545                 550                 555                 560

Gly Asp Val Pro Val Ile Ala Phe Ile Gly Arg Leu Asp His Gln Lys
                565                 570                 575

Gly Val Asp Leu Ile Ala Glu Ala Met Pro Trp Ile Ala Gly Gln Asp
            580                 585                 590

Val Gln Leu Ile Met Leu Gly Thr Gly Arg Gln Asp Leu Glu Asp Thr
        595                 600                 605

Leu Arg Arg Leu Glu Ser Gln His Tyr Asp Arg Val Arg Gly Trp Val
    610                 615                 620

Gly Phe Ser Ile Arg Leu Ala His Arg Met Thr Ala Gly Ala Asp Ile
625                 630                 635                 640

Leu Leu Met Pro Ser Arg Phe Glu Pro Cys Gly Leu Asn Gln Leu Tyr
                645                 650                 655

Ala Met Met Tyr Gly Thr Val Pro Val Val His Ala Val Gly Gly Leu
            660                 665                 670

Arg Asp Thr Val Glu His Tyr Asn Pro Tyr Glu Glu Ser Gly Leu Gly
        675                 680                 685

Trp Thr Phe Glu Lys Ala Glu Ala Asn Arg Leu Ile Asp Ala Leu Gly
    690                 695                 700

His Cys Leu Asn Thr Tyr Arg Asn Tyr Arg Thr Ser Trp Glu Gly Leu
705                 710                 715                 720

Gln Lys Arg Gly Met Met Gln Asp Leu Ser Trp Asp Asn Ala Ala Lys
```

-continued

```
                725                 730                 735
Leu Tyr Glu Glu Val Leu Leu Ala Ala Lys Tyr Gln Trp
            740                 745

<210> SEQ ID NO 32
<211> LENGTH: 530
<212> TYPE: PRT
<213> ORGANISM: Marchantia polymorpha

<400> SEQUENCE: 32

Met Val Leu Cys Ala Met Glu Ala Val Gly Ala Leu Thr Gly Gly Ile
 1               5                  10                  15

Cys Ala Ser Ala Ala Ser Ser Ser Ser Ser His Val Gly Leu
                20                  25                  30

Arg Arg Val Asn Ser Thr Ser Ala Ser Val Ala Asp Cys
            35                  40                  45

Gly Arg Arg Asp Leu Asp Gln Glu Lys Leu Lys Gly Val Ala Glu
50                  55                  60

Glu Leu Gly Cys His Arg Ser Ser Leu Trp Ala Ala Ala Ala Gly
65                  70                  75                  80

Glu Thr Ser Val Arg Gly Ile Arg Lys Ser Arg Ala Val Arg Ala Val
                85                  90                  95

Ser Arg Ser Asn Trp Glu Ser Leu Arg Lys Val Ser Ala Leu Ala Ser
                100                 105                 110

Gln Trp Gly Ser Glu Ser Ser Val Glu Trp Gln Glu Asp Glu Tyr Gln
            115                 120                 125

Tyr Thr Arg Pro Gly Asn Gly Ser Leu Thr Ala Ser Lys Ala Gly Gly
130                 135                 140

Gly Gly Ser Pro Leu Pro Ser Ala Ser Ser Trp Gln Gly Ala Pro Pro
145                 150                 155                 160

Ile Gln Ser Phe Asn Glu Ala Lys Ile Lys Val Ile Gly Val Gly Gly
                165                 170                 175

Gly Gly Ser Asn Ala Val Asn Arg Met Leu Gln Ser Glu Met Lys Gly
            180                 185                 190

Val Glu Phe Trp Ile Val Asn Thr Asp Ser Gln Ala Met Ala Met Ser
        195                 200                 205

Pro Val Gln Glu Glu Asn Arg Leu Gln Ile Gly Gln Lys Leu Thr Arg
    210                 215                 220

Gly Leu Gly Ala Gly Gly Asn Pro Glu Ile Gly Met Ser Ala Ala Glu
225                 230                 235                 240

Glu Ser Lys Ala Leu Val Glu Glu Ala Leu Arg Gly Ala Asp Met Val
                245                 250                 255

Phe Val Thr Ala Gly Met Gly Gly Gly Thr Gly Ser Gly Ala Ala Pro
            260                 265                 270

Val Ile Ala Gly Val Ala Lys Ala Leu Gly Ile Leu Thr Val Gly Ile
        275                 280                 285

Val Thr Thr Pro Phe Ser Phe Glu Gly Arg Arg Arg Ser Val Gln Ala
    290                 295                 300

Gln Glu Gly Ile Ala Ala Leu Arg Asn Asn Val Asp Thr Leu Ile Ile
305                 310                 315                 320

Ile Pro Asn Asp Lys Leu Leu Thr Ala Val Ser Gln Ser Thr Pro Val
                325                 330                 335

Thr Glu Ala Phe Asn Leu Ala Asp Asp Ile Leu Arg Gln Gly Val Arg
            340                 345                 350
```

-continued

```
Gly Ile Ser Asp Ile Ile Thr Val Pro Gly Leu Val Asn Val Asp Phe
        355                 360                 365

Ala Asp Val Arg Ala Ile Met Ala Asp Ala Gly Ser Ser Leu Met Gly
    370                 375                 380

Ile Gly Thr Ala Thr Gly Lys Ser Arg Ala Arg Asp Ala Ala Leu Ser
385                 390                 395                 400

Ala Ile Gln Ser Pro Leu Leu Asp Val Gly Ile Glu Arg Ala Thr Gly
                405                 410                 415

Ile Val Trp Asn Ile Thr Gly Gly Ser Asp Met Thr Leu Phe Glu Val
            420                 425                 430

Asn Ala Ala Glu Val Ile Tyr Asp Leu Val Asp Pro Asn Ala Asn
            435                 440                 445

Leu Ile Phe Gly Ala Val Val Asp Glu Ser Tyr Thr Gly Glu Val Ser
    450                 455                 460

Ile Thr Leu Ile Ala Thr Gly Phe Arg Gly Gln Asp Asp Ser Glu Leu
465                 470                 475                 480

Arg Ser Val Gln Gln Thr Gly Arg Ser Met Asp Gly Asp His Gly Arg
                485                 490                 495

Arg Pro Ser Gly Val Pro Pro Leu Ser Gly Ser Asn Gly Ser Thr Val
            500                 505                 510

Asp Ile Pro Ser Phe Leu Lys Arg Arg Gly Arg Ser Arg Tyr Pro Arg
            515                 520                 525

Val Gly
    530

<210> SEQ ID NO 33
<211> LENGTH: 464
<212> TYPE: PRT
<213> ORGANISM: Physcomitrella patens

<400> SEQUENCE: 33

Met Ala Leu Leu Gly Ser Arg Ser Gly Leu Val Gly Leu Arg Val Ser
1               5                   10                  15

Ser Arg Val Gly Gly Glu Ser Ser Arg Ile Val Pro Ala Thr Arg Asp
            20                  25                  30

Arg Phe Cys Val His Leu Arg Pro Ser Thr Arg Ala His Arg Arg Leu
        35                  40                  45

Asp Arg Thr Val Gly Asn Glu Ser Leu Cys Thr Pro Arg Glu Arg Asp
    50                  55                  60

Leu Ala Ala Glu Pro Lys Phe Leu His Thr Gly Trp Glu Ser Ser
65                  70                  75                  80

Ser Ser Ser Ser Ser Cys Glu Thr Gly Ile Pro Val Thr Ala Phe
                85                  90                  95

Gly Gly Asn Gly Asp Glu Tyr Glu Ser Ser Asn Glu Ala Lys Ile Lys
            100                 105                 110

Val Ile Gly Val Gly Gly Gly Ser Asn Ala Val Asn Arg Met Leu
        115                 120                 125

Glu Ser Glu Met Gln Gly Val Glu Phe Trp Ile Val Asn Thr Asp Ala
    130                 135                 140

Gln Ala Met Ala Leu Ser Pro Val Pro Ala Gln Asn Arg Leu Gln Ile
145                 150                 155                 160

Gly Gln Lys Leu Thr Arg Gly Leu Gly Ala Gly Asn Pro Glu Ile
                165                 170                 175

Gly Cys Ser Ala Ala Glu Glu Ser Lys Ala Met Val Glu Glu Ala Leu
            180                 185                 190
```

-continued

Arg Gly Ala Asp Met Val Phe Val Thr Ala Gly Met Gly Gly Thr
            195                 200                 205

Gly Ser Gly Ala Ala Pro Ile Ile Ala Gly Val Ala Lys Gln Leu Gly
    210                 215                 220

Ile Leu Thr Val Gly Ile Val Thr Thr Pro Phe Ala Phe Glu Gly Arg
225                 230                 235                 240

Arg Arg Ser Val Gln Ala His Glu Gly Ile Ala Ala Leu Lys Asn Asn
                245                 250                 255

Val Asp Thr Leu Ile Thr Ile Pro Asn Asn Lys Leu Leu Thr Ala Val
            260                 265                 270

Ala Gln Ser Thr Pro Val Thr Glu Ala Phe Asn Leu Ala Asp Asp Ile
        275                 280                 285

Leu Arg Gln Gly Val Arg Gly Ile Ser Asp Ile Ile Thr Val Pro Gly
    290                 295                 300

Leu Val Asn Val Asp Phe Ala Asp Val Arg Ala Ile Met Ala Asn Ala
305                 310                 315                 320

Gly Ser Ser Leu Met Gly Ile Gly Thr Ala Thr Gly Lys Ser Lys Ala
                325                 330                 335

Arg Glu Ala Ala Leu Ser Ala Ile Gln Ser Pro Leu Leu Asp Val Gly
            340                 345                 350

Ile Glu Arg Ala Thr Gly Ile Val Trp Asn Ile Thr Gly Gly Ser Asp
        355                 360                 365

Met Thr Leu Phe Glu Val Asn Ala Ala Ala Glu Val Ile Tyr Asp Leu
    370                 375                 380

Val Asp Pro Asn Ala Asn Leu Ile Phe Gly Ala Val Val Asp Glu Ala
385                 390                 395                 400

Leu His Asp Gln Ile Ser Ile Thr Leu Ile Ala Thr Gly Phe Ser Ser
                405                 410                 415

Gln Asp Asp Pro Asp Ala Arg Ser Met Gln Tyr Ala Ser Arg Val Leu
            420                 425                 430

Glu Gly Gln Ala Gly Arg Ser Ser Met Ala Ser Ser Arg Gly Gly Asn
        435                 440                 445

Ser Ser Thr Ile Asn Ile Pro Asn Phe Leu Arg Lys Arg Gly Gln Arg
    450                 455                 460

<210> SEQ ID NO 34
<211> LENGTH: 257
<212> TYPE: PRT
<213> ORGANISM: Triticum aestivum
<220> FEATURE:
<221> NAME/KEY: VARIANT
<222> LOCATION: 94
<223> OTHER INFORMATION: Xaa = any amino acid

<400> SEQUENCE: 34

Ala Gly Ser Gly Val Glu Phe Trp Ile Val Asn Thr Asp Val Gln Ala
1               5                   10                  15

Ile Arg Met Ser Pro Val His Ser Gln Asn Arg Leu Gln Ile Gly Gln
            20                  25                  30

Glu Leu Thr Arg Gly Leu Gly Ala Gly Gly Asn Pro Asp Ile Gly Met
        35                  40                  45

Asn Ala Ala Lys Glu Ser Cys Glu Ser Ile Glu Glu Ala Leu His Gly
    50                  55                  60

Ala Asp Met Val Phe Val Thr Ala Gly Met Gly Gly Thr Gly Thr
65                  70                  75                  80

-continued

```
Gly Gly Ala Pro Val Ile Ala Gly Ile Ala Lys Ser Met Xaa Ile Leu
                85                  90                  95
Thr Val Gly Ile Val Thr Thr Pro Phe Ser Phe Glu Gly Arg Arg Arg
            100                 105                 110
Ala Val Gln Ala Gln Glu Gly Thr Ser Ala Leu Arg Asn Ser Val Asp
        115                 120                 125
Thr Leu Ile Val Ile Pro Asn Asp Lys Leu Leu Ser Ala Val Ser Pro
130                 135                 140
Asn Thr Pro Val Thr Glu Ala Phe Asn Leu Ala Asp Ile Leu Trp
145                 150                 155                 160
Gln Gly Ile Arg Gly Ile Ser Asp Ile Ile Thr Val Pro Gly Leu Val
                165                 170                 175
Asn Val Asp Phe Ala Asp Val Xaa Ala Ile Met Gln Asn Ala Gly Ser
            180                 185                 190
Ser Xaa Met Gly Ile Gly Thr Ala Thr Gly Lys Ser Arg Ala Arg Asp
        195                 200                 205
Ala Ala Leu Asn Ala Ile Gln Ser Pro Leu Leu Asp Ile Gly Ile Glu
        210                 215                 220
Arg Ala Thr Gly Ile Val Trp Asn Ile Thr Gly Gly Asn Asp Leu Thr
225                 230                 235                 240
Leu Phe Glu Val Asn Ala Ala Ala Glu Val Ile Tyr Asp Pro Arg
                245                 250                 255
Ala
```

<210> SEQ ID NO 35
<211> LENGTH: 277
<212> TYPE: PRT
<213> ORGANISM: Solanum tuberosum
<220> FEATURE:
<221> NAME/KEY: VARIANT
<222> LOCATION: 74
<223> OTHER INFORMATION: Xaa = any amino acid

<400> SEQUENCE: 35

```
Gly Ser Asn Ala Val Asn Xaa Met Ile Glu Ser Ser Met Asn Gly Val
  1               5                  10                  15
Glu Phe Trp Ile Val Asn Thr Asp Ile Gln Ala Ile Arg Met Ser Pro
                20                  25                  30
Val Phe Pro Glu Asn Arg Leu Pro Ile Gly Gln Glu Leu Thr Arg Gly
            35                  40                  45
Leu Gly Ala Gly Gly Asn Pro Asp Ile Gly Met Asn Ala Ala Lys Glu
        50                  55                  60
Ser Lys Glu Ala Ile Glu Ala Val Xaa Gly Ala Asp Met Val Phe
65                  70                  75                  80
Val Thr Ala Gly Met Gly Gly Thr Gly Thr Gly Ala Pro Ile
                85                  90                  95
Ile Ala Gly Ile Ala Lys Ser Met Gly Ile Leu Thr Val Gly Ile Val
                100                 105                 110
Thr Thr Pro Phe Ser Phe Glu Gly Arg Arg Arg Ala Val Gln Ala Gln
            115                 120                 125
Glu Gly Ile Ala Ala Leu Arg Glu Asn Val Asp Thr Leu Ile Val Ile
        130                 135                 140
Pro Asn Asp Lys Leu Leu Thr Xaa Val Ser Leu Ser Thr Pro Val Thr
145                 150                 155                 160
Glu Ala Phe Asn Leu Ala Asp Asp Ile Leu Arg Gln Gly Val Arg Gly
                165                 170                 175
```

-continued

```
Ile Ser Asp Ile Ile Thr Ile Pro Gly Leu Val Asn Val Asp Phe Ala
            180                 185                 190

Asp Val Arg Ala Ile Met Ala Asn Ala Gly Ser Ser Leu Met Gly Ile
        195                 200                 205

Gly Thr Ala Thr Gly Lys Thr Arg Ala Arg Asp Ala Ala Leu Asn Ala
    210                 215                 220

Val Gln Ser Pro Leu Leu Asp Ile Gly Ile Glu Arg Ala Thr Gly Ile
225                 230                 235                 240

Val Trp Asn Ile Thr Gly Gly Asn Xaa Leu Thr Leu Phe Glu Val Asn
                245                 250                 255

Ala Ala Ala Glu Val Ile Tyr Asp Leu Val Asp Pro Ser Ala Asn Leu
            260                 265                 270

Ile Phe Gly Ala Asp
            275
```

<210> SEQ ID NO 36
<211> LENGTH: 468
<212> TYPE: PRT
<213> ORGANISM: Nicotiana tabacum

<400> SEQUENCE: 36

```
Met Ala Thr Cys Thr Ser Ala Val Phe Met Pro Pro Asp Thr Arg Arg
1               5                   10                  15

Ser Arg Gly Val Leu Thr Leu Leu Gly Gly Arg Leu Cys Ala Leu Lys
            20                  25                  30

Met Gln Asp Glu Lys Ile Gly Phe Leu Gly Val Asn Gln Lys Gly Ser
        35                  40                  45

Ser Ser Leu Pro Gln Phe Lys Cys Ser Ser Asn Ser His Ser Val Asn
    50                  55                  60

Gln Tyr Gln Asn Lys Asp Ser Phe Leu Asn Leu His Pro Glu Ile Ser
65                  70                  75                  80

Leu Leu Arg Gly Glu Glu Ser Ser Ser Gly Asn Val Thr Glu Ser Leu
                85                  90                  95

Met Asp Ser Ser Arg Ser Asn Asn Phe Asn Glu Ala Lys Ile Lys Val
            100                 105                 110

Val Gly Val Gly Gly Gly Gly Ser Asn Ala Val Asn Arg Met Ile Glu
        115                 120                 125

Ser Ser Met Lys Gly Val Glu Phe Trp Ile Val Asn Thr Asp Ile Gln
    130                 135                 140

Ala Met Arg Met Ser Pro Val Ala Ala Glu Gln Arg Leu Pro Ile Gly
145                 150                 155                 160

Gln Glu Leu Thr Arg Gly Leu Gly Ala Gly Asn Pro Asp Ile Gly
                165                 170                 175

Met Asn Ala Ala Asn Glu Ser Lys Gln Ala Ile Glu Glu Ala Val Tyr
            180                 185                 190

Gly Ala Asp Met Val Phe Val Thr Ala Gly Met Gly Gly Gly Thr Gly
        195                 200                 205

Thr Gly Ala Ala Pro Ile Ile Ala Gly Thr Ala Lys Ser Met Gly Ile
    210                 215                 220

Leu Thr Val Gly Ile Val Thr Thr Pro Phe Ser Phe Glu Gly Arg Arg
225                 230                 235                 240

Arg Ala Val Gln Ala Gln Glu Gly Ile Ala Ala Leu Arg Glu Asn Val
                245                 250                 255

Asp Thr Leu Ile Val Ile Pro Asn Asp Lys Leu Leu Thr Ala Val Ser
```

```
                      260                 265                 270
Pro Ser Thr Pro Val Thr Glu Ala Phe Asn Leu Ala Asp Asp Ile Leu
        275                 280                 285

Arg Gln Gly Val Arg Gly Ile Ser Asp Ile Ile Thr Ile Pro Gly Leu
        290                 295                 300

Val Asn Val Asp Phe Ala Asp Val Arg Ala Ile Met Ala Asn Ala Gly
305                 310                 315                 320

Ser Ser Leu Met Gly Ile Gly Thr Ala Thr Gly Lys Thr Arg Ala Arg
                325                 330                 335

Asp Ala Ala Leu Asn Ala Ile Gln Ser Pro Leu Leu Asp Ile Gly Ile
                340                 345                 350

Glu Arg Ala Thr Gly Ile Val Trp Asn Ile Thr Gly Gly Ser Asp Leu
                355                 360                 365

Thr Leu Phe Glu Val Asn Ala Ala Glu Val Ile Tyr Asp Leu Val
            370                 375                 380

Asp Pro Ser Ala Asn Leu Ile Phe Gly Ala Val Ile Asp Pro Ser Ile
385                 390                 395                 400

Ser Gly Gln Val Ser Ile Thr Leu Ile Ala Thr Gly Phe Lys Arg Gln
                405                 410                 415

Glu Glu Ser Asp Gly Arg Pro Leu Gln Gly Asn Gln Leu Thr Gln Gly
                420                 425                 430

Asp Val Ser Leu Gly Asn Asn Arg Arg Pro Ala Ser Phe Leu Glu Gly
                435                 440                 445

Gly Ser Val Glu Ile Pro Glu Phe Leu Arg Lys Lys Gly Arg Ser Arg
                450                 455                 460

Tyr Pro Arg Ala
465

<210> SEQ ID NO 37
<211> LENGTH: 478
<212> TYPE: PRT
<213> ORGANISM: Arabidopsis thaliana

<400> SEQUENCE: 37

Met Ala Thr Tyr Val Ser Pro Cys Phe Thr Pro Ser Asp Ser Arg Leu
1               5                   10                  15

Leu Thr Val Leu Arg Lys Asn Val Leu Pro Glu Asn His Leu Gly Arg
                20                  25                  30

Leu Asn Ser Ile Arg Thr Ile Asp Ser Lys Lys Asn Arg Val Val Val
            35                  40                  45

Ala Ala Gln Lys Ser Glu Ser Ser Pro Ile Arg Asn Ser Pro Arg His
        50                  55                  60

Tyr Gln Ser Gln Ala Gln Asp Pro Phe Leu Asn Leu His Pro Glu Ile
65                  70                  75                  80

Ser Met Leu Arg Gly Glu Gly Thr Ser Thr Ile Val Asn Pro Arg Lys
                85                  90                  95

Glu Thr Ser Ser Gly Pro Val Val Glu Asp Phe Glu Glu Pro Ser Ala
                100                 105                 110

Pro Ser Asn Tyr Asn Glu Ala Arg Ile Lys Val Ile Gly Val Gly Gly
            115                 120                 125

Gly Gly Ser Asn Ala Val Asn Arg Met Ile Glu Ser Glu Met Ser Gly
        130                 135                 140

Val Glu Phe Trp Ile Val Asn Thr Asp Ile Gln Ala Met Arg Met Ser
145                 150                 155                 160
```

```
Pro Val Leu Pro Asp Asn Arg Leu Gln Ile Gly Lys Glu Leu Thr Arg
            165                 170                 175

Gly Leu Gly Ala Gly Gly Asn Pro Glu Ile Gly Met Asn Ala Ala Arg
            180                 185                 190

Glu Ser Lys Glu Val Ile Glu Glu Ala Leu Tyr Gly Ser Asp Met Val
            195                 200                 205

Phe Val Thr Ala Gly Met Gly Gly Thr Gly Thr Gly Ala Ala Pro
210                 215                 220

Val Ile Ala Gly Ile Ala Lys Ala Met Gly Ile Leu Thr Val Gly Ile
225                 230                 235                 240

Ala Thr Thr Pro Phe Ser Phe Glu Gly Arg Arg Thr Val Gln Ala
            245                 250                 255

Gln Glu Gly Leu Ala Ser Leu Arg Asp Asn Val Asp Thr Leu Ile Val
            260                 265                 270

Ile Pro Asn Asp Lys Leu Leu Thr Ala Val Ser Gln Ser Thr Pro Val
        275                 280                 285

Thr Glu Ala Phe Asn Leu Ala Asp Asp Ile Leu Arg Gln Gly Val Arg
        290                 295                 300

Gly Ile Ser Asp Ile Ile Thr Ile Pro Gly Leu Val Asn Val Asp Phe
305                 310                 315                 320

Ala Asp Val Arg Ala Ile Met Ala Asn Ala Gly Ser Ser Leu Met Gly
            325                 330                 335

Ile Gly Thr Ala Thr Gly Lys Ser Arg Ala Arg Asp Ala Ala Leu Asn
            340                 345                 350

Ala Ile Gln Ser Pro Leu Leu Asp Ile Gly Ile Glu Arg Ala Thr Gly
            355                 360                 365

Ile Val Trp Asn Ile Thr Gly Gly Ser Asp Leu Thr Leu Phe Glu Val
            370                 375                 380

Asn Ala Ala Glu Val Ile Tyr Asp Leu Val Asp Pro Thr Ala Asn
385                 390                 395                 400

Leu Ile Phe Gly Ala Val Val Asp Pro Ala Leu Ser Gly Gln Val Ser
            405                 410                 415

Ile Thr Leu Ile Ala Thr Gly Phe Lys Arg Gln Glu Glu Gly Glu Gly
            420                 425                 430

Arg Thr Val Gln Met Val Gln Ala Asp Ala Ala Ser Val Gly Ala Thr
            435                 440                 445

Arg Arg Pro Ser Ser Ser Phe Arg Glu Ser Gly Ser Val Glu Ile Pro
450                 455                 460

Glu Phe Leu Lys Lys Lys Gly Ser Ser Arg Tyr Pro Arg Val
465                 470                 475

<210> SEQ ID NO 38
<211> LENGTH: 473
<212> TYPE: PRT
<213> ORGANISM: Arabidopsis thaliana

<400> SEQUENCE: 38

Met Ala Ala Tyr Val Ser Pro Cys Leu Thr Pro Pro Asp Ser Arg Val
 1               5                  10                  15

Leu Thr Val Leu Arg Lys Ser Val Leu Pro Asp His His Leu Gly Thr
            20                  25                  30

Arg Val Gly Cys Leu Arg Met Ser Glu Gly Thr Thr Lys Arg Tyr Arg
        35                  40                  45

Val Val Ala Ser His Lys Tyr Glu Ser Ser Ser Ile Arg Asn Ser Leu
    50                  55                  60
```

```
Asn Ser His Ser Thr Ser His Phe Gln Ser Gln Asp Ser Phe Leu Asn
 65                  70                  75                  80

Leu His Pro Glu Ile Ser Met Leu Asn Pro Arg Lys Glu Thr Ser Ser
                 85                  90                  95

Val Pro Ile Thr Glu Asp Leu Asp Glu Leu Ser Thr Pro Asn Thr Tyr
            100                 105                 110

Asn Glu Ala Arg Ile Lys Val Ile Gly Val Gly Gly Gly Gly Ser Asn
        115                 120                 125

Ala Val Asn Arg Met Ile Glu Ser Glu Met Ile Gly Val Glu Phe Trp
    130                 135                 140

Ile Val Asn Thr Asp Ile Gln Ala Met Arg Ile Ser Pro Val Phe Pro
145                 150                 155                 160

Asp Asn Arg Leu Gln Ile Gly Lys Glu Leu Thr Arg Gly Leu Gly Ala
                165                 170                 175

Gly Gly Asn Pro Glu Ile Gly Met Asn Ala Ala Thr Glu Ser Lys Glu
            180                 185                 190

Ala Ile Gln Glu Ala Leu Tyr Gly Ser Asp Met Val Phe Val Thr Ala
        195                 200                 205

Gly Met Gly Gly Gly Thr Gly Thr Gly Gly Ala Pro Ile Ile Ala Gly
    210                 215                 220

Val Ala Lys Ala Met Gly Ile Leu Thr Val Gly Ile Val Thr Thr Pro
225                 230                 235                 240

Phe Ser Phe Glu Gly Arg Arg Arg Ala Leu Gln Ala Gln Glu Gly Ile
                245                 250                 255

Ala Ala Leu Arg Asp Asn Val Asp Thr Leu Ile Val Ile Pro Asn Asp
            260                 265                 270

Lys Leu Leu Ala Ala Val Ser Gln Ser Thr Pro Val Thr Glu Ala Phe
275                 280                 285

Asn Leu Ala Asp Asp Ile Leu Arg Gln Gly Val Arg Gly Ile Ser Asp
            290                 295                 300

Ile Ile Thr Ile Pro Gly Leu Val Asn Val Asp Phe Ala Asp Val Arg
305                 310                 315                 320

Ala Ile Met Ala Asn Ala Gly Ser Ser Leu Met Gly Ile Gly Thr Ala
            325                 330                 335

Thr Gly Lys Thr Arg Ala Arg Asp Ala Ala Leu Asn Ala Ile Gln Ser
            340                 345                 350

Pro Leu Leu Asp Ile Gly Ile Glu Arg Ala Thr Gly Ile Val Trp Asn
            355                 360                 365

Ile Thr Gly Gly Ser Asp Leu Thr Leu Phe Glu Val Asn Ala Ala Ala
370                 375                 380

Glu Val Ile Tyr Asp Leu Val Asp Pro Thr Ala Asn Leu Ile Phe Gly
385                 390                 395                 400

Ala Val Val Asp Pro Ser Tyr Ser Gly Gln Ile Ser Ile Thr Leu Ile
            405                 410                 415

Ala Thr Gly Phe Lys Arg Gln Glu Gly Glu Gly Arg Pro Leu Gln
            420                 425                 430

Ala Thr Gln Ala Asp Ala Ser Met Gly Ala Thr Arg Arg Pro Ser Ser
        435                 440                 445

Ser Phe Thr Glu Gly Ser Ser Ile Glu Ile Pro Glu Phe Leu Lys Lys
        450                 455                 460

Lys Gly Arg Ser Arg Tyr Pro Arg Leu
465                 470
```